US007314721B2

(12) United States Patent
Gure et al.

(10) Patent No.: US 7,314,721 B2
(45) Date of Patent: Jan. 1, 2008

(54) SMALL CELL LUNG CANCER ASSOCIATED ANTIGENS AND USES THEREFOR

(75) Inventors: Ali O. Gure, New York, NY (US); Elisabeth Stockert, New York, NY (US); Matthew J. Scanlan, New York, NY (US); Dirk Jager, New York, NY (US); Lloyd J. Old, New York, NY (US); Yao-Tseng Chen, New York, NY (US)

(73) Assignees: Ludwig Institute for Cancer Research, New York, NY (US); Memorial Sloan-Kettering Cancer Center, New York, NY (US); New York Hospital-Cornell Medical Center, New York, NY (US)

( * ) Notice: Subject to any disclaimer, the term of this patent is extended or adjusted under 35 U.S.C. 154(b) by 330 days.

(21) Appl. No.: 10/761,169

(22) Filed: Jan. 20, 2004

(65) Prior Publication Data

US 2004/0126808 A1 Jul. 1, 2004

Related U.S. Application Data

(62) Division of application No. 09/489,101, filed on Jan. 21, 2000, now abandoned.

(51) Int. Cl.
*G01N 33/53* (2006.01)
*C07K 1/00* (2006.01)
*C07K 16/00* (2006.01)

(52) U.S. Cl. ...................... 435/7.1; 530/350; 530/387.1

(58) Field of Classification Search .................. 435/4, 435/6, 7.1
See application file for complete search history.

(56) References Cited

U.S. PATENT DOCUMENTS 5,698,396 A 12/1997 Pfreundschuh

FOREIGN PATENT DOCUMENTS

| WO | WO 95/03422 A1 | 2/1995 |
| WO | WO 99/57438 A1 | 10/1999 |
| WO | WO 99/60160 A1 | 11/1999 |

OTHER PUBLICATIONS

Tockman et al (Cancer Res.. 1992, 52:2711s-2718s).*
Slamon et al. (Science vol. 235, Jan. 1987, pp. 177-182).*
Janeway and Travers (Immunobiology: The Immune System in Health and Disease, 1994, pp. 9:40-42.*
Stevanovic, M. et al., *Mammalian Genome* 5:640-642 (1994).
Collignon, J. et al., *Development* 122:509-520 (1996).
Graus, F. et al, *Journal of Clinical Oncology* 15:2866-2872 (1997).
Johnson, L. et al., *Molecular Reproduction and Development* 50:377-386 (1998).
Malas, S. et al., *Mammalian Genome* 10:934-937 (1999).
Ohwada, A. et al., *Am. J. of Respir. Cell and Mol. Biol.* 21:37-43 (1999).
Graham, J.D. et al., *Journal of Molecular Endocrinology* 22:295-304 (1999).
Manda, R. et al., *Genomics* 61:5-14 (1999).
Scanlan, M. et al., *Int. J. Cancer* 83:456-464 (1999).
Gure, A. et al., *Proc. Natl. Acad. Sci. USA* 97:4198-4203 (2000).
Sahin et al., *Proc. Natl. Acad. Sci USA* 92:11810-11813 (1995).
Chen et al., *Proc. Natl. Acad. Sci. USA* 94:1914-8 (1997).
Carney et al., *Cancer Res.* 45:2913-2923, 1985.
Park et al., *Cancer Res.* 47:6710-6718 (1987).
Old and Chen, *J. Exp. Med.*, 187:1163-7 (1998).
Chen et al., *Proc. Nat'l. Acad. Sci. USA*, 95: 6919-23 (1998).
Scanlan et al., *Int. J. Cancer* 76:652-658 (1998).
Riechmann et al., *Nucleic Acids Res.* 22: 749-755 (1994).
Shoji et al., *J. Biol. Chem.*, 270:24818-25 (1995).
Matsumoto-Taniura et al. *Mol. Biol. Cell*, 7: 1455-69 (1996).
Triebel et al., *J. Exp. Med.*, 171: 1393-1405 (1990).
Stockert et al., *J. Exp. Med.* 187:1349-1354 (1998).
Dalmau & Posner, *Arch. Neurol.* 56:405-408 (1999).
Posner & Dalmau, *Curr. Opin. Immunol.* 9:723-729 (1997).
Carpentier et al., *Clin. Cancer Res.* 4:2819-2824 (1998).
Stevanovic, M. Genbank Acc. No. Z31560. "H. Sapiens sox-2 mRNA (partial)", base pairs 1-500, Jul. 28, 1995.
Malas S. Genbank Acc. No. Y13436. "Homo sapiens sox1 gene", base pairs 1-500, May 28, 1997.
Kiesling, T.L. Genbank Acc. No. U28368. "Human ID-related helix-loop-helix protein Id4 mRNA, complete cds" base pairs 1-500, Aug. 3, 1995.

(Continued)

*Primary Examiner*—Susan Ungar
*Assistant Examiner*—Peter J. Redig
(74) *Attorney, Agent, or Firm*—Wolf, Greenfield & Sacks, P.C.

(57) ABSTRACT

Cancer associated antigens have been identified by autologous antibody screening of libraries of nucleic acids expressed in small cell lung cancer cells using antisera from cancer patients. The invention relates to nucleic acids and encoded polypeptides which are cancer associated antigens expressed in patients afflicted with small cell lung cancer. The invention provides, among other things, isolated nucleic acid molecules, expression vectors containing those molecules and host cells transfected with those molecules. The invention also provides isolated proteins and peptides, antibodies to those proteins and peptides and cytotoxic T lymphocytes which recognize the proteins and peptides. Fragments of the foregoing including functional fragments and variants also are provided. Kits containing the foregoing molecules additionally are provided. The molecules provided by the invention can be used in the diagnosis, monitoring, research, or treatment of conditions characterized by the expression of one or more cancer associated antigens.

10 Claims, 1 Drawing Sheet

OTHER PUBLICATIONS

Bossone, S.A. et al. Genbank Acc. No. M94046. "Human Zinc Finger Protein (Max) MRNA". Base Pairs 1-500. Apr. 27, 1993.

Matsumoto-Taniura, N. et al. Genbank Acc. No. X98260. "H. sapiens mRNA for M-phase phosphoprotein, mpp11". Base pairs 1-500. Jan. 8, 1997.

Asuru, A.I. et al. Genbank Acc. No. U23028. "Human eukaryotic initiation factor 2B-epsilon mRNA, partial cds." Base pairs 1-500. Aug. 22, 1996.

Amakawa, R. et. al. Genbank Acc. No. L07872. "Homo sapiens recombination signal binding protein (RBPJK) mRNA, partial cds." Base pairs 1-500, 1993.

Pardoll et al., Cancer vaccine, May 1998, Nature Medicine Vaccine Supplement, vol. 4, No. 5, pp. 525-531.

Malas, S. et al. Genbank Acc. No. AF107044. "Homo sapiens clone pCL4 DNA-binding protein SOX21 (SOX21) gene. complete cds." Base pairs 1-500. Dec. 13, 1998.

Ohara, O. et al. Genbank Acc. No. AB023180. "Homo sapiens mRNA for KiAA0963 protein, complete cds." Jun. 16, 1999.

Triebel, F. et al., Genbank Acc. No. X51985. "Human LAG-3 mRNA for CD4-related protein involved in lymphocyte activation." 1990.

Koehrer, K. et al. Genbank Acc. No. AL133561. Homo sapiens mRNA, cDNA DKFZp434C196 (from clone DKFZp434C196). base pairs 1-500. Dec. 15, 1999.

Vural et al., *Cancer* 2005; 103:2575-2538.

\* cited by examiner

```
SOX3          .........MRPVRENSSGARSPRVPADLARSILISLPFPPDSLAHRPPSSAPTESQGLFTVAAPAPGAPSPPATLAHLLPAPAMYSLLETELKNPVGT      90
SOX1   MYSMMETDLHSPGGAQAPTNLSGPAGAGGGGGGGGGGGGGGAKANQDRVKRPMNAFMVWSRGQRRKMAQENPKMHNSEISKRLGAEWKVMSEAEKRPFIDE     103
SOX2   MY-NMETELKPPGPQQTS-------GGGGGNSTAAAAGGNQKNSPDRVKRPMNAFMVWSRGQRRKMAQENPKMHNSEISKRLGAEWKLLSETEKRPFIDE      93
SOX3   PTQAAGTGGPAAPGGAGKSSANAAGGANSGGGSSGGASGGGGG--TDQDRVKRPANAFMVWSRGQRRKMALENPRKMHNSEISKRLGADWKLLTDAEKRPFIDE    191
SOX21  .................................MSKPVDHVKRPMNAFMVWSRAQRRKMAQENPKMHNSEISKRLGAEWKLLTESEKRPFIDE             60

SOX1   AKRLRALHMKEHPDYKYRPRRKTKTLLKKDKYSLA-----GGLLAAGAGGGGAVAMGVGVGVGA-APVGQRLESPGGAAGGAVAHVNGWANGAVPGAVAAAA    200
SOX2   AKRLRALHMKEHPDYKYRPRRKTKTLMKKDKYTLP------GGLLAAPG-------GNSMASGVGVGAGLGAGVNQRMDS---------YAHMNGWSNGSY-    171
SOX3   AKRLRAVHMKEYPDYKYRPRRKTKTLMKKDKYSLP-----SGLLPPGAAAAAAAAAAENPKMHNSEISKRLGAEWKLLTDAEKRPFIDE              272
SOX21  AKRLRAMHMKEHPDYKYRPRRKTKTLMKKDKFAFPVPYGLGGVADAEHPALKAGAGLHAGAGGGLVPESL-LANPEKAAAAAAAAARVFFPQSAAAAAAAAA     162

SOX1   AAAAMMQEAQLAYGQHPGAGGAHPHRTPAHPHPHHPHAH-PHNPQPMHRYDMGALQYSPISN--SQGYMSASPS-----GYGGLPYGAAAAAAAAAHQNSAVAA  295
SOX2   ---SMMQD--QLGYPQHPGL-------------------NAHGAAQMQBMHRYDVSALQYNSMTS--SQTYMNGSPT---------YSMSYSQQGTPG      234
SOX3   ---SLVQE--QLGYAAQPEPSMSS-------------------PPPPALHRYDMAGLQYSPMMPPGAQSYMNVAAAAAASGVGGMAPSATAAAAAYGQPATA   352
SOX21  AAAA-----------------------------------------GSPYSLLDLGSKMAEISSS-----SSGLPYASSL---GY---PTAGAGAFHGA--AAAAAA  214

SOX1   AAAAAASSGALGALGSLVKSEPSGSPP-----APAHSRAPC--PGDERENISMYLPAGEGG---DPAAAAAAQSRLHSLPQHYQGA---GAGVNGTVPLTHI    387
SOX2   MAIGSMGSVVKSEASSPPVTSSSPPVTSSSHSRAPCQAGDLERDMISMYLP-GAEVP---PSRLHMS-QHYQSGPVPGTAINGTLPLSHM             317
SOX3   AAAAMSLGPMGSVVKSEPSSPPP----AIASHSQRAC-LGDERDMISMYLPPG---DAADAASPLPGGRLHGVHQHYQGA---GTAVNGTVPLTHI        443
SOX21  AAAAA-------GGHTHSHPSPGNPGYMIPCNCSAWPSPGLQPPHA----YILLP-GMGKPQLDPYPAAYAAAL                              276
```

Fig. 1

SEQUENCE LISTING

```
<160> NUMBER OF SEQ ID NOS: 22

<210> SEQ ID NO 1
<211> LENGTH: 29
<212> TYPE: DNA
<213> ORGANISM: Homo sapiens

<400> SEQUENCE: 1
catgaatatg aacatgggta tgaacatgg                              29

<210> SEQ ID NO 2
<211> LENGTH: 23
<212> TYPE: DNA
<213> ORGANISM: Homo sapiens

<400> SEQUENCE: 2
tcgcagccct caaactcaca ctg                                    23

<210> SEQ ID NO 3
<211> LENGTH: 1085
<212> TYPE: DNA
<213> ORGANISM: Homo sapiens

<400> SEQUENCE: 3
```

-continued

```
cacagcgccc gcatgtacaa catgatggag acggagctga agccgccggg cccgcagcaa    60
acttcggggg gcggcggcgg caactccacc gcggcggcgg ccggcggcaa ccagaaaaac   120
agcccggacc gcgtcaagcg gcccatgaat gccttcatgg tgtggtcccg cgggcagcgg   180
cgcaagatgg cccaggagaa ccccaagatg cacaactcgg agatcagcaa gcgcctgggc   240
gccgagtgga aacttttgtc ggagacggag aagcggccgt tcatcgacga ggctaagcgg   300
ctgcgagcgc tgcacatgaa ggagcacccg gattataaat accggccccg gcggaaaacc   360
aagacgctca tgaagaagga taagtacacg ctgcccggcg ggctgctggc ccccggcggc   420
aatagcatgg cgagcggggt cggggtgggc gccggcctgg gcgcgggcgt gaaccagcgc   480
atggacagtt acgcgcacat gaacggctgg agcaacggca gctacagcat gatgcaggac   540
cagctgggct acccgcagca cccgggcctc aatgcgcacg gcgcagcgca gatgcagccc   600
atgcaccgct acgacgtgag cgccctgcag tacaactcca tgaccagctc gcagacctac   660
atgaacggct cgcccaccta cagcatgtcc tactcgcagc agggcacccc tggcatggct   720
cttggctcca tgggttcggt ggtcaagtcc gaggccagct ccagcccccc tgtggttacc   780
tcttcctccc actccagggc gccctgccag gccggggacc tccgggacat gatcagcatg   840
tatctccccg gcgccgaggt gccggaaccc gccgccccca gcagacttca catgtcccag   900
cactaccaga gcggcccggt gcccggcacg gccattaacg gcacactgcc cctctcacac   960
atgtgagggc cggacagcga actggagggg ggagaaattt tcaaagaaaa acgagggaaa  1020
tgggaggggt gcaaagagg agagtaagaa acagcatgga gaaaacccgg tacgctcaaa  1080
aaaaa                                                              1085
```

<210> SEQ ID NO 4
<211> LENGTH: 4091
<212> TYPE: DNA
<213> ORGANISM: Homo sapiens
<220> FEATURE:
<221> NAME/KEY: Unsure
<222> LOCATION: (2313)..(2313)
<223> OTHER INFORMATION: n = a, c, t or g
<220> FEATURE:
<221> NAME/KEY: Unsure
<222> LOCATION: (2540)..(2540)
<223> OTHER INFORMATION: n = a, c, t or g
<220> FEATURE:
<221> NAME/KEY: Unsure
<222> LOCATION: (2361)..(2361)
<223> OTHER INFORMATION: n = a, c, t or g

<400> SEQUENCE: 4

```
ccggccgtct atgctccagg ccctctcctc gcggtgccgg tgaacccgcc agccgccccg    60
atgtacagca tgatgatgga gaccgacctg cactcgcccg gcggcgccca ggcccccacg   120
aacctctcgg gccccgccgg ggcggcggcg ggcggggggcg gaggcggggg cggcggcggc   180
ggcgggggcg ccaaggccaa ccaggaccgg gtcaaacggc ccatgaacgc cttcatggtg   240
tggtcccgcg gcagcggcg caagatggcc caggagaacc ccaagatgca caactcggag   300
atcagcaagc gcctgggggc cgagtggaag gtcatgtccg aggccgagaa gcggccgttc   360
atcgacgagg ccagcgggct gcgcgcgctg cacatgaagg agcacccgga ttacaagtac   420
cggccgcgcc gcaagaccaa gacgctgctc aagaaggaca agtactcgct ggccggcggg   480
ctcctggcgg ccggcgcggg tggcggcggc gcggctgtgg ccatgggcgt gggcgtgggc   540
gtgggcgcgc gcccgtggg ccagcgcctg gagagcccag gcggcgcggc gggcggcggc   600
```

-continued

```
tacgcgcacg tcaacggctg ggccaacggc gcctacccg gctcggtggc ggccgcggcg        660
gccgccgcgg ccatgatgca ggaggcgcag ctggcctacg gcagcacccc cggcgcgggc        720
ggcgcgcacc cgcaccgcac cccggcgcac ccgcacccgc accacccgca cgcgcacccg        780
cacaacccgc agcccatgca ccgctacgac atgggcgcgc tgcagtacag ccccatctcc        840
aactcgcagg gctacatgag cgcgtcgccc tcgggctacg gcggcctccc ctacggcgcc        900
gcggccgccg ccgccgccgc gcaccagaac tcggccgtgg cggcggcggc ggcggcggcg        960
gccgcgtcgt cgggcgccct gggcgcgctg ggctctctgg tgaagtcgga gcccagcggc       1020
agcccgcccg cccagcgca ctcgcggcg ccgtgccccg gggacctgcg cgagatgatc        1080
agcatgtact tgcccgccgg cgaggggggc gacccggcgg cggcagcagc ggccgcggcg       1140
cagagccggc tgcactcgct gccgcagcac taccagggcg cgggcgcggg cgtgaacggc       1200
acggtgcccc tgacgcacat ctagcgcctt cgggacgccg gggactctgc ggcggcgacc       1260
cacgagctcg cggcccgcgc ccggctcccg ccccgcccg gcgcggcgtg gcttttgtat        1320
cagacgttcc cacattcttg tcaaaaggaa aatactggag acgaacgccg ggtgacgcgt       1380
gtcccccact caccttcccc ggagaccctg gcgaccgccg ggcgctgaca ccagacttgg       1440
tttagactga acttcggtgt tttcttgaga cttttgtaca gtatttatca cctacggagg       1500
aagcggaagc gttttctttg ctcgagggga caaaaaagtc aaaacgaggc gagaggcgaa       1560
gcccactttt gtataccggc cggcgcgctc actttcctcc gcgttgcttc cggacggcgc       1620
cgaccgccgg agcccaagtg acgcggagct cgtcgcattt gttataaatg tagtaaggca       1680
ggtccaagca cttacaagtt ttttgtagtt gttaccgctc ttttgggttg gtttgttaat       1740
ttatacaaag agattaccac caccacccccc tccttcagac ggcggagtta tattctgggt      1800
tttgtaaaac tttatgtatc tgagcatttc cattttttt ttttgggtttt gtattatttc      1860 ttgtaaatgc attgtgaaaa attttatttt cggcgttgca atgcggggag gagaagtcag      1920
attatgtaca tagttttcta aaaagccttt cttctaaaaa cgaaaaaaga cccccaccca      1980
aaatgtttcg agtcaacaaa tttaagagac agagcccatt ttctccataa atttgtaaca      2040
tgcctatttt tatgtgcatg ttttatgagt tcaaaatgca atgagggaaa tctgacaggg      2100
aaattatctg tatgaactaa aagtaaggga acccggggaa tgggaggaca ggattttttca     2160 aggaacctt ttcaatgaaa gagaaggaag ttaaaaccta taggttattt tgtagagctg       2220
agtgttaata cggccgaga aataaaagta tcttctgctc cggctgtttc actgcggacg       2280 gctgggctg ctgcgcgtta ccttgctgca acnggcgcc ttccacctgg ctgggggtct       2340
gcgccacagt ttggtccaga ngwgggagga ggaagggaag accccagtgg tgggaccctg      2400
gaccaggcca tggatgaagg acaaagacca gggcaggtca cgggtttccc aattccccag      2460
caattaagat ttcgagcaga atttatctaa atgtgtttca aggaaacaca atcgctgaac      2520
caaaacgtac tgcagccgan ccccctccgt ccatcctctg cccctccccc tggcttcttt      2580
ctcttgggaa aacgggcaaa ataattgtgc tggattctca cacacacaga aatatcgacc      2640
atcaccctcc cccgcgtgaa ctgggatgca agttgctaac cgatgtgaac gcaaaatgcc      2700
ttgttcatta ttcctgacga gatcttgagg ttgtttgatg ctttaaattt tttaattata      2760 ttatttcta ggtgtttatt ggtacattgc agttttttt ttgaaattta aaatttctg        2820 taaaactttg tcttcaagta atctgacagc attaaatatt gcatttaaaa attatactgt      2880
agcaaataca tttaaaaatt aatcacaacg ttaagatgaa attatatttt tggaaaaaaa      2940
aaacacttga agcccagatg gaaatacgtt tatttcagca gccttaggtt tcccctcgct      3000
```

-continued

```
ttctcaacac ccttccttgt cctggagtat ggactgtccg tccaaaagtg agcctatgct      3060
ataagtttaa tgagaaccga attcagcctg cattcgagaa tagctttaag tataatgctg      3120
atctgacaat tgacgtgtaa tttgggaagt cattttgata attttgctta aaccactcat      3180
tcgttaaagt gattacaaaa aagttcaaga atgatgtcca ctgctttcta acaagataat      3240
aaaccccccc cctctttttct ttttctttat ttttatttct tttagctatt tgatcctttc     3300
tgaagcagtt gtttctggaa gagtctgtgc gcccatggat ggctgagcac cactacgact      3360
tagtccggga taagggcctc cccagtcctc tccgggagat gatttgggaa attttataat      3420
gcttgttctg ttaactcacc gggaccttga gggtccaatg ggaccttgag ggttttctct      3480
gaaatataca aacttaaagg actctctctg aggttctttg actgacgtcc actctcagtc      3540
tggcccctgt gctcccctgt gtgtaccctg gagtttctgt gtccaattgt tggcatctag      3600
gtcttggctc aagattagga tgtgggcccc actttagagg cacagactat gaaaagctga      3660
gttagtgcgc ccgggacgcc aggcaagcag ctttttacagt ttggcatctt attgcaggtg      3720
cttcgtgcac agtcagctga aatagccaat gccaggtgct ccaaccaccct tatttccttg     3780 ttttgttgat tagaacaaca cagaaaaaag caaatataaa tttttaatga ctccatttaa      3840
aaatatcaca gggtgggggc aaggaaatta gctgagattc atctcaggat tgagattcta      3900
tccccccttc cccgccccca gcagtgtcgc tccaattcaa attagtggag aaaagattac      3960
agtaggccct gagccgactg tgaattcggt gcttggccaa ggtaacactc atcgtattca      4020
cggagraaat actatatgat gatagttatt atattatatg acgacttcat tcacttccca      4080
aatcacaggg t                                                           4091
```

<210> SEQ ID NO 5
<211> LENGTH: 1602
<212> TYPE: DNA
<213> ORGANISM: Homo sapiens

<400> SEQUENCE: 5

```
atgctcctgg acgcgggtcc gcagttcccg gccatcgggg tgggcagctt cgcgcgccac      60
catcaccact ccgccgcggc ggcggcggcg gctgccgccg agatgcagga ccgtgaactg      120
agcctggcgg cggcgcagaa cggcttcgtt gattccgccg ccgcgcacat gggagccttc      180
aagctcaacc cgggcgcgca cgagctgtcc ccgggccaga gctcggcgtt cacgtcgcag      240
ggccccggcg cctaccccgg ctccgctgcg gctgccgctg cggccgcagc gctcgggccc      300
cacgccgcgc acgttggctc ctactctggg ccgcccttca actccacccg ggacttcctg      360
ttccgcagcg cgcggcttcc ggggacttcg gcgccgggcg gcgggcagca cgggctgttc      420
gggccgggcg cgggcggcct gcaccacgcg cactcggacg cgcagggcca cctcctcttc      480
ccgggcctgc cagagcagca cgggccgcac ggctcgcaga atgtgctcaa cgggcagatg      540
cgcctcgggc tgcccggcga ggtgttcggg cgctcggagc aataccgcca ggtggccagc      600
ccgcggaccg accctactc ggcggcgcaa ctccacaacc agtacggccc catgaatatg      660
aacatgggta tgaacatggc agcagccgcg gcccaccacc accaccacca ccaccaccac      720
cccggtgcct ttttccgcta tatgcggcag cagtgcatca gcaggagct aatctgcaag      780 tggatcgacc ccgagcaact gagcaatccc aagaagagct gcaacaaaac tttcagcacc      840
atgcacgagc tggtgacaca cgtctcggtg gagcacgtcg gcggcccgga gcagagcaac      900
cacgtctgct ctctgggagga gtgtccgcgc gagggcaagc ccttcaaggc caaatacaaa      960
```

```
ctggtcaacc acatccgcgt gcacacaggc gagaaaccct tcccctgccc cttcccgggc      1020
tgtggcaaag tcttcgcgcg ctccgagaac ctcaagatcc acaaaaggac ccacacaggg      1080
gagaagccgt tccagtgtga gtttgagggc tgcgaccggc gcttcgccaa cagcagcgac      1140
aggaagaagc acatgcacgt ccacacctcc gataagccct atctctgcaa gatgtgcgac      1200
aagtcctaca cgcaccccag ctcgctgcgg aagcacatga aggtccatga gtcctccccg      1260
cagggttctg aatcctcccc ggccgccagc tccggctatg agtcgtccac gccccgggg       1320 ctggtgtccc ccagcgccga gccccagagc agctccaacc tgtccccagc ggcggcggca      1380
gcggcggcgg cggctgcggc ggcggcggcc gcggtgtccg cggtgcaccg gggcggaggc      1440
tcgggcagtg gcggcgcggg aggcggctca ggcggcggca gcggcagtgg cgggggcggc      1500
ggcggggcgg gcggcggggg cggcggcagc tctggcgggg gcagcgggac agccgggggt      1560
cacagcggcc tctcctccaa cttcaatgaa tggtacgtgt ga                         1602

<210> SEQ ID NO 6
<211> LENGTH: 1322
<212> TYPE: DNA
<213> ORGANISM: Homo sapiens

<400> SEQUENCE: 6
ggaattccgg gcgcggttgt gagtagtacc gggagtgggg tgatcccggg ctaggggagc        60
gcggcgcccg atcgggctta gtcggagctc cgaagggagt gactaggaca cccgggtggg       120 ctactttct tccggtgctt ttgcttttt tttcctttgg gctcgggctg agtgtcgccc         180
actgagcaaa gattccctcg taaaacccag agcgaccctc ccgtcaattg ttgggctcgg       240
gagtgtcgcg gtgccccgag cgcgccgggc gcggaggcaa agggagcgga gccgccgcg        300 gacggggccc ggagcttgcc tgcctccctc gctcgcccca gcgggttcgc tcgcgtagag      360 cgcaggcgc gcgcgatgaa ggcggtgagc ccggtgcgcc cctcgggccg caaggcgccg        420
tcgggctgcg gcggcgggga gctggcgctg cgctgcctgg ccgagcacgg ccacagcctg       480
ggtggctccg cagccgcggc ggcggcggcg cggcagcgc gctgtaaggc ggccgaggcg        540
gcggccgacg agccggcgct gtgcctgcag tgcgatatga acgactgcta tagccgcctg      600
cggaggctgg tgcccaccat cccgcccaac aagaaagtca gcaaagtgga gatcctgcag      660
cacgttatcg actacatcct ggacctgcag ctggcgctgg agacgcaccc ggccctgctg       720
aggcagccac caccgcccgc gccgccacac cacccggccg ggacctgtcc agccgcgccg       780
ccgcggaccc cgctcactgc gctcaacacc gacccggccg cgcgggtgaa caagcagggc      840
gacagcattc tgtgccgctg agccgcgctg tccaggtgtg cggccgcctg agcccgagcc       900
aggagcacta gagagggagg gggaagagca gaagttagag aaaaaaagcc accggaggaa      960
aggaaaaaac atcggccaac ctagaaacgt tttcattcgt cattccaaga gagagagg       1020 aaagaaaaat acaactttca ttctttcttt gcacgttcat aaacattcta catacgtatt      1080
ctcttttgtc tcttcattta aactgctgt gaattgtaca tttctgtgtt ttttggaggt     1140
gcagttaaac ttttaagctt aagtgtgaca ggactgataa atagaagatc aagagtagat     1200
ccgactttag aagcctactt tgtgaccaag gagctcaatt tttgttttga agctttacta      1260
atctaccaga gcattgtaga tattttttt ttacatctat tgtttaaaat agccggaatt      1320
cc                                                                   1322

<210> SEQ ID NO 7
<211> LENGTH: 2389
```

<212> TYPE: DNA
<213> ORGANISM: Homo sapiens

<400> SEQUENCE: 7

| | | | | | |
|---|---|---|---|---|---|
| cggctcagcg | ggggccgagg | ccatgttccc | ggtgtttcct | tgcacgctgc | tggccccccc | 60 |
| cttcccgtg | ctgggcctgg | actcccgggg | ggtgggcggc | ctcatgaact | ccttcccgcc | 120 |
| acctcagggt | cacgcccaga | acccctgca | agtcggggct | gagctccagt | cccgcttctt | 180 |
| tgcctcccag | ggctgcgccc | agagtccatt | ccaggccgcg | ccggcgcccc | cgcccacgcc | 240 |
| ccaggccccg | gcgccgagc | ccctccaggt | ggacttgctc | ccggtgctcg | ccgccgccca | 300 |
| ggagtccgcc | gcggctgctg | cggccgctgc | cgccgctgct | gccgccgtcg | ctgccgcgcc | 360 |
| cccgccccct | gccgccgcct | ctacggtgga | cacagcggcc | ctgaagcagc | tccggcgcc | 420 |
| ccctccgcca | ccccgccag | tgtcggcgcc | cgcggccgag | gccgcgcccc | cgcctccgc | 480 |
| cgccactatc | gccgcggcgg | cggccaccgc | cgtcgtagcc | caacctcga | cggtcgccgt | 540 |
| ggccccggtc | gcgtctgcct | tggagaagaa | gacaaagagc | aaggggccct | acatctgcgc | 600 |
| tctgtgcgcc | aaggagttca | gaacggcta | caatctccgg | aggcacgaag | ccatccacac | 660 |
| gggagccaag | gccggccggg | tcccctcggg | tgctatgaag | atgccgacca | tggtgcccct | 720 |
| gagcctcctg | agcgtgcccc | agctgagcgg | agccggcggg | ggagggggag | aggcgggtgc | 780 |
| cggcggcggc | gctgccgcag | tggccgccgg | tggcgtggtg | accacgaccg | cctcggggaa | 840 |
| gcgcatccgg | aagaaccatg | cctgcgagat | gtgtggcaag | gccttccgcg | acgtctacca | 900 |
| cctgaaccga | cacaagctgt | cgcactcgga | cgagaagccc | taccagtgcc | cggtgtgcca | 960 |
| gcagcgcttc | aagcgcaagg | accgcatgag | ctaccacgtg | cgctcacatg | acggcgctgt | 1020 |
| gcacaagccc | tacaactgct | cccactgtgg | caagagcttc | tcccggccgg | atcacctcaa | 1080 |
| cagtcacgtc | agacaagtgc | actcaacaga | acggcccttc | aaatgtgaga | aatgtgaggc | 1140 |
| agctttcgcc | acgaaggatc | ggctgcgggc | gcacacagta | cgacacgagg | agaaagtgcc | 1200 |
| atgtcacgtg | tgtggcaaga | tgctgagctc | ggcttatatt | tcggaccaca | tgaaggtgca | 1260 |
| cagccagggt | cctcaccatg | tctgtgagct | ctgcaacaaa | ggtactggtg | aggtttgtcc | 1320 |
| aatggcggcg | gcagcggcag | cggcggcagc | ggcagcagcg | gcagcagtag | cagcccctcc | 1380 |
| cacagctgtg | ggctccctct | cggggggcgga | ggggtgcct | gtgagctctc | agccacttcc | 1440 |
| ctcccaaccc | tggtgagctc | caagttggtt | gcggggggaga | ggggagaatg | gagtagagtc | 1500 |
| ccttggtaca | agctcctctc | ccccctcttt | tcccaccaac | tcctatttcc | ctaccaacca | 1560 |
| aggagcctcc | agaaggaaag | gaggaagaaa | tgttttctta | ggggaattcg | ctaggtttta | 1620 |
| acgatttgct | tctcctgctc | ctcttctatc | agacctgacc | ccacacaaac | ctgtcccctc | 1680 |
| ggttgtgttg | aagtcccctg | gacagtgggc | agggtggca | gaggacacga | gcagccactg | 1740 |
| cccgtacccc | ctctcctctc | tgtaagccca | tgccctgtct | tcccagggac | ttgtgagcct | 1800 |
| cttccctcga | cggtcctctt | ctctccttcc | agtcctctcc | ccctgctgtc | tgcagcccct | 1860 |
| ccccggggag | ttggtgcttt | cttttcctttt | tttttttttt | ttccagggg | agggaggaga | 1920 |
| ggaaggaggg | ggatcagagc | tgtcccaaag | agggaaagcg | gtgaggtttg | aggaggggca | 1980 |
| gaagcagggc | cggcaaaggt | tgtaccttca | taaggtggta | tcgggggtt | ggggtcaggc | 2040 |
| cctgaacatc | gtcctacttg | agaatctgtc | agggaaaaa | gtcaagggga | gcaggaggaa | 2100 |
| gagccaggag | ggccagaggc | agagaagaga | tggagtctta | ggggccaggg | tgagccaggg | 2160 |
| gtccagggcc | tagaggtgct | tctgggggggg | ggggaatgca | gccagtgtcc | ccctcccctc | 2220 |

-continued

| | | | |
|---|---|---|---|
| ttccacccca | gctccagccc | tggtcttgtc | ttttcatccc tcttccccac gacagaagaa | 2280 |
| gttgtggccc | tggcatgtca | tcgtgttcct | gtgtcccctg catgtacccc accctccacc | 2340 |
| ccttccttt | gcgcggaccc | cattacaata | aattttaaat aaaatcctg | 2389 |

<210> SEQ ID NO 8
<211> LENGTH: 1860
<212> TYPE: DNA
<213> ORGANISM: Homo sapiens

<400> SEQUENCE: 8

| | | | | |
|---|---|---|---|---|
| gggacgtgag | ccgctgcgcc | caccgggcta | gacccggcgc catcatgctg cttctgccaa | 60 |
| gcgccgcgga | cggccggggc | accgccatca | cccacgctct gacctctgcc tctacactct | 120 |
| gtcaagttga | acctgtggga | agatggtttg | aagcttttgt taagaggaga aacagaaatg | 180 |
| cttctgcctc | ttttcaggaa | ctggaggata | gaaagagtt atccgaggaa tcagaagatg | 240 |
| aagaattgca | gttggaagag | tttcccatgc | tgaaaacact tgatcccaaa gactggaaga | 300 |
| accaagatca | ttatgcagtt | cttggacttg | gccatgtgag atacaaggct acacagagac | 360 |
| agatcaaagc | agctcataaa | gcaatggttt | taaaacatca cccagacaaa cggaaagcag | 420 |
| ctggtgaacc | aataaaagaa | ggagataatg | actacttcac ttgcataact aaagcttatg | 480 |
| aaatgttatc | tgatccagtg | aaaagacgag | catttaacag tgtagatcct acttttgata | 540 |
| actcagttcc | ttctaaaagt | gaagcaaagg | ataatttctt cgaagtgttt accccagtgt | 600 |
| ttgaaaggaa | ttccagatgg | tcaaataaaa | aaatgttcc taaacttggt gatatgaatt | 660 |
| catcatttga | agatgtagat | atattttatt | cttctggta taattttgat tcttggagag | 720 |
| aattttctta | tttagatgaa | gaagaaaaag | aaaaagcaga atgtcgtgat gagaggagat | 780 |
| ggattgaaaa | gcagaacgga | gcaacaagag | cacaaagaaa aaagaagaa atgaacagaa | 840 |
| taagaacatt | agttgacaat | gcatacagct | gtgatccaag gataaaaaag ttcaaggaag | 900 |
| aagaaaaagc | caagaaagaa | gcagaaaaga | agcaaaagc agaagctaaa cggaaggagc | 960 |
| aagaagctaa | agaaaaacaa | agacaagctg | aattagaagc tgctcggtta gctaaggaga | 1020 |
| aagaagagga | ggaagtcaga | cagcaagcat | tgctggcaaa gaaggaaaaa gatatccaga | 1080 |
| aaaaagccat | taagaaggaa | aggcaaaaac | ttcgaaactc atgcaagata gaagaaataa | 1140 |
| atgagcaaat | cagaaaagag | aaagaggaag | ctgaggctcg tatgcgacaa gcatctaaga | 1200 |
| acacagagaa | atcaactggt | ggaggtggaa | atggaagtaa aaattggtca gaagatgatc | 1260 |
| tacaattact | aattaaagct | gtgaatctgt | tccctgctag aacaaattca agatgggaag | 1320 |
| ttattgctaa | ttcatgaac | atacattctt | cctctggagt caaaagaact gccaaagatg | 1380 |
| ttattggcaa | agcaaagagt | ctccaaaaac | ttgaccctca tcaaaagat gacataaata | 1440 |
| aaaaggcatt | tgataagttc | aaaaaagaac | atggagtggt acctcaagca gacaacgcaa | 1500 |
| cgccttcaga | acgatttgaa | ggtccatata | cagacttcac cccttggaca acagaagaac | 1560 |
| agaagctttt | ggaacaagct | ttgaaaacat | acccagtaaa tacacctgaa agatgggaaa | 1620 |
| aaatagcaga | agcggtgcct | ggcaggacaa | agaaggactg catgaaacga tacaaggaac | 1680 |
| ttgtcgagat | ggtaaaagca | aagaaagctg | ctcaagaaca agtgctgaat gcaagtagag | 1740 |
| ccaagaaatg | acaatctttg | ttgtgtgtgc | attttataa taaaactgaa aatactgtaa | 1800 |
| acattttcat | tcttaaaatt | atactcatgg | taataatttg aaagtaaaaa aaaaaaaaaa | 1860 |

<210> SEQ ID NO 9
<211> LENGTH: 2291

<212> TYPE: DNA
<213> ORGANISM: Homo sapiens

<400> SEQUENCE: 9

```
gaattcctga ctgccacagg tgtacaggaa acatttgtct tttgttgctg gaaagctgct      60
caaatcaaag aacatttact gaagtcaaag tggtgccgcc ctacatctct caatgtggtt     120
cgaataatta catcagagct ctatcgatca ctgggagatg tcctccgtga tgttgatgcc     180
aaggctttgg tgcgctctga ctttcttctg tgtatgggg atgtcatctc aaacatcaat     240
atcaccagag cccttgagga acacaggttg agacggaagc tagaaaaaaa tgtttctgtg     300
atgacgatga tcttcaagga gtcatccccc agccacccaa ctcgttgcca cgaagacaat     360
gtggtagtgg ctgtggatag taccacaaac agggttctcc attttcagaa gacccagggt     420
ctccggcgtt ttgcatttcc tctgagcctg tttcagggca gtagtgatgg agtggaggtt     480
cgatatgatt tactggattg tcatatcagc atctgttctc ctcaggtggc acaactcttt     540
acagacaact ttgactacca aactcgagat gactttgtgc gaggtctctt agtgaatgag     600
gagatcctag ggaaccagat ccacatgcac gtaacagcta aggaatatgg tgcccgtgtc     660
tccaacctac acatgtactc agctgtctgt gctgacgtca tccgccgatg ggtctaccct     720
ctcaccccag aggcgaactt cactgacagc accacccaga gctgcactca ttcccggcac     780
aacatctacc gagggcctga ggtcagcctg ggccatggca gcatcctaga ggaaaatgtg     840
ctcctgggct ctggcactgt cattggcagc aattgcttta tcaccaacag tgtcattggc     900
cccggctgcc acattggtga taacgtggtg ctggaccaga cctacctgtg cagggtgtt      960
cgagtggcgg ctggagcaca gatccatcag tctctgcttt gtgacaatgc tgaggtcaag    1020
gaacgagtga cactgaaacc acgctctgtc ctcacttccc aggtggtcgt gggcccaaat    1080
atcacgctgc ctgagggctc ggtgatctct ttgcaccctc cagatgcaga ggaagatgaa    1140
gatgatggcg agttcagtga tgattctggg gctgaccaag aaaaggacaa agtgaagatg    1200
aaaggttaca atccagcaga agtaggagct gctggcaagg gctacctctg gaaagctgca    1260
ggcatgaaca tggaggaaga ggaggaactg cagcagaatc tgtggggact caagatcaac    1320
atggaagaag agagtgaaag tgaaagtgag caaagtatgg attctgagga gccggacagc    1380
cggggaggct cccctcagat ggatgacatc aaagtgttcc agaatgaagt tttaggaaca    1440
ctacagcggg gcaaagagga gaacatttct tgtgacaatc tcgtcctgga aatcaactct    1500
ctcaagtatg cctataacgt aagtctaaag gaggtgatgc aggtactgag ccacgtggtc    1560
ctggagttcc ccctgcaaca gatggattcc ccgcttgact caagccgcta ctgtgccctg    1620
ctgcttcctc tgctaaaggc ctggagccct gttttttagga actacataaa gcgcgcagcc    1680
gaccatttgg aagcgttagc agccattgag gacttcttcc tagagcatga agctcttggt    1740
atttccatgg ccaaggtact gatggctttc taccagctgg agatcctggc tgaggaaaca    1800
attctgagct ggttcagcca aagagataca actgacaagg ccagcagtt gcgcaagaat    1860
caacagctgc agaggttcat ccagtggcta aagaggcag aagaggagtc atctgaagat    1920
gactgaagtc acactgcctg ctccttggg tgtgattgag tgccctcctg ctcctgggc    1980
tgggacaagt gaggaactag ctgcagaggg atgagtgacc accatccagg ctgagactga    2040
aaggagcaga ggctggaact acagtattct ttccctgct agcaaccatg tgcctcccat    2100
cctgactgtg gagttgggat gtggaagtgg ggctggaaca aagcttctgc ctagggagga    2160
gctaagcagg cccggcagtt ggaggaaggc cagaggaaca gctttgtgct ccggctttcc    2220
```

| | |
|---|---:|
| ctcagggaac agcagagagc agttggctct ttctgctgct tgtatatgtt aatattaaaa | 2280 |
| gagagtggtg t | 2291 |

<210> SEQ ID NO 10
<211> LENGTH: 1580
<212> TYPE: DNA
<213> ORGANISM: Homo sapiens

<400> SEQUENCE: 10

| | |
|---|---:|
| atcccctccg gttttcctca gtctccacgt acgtccctca aagcgcgtcc taaaacccgg | 60 |
| ataaccggag cgctccccat ggaccacacg gagggcttgc ccgcggagga gccgcctgcg | 120 |
| catgctccat cgcctgggaa atttggtgag cggcctccac ctaaacgact tactagggaa | 180 |
| gctatgcgaa attatttaaa agagcgaggg gatcaaacag tacttattct tcatgcaaaa | 240 |
| gttgcacaga agtcatatgg aaatgaaaaa aggttttttt gcccacctcc ttgtgtatat | 300 |
| cttatgggca gcggatggaa gaaaaaaaaa gaacaaatgg aacgcgatgg ttgttctgaa | 360 |
| caagagtctc aaccgtgtgc atttattggg ataggaaata gtgaccaaga aatgcagcag | 420 |
| ctaaacttgg aaggaaagaa ctattgcaca gccaaaacat tgtatatatc tgactcagac | 480 |
| aagcgaaagc acttcatttt ttctgtaaag atgttctatg caacagtga tgacattggt | 540 |
| gtgttcctca gcaagcggat aaaagtcatc tccaaacctt ccaaaaagaa gcagtcattg | 600 |
| aaaaatgctg acttatgcat tgcctcagga acaaggtgg ctctgtttaa tcgactacga | 660 |
| tcccagacag ttagtaccag atacttgcat gtagaaggag gtaattttca tgccagttca | 720 |
| cagcagtggg gagccttttt tattcatctc ttggatgatg atgaatcaga aggagaagaa | 780 |
| ttcacagtcc gagatgtcta catccattat ggacaaacat gcaaacttgt gtgctcagtt | 840 |
| actggcatgg cactcccaag attgataatt atgaaagttg ataagcatac cgcattattg | 900 |
| gatgcagatg atcctgtgtc acaactccat aaatgtgcat tttaccttaa ggatacagaa | 960 |
| agaatgtatt tgtgcctttc tcaagaaaga ataattcaat ttcaggccac tccatgtcca | 1020 |
| aaagaaccaa ataaagagat gataaatgat ggcgcttcct ggacaatcat tagcacagat | 1080 |
| aaggcagagt atacatttta tgagggaatg ggccctgtcc ttgccccagt cactcctgtg | 1140 |
| cctgtggtag agagccttca gttgaatggc ggtggggacg tagcaatgct gaacttaca | 1200 |
| ggacagaatt tcactccaaa tttacgagtg tggtttgggg atgtagaagc tgaaactatg | 1260 |
| tacaggtgtg gagagagtat gctctgtgtc gtcccagaca tttctgcatt ccgagaaggt | 1320 |
| tggagatggg tccggcaacc agtccaggtt ccagtaactt tggtccgaaa tgatggaatc | 1380 |
| atttattcca ccagccttac ctttacctac acaccagaac cagggccacg gccacattgc | 1440 |
| agtgtagcag gagcaatcct tccagccaat tcaagccagg tgcccctaa cgaatcaaac | 1500 |
| acaaacagcg agggaagtta cacaaacgcc agcacaaatt caaccagtgt cacatcatct | 1560 |
| acagccacag tggtatccta | 1580 |

<210> SEQ ID NO 11
<211> LENGTH: 2509
<212> TYPE: DNA
<213> ORGANISM: Homo sapiens

<400> SEQUENCE: 11

| | |
|---|---:|
| tggccggggg atgggcgcc ggtctgcctt gacagggttg caaagttgtt ttctaaattc | 60 |
| cgaagcgccc ctctgccccc tcccccaat ctgcttgcgt cggggtggg gggtgggggg | 120 |
| gtcacctcct caggtttcgt tctttcaaac tttttgaaac cctaattggt ggcctctgag | 180 |

-continued

```
tgggcctcgt ggactcccgc ctcctaagta actcttacca cgtcactagg ccaaagaggg      240
gcgtggggtg aacgaaaggg ctcccgaact ttttttttc cagccaggcc gaacggggc       300 tcggtaatga ttggccaggg cgcatcactg cgaacctgtc aatcacgggt cctccgggtt     360
gcgaggggcg gaccaagccc caaccccggg gaatccgagc aggtatataa ggggcccagc    420
tagagcccag gcagactgtg aatgcgacct gttcgagaga actcatcagg tgcgagaagc    480
ccgcgggttc ctgctgattt ggcgcggagc attttgataa gcctacccct cccgccggac   540
tcgctggccc acaggccccc aagctccgct ccgacggagt cccagggcct tttcaccgtg   600
gccgctccag ccccgggagc gccttctcct cccgccacgc tggcgcacct tcttcccgcc   660
ccggcaatgt acagccttct ggagactgaa ctcaagaacc ccgtagggac acccacacaa   720
gcggcgggca ccggcggccc cgcagccccg ggaggcgcag gcaagagtag tgcgaacgca   780
gccggcggcg cgaactcggg cggcggcagc agcggtggtg cgagcggagg tggcggggt    840 acagaccagg accgtgtgaa acggcccatg aacgccttca tggtatggtc ccgcgggcag   900
cggcgcaaaa tggccctgga gaaccccaag atgcacaatt ctgagatcag caagcgcttg   960
ggcgccgact ggaaactgct gaccgacgcc gagaagcgac cattcatcga cgaggccaag  1020
cgacttcgcg ccgtgcacat gaaggagtat ccggactaca agtaccgacc cgcccgcaag  1080
accaagacgc tgctcaagaa agataagtac tccctgccca gcggcctcct gcctcccggt  1140
gccgcggccg ccgccgccgc tgccgcggcc gcagccgctg ccgccagcag tccggtgggc  1200
gtgggccagc gcctggacac gtacacgcac gtgaacggct gggccaacgg cgcgtactcg  1260
ctggtgcagg agcagctggg ctacgcgcag ccccgagca tgagcagccc gccgccgccg   1320
cccgcgctgc accgctacga catggccggc ctgcagtaca gcccaatgat gccgcccggc  1380
gctcagagct acatgaacgt cgctgccgcg ccgccgccg cctcgggcta cgggggcatg   1440
gcgccctcag ccacagcagc cgcggccgcc gcctacgggc agcagccgc caccgccgcg   1500 gccgcagctg cggccgcagc cgccatgagc ctgggcccca tgggctcggt agtgaagtct  1560
gagcccagct cgccgccgcc cgccatcgca tcgcactctc agcgcgcgtg cctcggcgac  1620
ctgcgcgaca tgatcagcat gtacctgcca cccggcgggg acgcggccga cgccgcctct  1680
ccgctgcccg gcgtcgcct gcacggcgtg caccagcact accagggcgc cgggactgca   1740
gtcaacggaa cggtgccgct gacccacatc tgagcaccgg cctgcgctcg tccacccttg  1800
ttccccaccc ccaccccca tcccgccccg caccccaag ttgggtcgcc ttgtttagct    1860
ttgcttgcct gggactgttg ccttgtaccg atgatgggga gggctgaaag ttttgctgta  1920
gctgtcgggt tttgtacaaa agtcaaaaat aagtcaggag cagcgaaaat gggatcttct  1980
agagagctct cttgccccac gccgctgctc ctttcacctt tgtaggctgg gaatcgctgt  2040
gttatttgca aagaaaaaac agcccccact cctcctcctg agttccaggg ttattctgtt  2100
acatttgaaa atgttgtctt gttagtttgc agttagccaa ggagtgaatg ggagaaacat  2160
agtatcgggt gaggtccagc tgagaactg caacgcctac gccccagtc gtgtcgcgtc    2220 tgttttcctc gaggtttttt ggggcgctga ccgctccaag cagcgcggca gctaaagcca  2280
atgttaattt atagccaggt gtgcgtgtgt ctcccgcctc gccgcccctg gccgcgggac  2340
agcttctgtc caatcatgtt gagttggtga tttctgccgt gatctgtttg atatttcttc   2400
gcgctaatgt gttcgatttt cgtttgggta gtggggaggg gctactttgt ttcagggttt  2460
tcaagctttt actcttaatt cctaaatgag atcaataaat tttataacc                 2509
```

<210> SEQ ID NO 12
<211> LENGTH: 8372
<212> TYPE: DNA
<213> ORGANISM: Homo sapiens
<220> FEATURE:
<221> NAME/KEY: Unsure
<222> LOCATION: (2677)..(2677)
<223> OTHER INFORMATION: n = a, c, t or g
<220> FEATURE:
<221> NAME/KEY: Unsure
<222> LOCATION: (5121)..(5121)
<223> OTHER INFORMATION: n = a, c, t or g
<220> FEATURE:
<221> NAME/KEY: Unsure
<222> LOCATION: (5117)..(5117)
<223> OTHER INFORMATION: n = a, c, t or g
<220> FEATURE:
<221> NAME/KEY: Unsure
<222> LOCATION: (5116)..(5116)
<223> OTHER INFORMATION: n = a, c, t or g

<400> SEQUENCE: 12

```
aagcttggtg ccatctattt tggactatgc cttgcataca gctttatggg aacatttgtc      60
aggcaaaagt ataataatgg caaactctac gccttttatt ttaaattaga ttggtgtgat     120
ttgatgctga cgggagtgag agtaatggcc ttatcctgct gcaggctgtg ctgaggatgg     180
cctggtctgc caccctcctc gagtagcatt ttgcatgtgt aacagggtct cccctctggg     240
gcacaacaac aaagagaagt tgctaaggac aagaagcagg tgcggaaatg catctcccat     300
tggaacagcc ctgggcttac tccaatggct gagagaggtg ctatggccag tcctcccaga     360
gctctgcagc tgcacttggg ggtggacagt ctcgtgcttg tcctgcgtga taacggccgt     420
gaaagccagc caactgctgc ccaaaatcac ccagccgatt gggggtttcc catcggcgca     480
ccctgcccgg agccaagaag acaggctggt gctgctgtat ttgtatttat atccattgct     540
gcgctctgcg ttctcgtggc acgcctggac actcctccgc ctccccctcc tcttcctcct     600
ccagggccac ctccccgcct tccccacccc catctgcttc tgtcaaatga gaaagtcacc     660
gaggagaacc caaacactcc agccgctgag agccccattt ggcacttggc agcacgcggc     720
ggcgggctcc tcggctcaac ttcgaggagt ctccgcgacg caacttttgg ggacgctttg     780
catttaagag agaacgaccg aggaggagga gcgctctgcc cggccgccgc tacctgcggg     840
gagctcacca gcaaacgcca ctgcagacga aggacccaaa gaacgtaaag ggcaaactgc     900
cgccgcgggg aggggcacc gccgagaagt tagagtgtcc cagagacaac ctgctcgagc     960
gctcggccgg agacactaag gcggcccggg gcgcggcgtg gccctggctg gtcccccagc    1020
cccctcctcc ggggcgggag cgacgccggg gcgcgacgag ccccggccgg ccgagcgggt    1080
ctccgcgggc agccaacatt gatttcctcc gggccgaggg cgagggcccg ggcggcggcg    1140
ggctgcagcc gcggcagggc gagagcatgt ccaagccggt ggaccacgtc aagcggccca    1200
tgaacgcctt catggtgtgg tcgcgggctc agcggcgcaa gatggcccag agaaccccca    1260
agatgcacaa ctcggagatc agcaagcgct gggcgccga gtggaaactg ctcacagagt    1320
cggagaagcg gccgttcatc gacgaggcca agcgtctacg cgccatgcac atgaaggagc    1380
accccgacta caagtaccgg ccgcggcgca agcccaagac gctcctcaag aaggacaagt    1440
tcgccttccc ggtgccctac ggcctggcg cgtggcgga cgccgagcac cctgcgctca    1500
aggcgggcgc cgggctgcac gcggggcgg gcggcggcct ggtgcctgag tcgctgctcg    1560
ccaatcccga aaggcggcc gcggccgccg ccgctgccgc cgcacgcgtc ttcttcccgc    1620
agtcggccgc tgccgccgcc gctgccgccg ccgccgccgc cgcgggcagc ccctactcgc    1680
```

-continued

```
tgctcgacct gggctccaaa atggcagaga tctcgtcgtc ctcgtccggc ctcccgtacg    1740
cgtcgtcgct gggctacccg accgcgggcg cgggcgcctt ccacggcgcg cggcggcgg    1800
ctgcagcggc ggccgccgcc gccgggggc acacgcactc gcaccccagc ccgggcaacc    1860
cgggctacat gatcccgtgc aactgcagcg cgtggcccag ccccgggctg cagccgccgc    1920
tcgcctacat cctgctgccg ggcatgggca agccccagct ggaccectac cccgcggcct    1980
acgctgccgc gctatgaccc cgcggggccg cctcgcgagg accggtgtgc acacgtgtac    2040
atatgtatag gtacgagcgc tgcggcctcc ccgtgcgccc tcccgcgacc ggggccggg    2100
tttgtatgta catagaatgt ataggtgcca ggtagaggca gagaggccag gcggggcagg    2160
agtggccaag cgcgcaaggg cgcgggcgag caggcctgtg aattcgcagg atcatttcag    2220
acccgcactt cggcagccaa ctcgaaagca ggcggttgtg tgcggcagca gttggcgttt    2280
gctttgcact tcggaacctg ttgcgttttg acccacggag gtggaggagt aacttttga    2340
catgttggcc tttccagttt tgttggaagt ttcatggtcg gttttgtttt tgtttctcat    2400
tcttcttcct cgcccctcag ccccccaacc cccaaccccc tcccggtccg tgttgcatgc    2460
acgctgttca aatgtgaggt ctgaaatggc tggcacacgg gaaaagctgc ttgtgtcatt    2520
cgttctggg agtgggatgg ctctgagcag cctcgcctcc ctgtttgtac tatttgaact    2580
ttgcagatct ctgttctctc aagcagaact cccaaccaga tccattcttg accagtgacc    2640
ggctcgaatc tggccttttg tgtgagatga tcacggnttc ttttgtttat cacgccattt    2700
gcaaatcaga gcaagagctc tttctcaagg gcaagaaacg caaacaagaa atatttgtga    2760
gatgaaagtt gtcaattgga ttttcttcct aaacaaacaa caacaacaaa ctactagaag    2820
tctccctgag tccactcgct tggatttctg acacagttta caaaaaagga aaaaggcact    2880
gctcctattt tcccttatgg ctgagttcac cttaagattg taaatgtgta tatgtcagtg    2940
aaaacattga ggcttggaaa atgtgttatt ttcgttgccc taagtttgag tcgactttag    3000
actcaaaaac attttgagcg aatatcaaag ttaactttta aaaattgcga aactatttca    3060
gaatcgcaat tttatcgaag attaaatcag acttttttgt ctggtaatta tatatttatt    3120
atttagcaaa actgaagaaa aaagcacag aattgtttca acagatgtct ctcatttca    3180
gctagcattt ctctcccaag ttgagctggt ttaatgtgtt ttggatttcc ctcctcaatt    3240
ggcttatttt ttagatcacc tgcaattcat ttgcaaattg caataaaaca catttagaa    3300
aaaaggaacc ttcaattatt agctttgttt ctttttaaat gtatatattt tgactaatgt    3360
ttgtgaatga agttggctaa catgtattta gtttcatttt ggctttatgt aatataaagt    3420
ttttaaaatt ttaaatatgg ttttaacctt tatgtgtaaa tgattttcta gtgtgacctt    3480
ctaatttaat attagacgtc taaggtatat ctgtaaatta gaatccgact atcactctgt    3540
tcatttttt tgaacaaaga gttttaaataa agcctgaacc agggaaaaga aaatcttct    3600
atttcttgtt gagttcctaa caagatttttt atctgaattg cccttacgtg cctggtccag    3660
gtgaagtgta aggtatcctc caaaggcacc ctttgtttca cttttgaata gatttactag    3720
gaaatctaaa tcaagccatt gttattcaga gccaaaaacc tgatttatca cattttaat    3780
cgtgaatagg aaagaagatt tttaaaaagc ccaagtcgtt gtattagctt taacaacaac    3840
aaaaaaaagg cattcatgaa ccagtagaac agagcccatt gaaaacatcc agacctttca    3900
aagcatttca ccagtttcta gtaacatttt aagaggggaa agttgcttga ccactttatc    3960
ttgttagttg aagagcccca ccacttaaat cagtgtaatt tgttctccta tctttggggt    4020
```

```
attccttgtt gacaccttaa ggttttattt ggaaggataa tcactactaa cgacaaagta    4080
caaattttgg cctctttagg acttaatttt gttatgctaa tcgcattaaa gtagaagtat    4140
aacattcaaa tggagagggt tggatttcta gggctagaca aattgctact aaagtttgaa    4200
aaatcataaa ggattttaat tttagacaag aaatagaaga ctgtcagaaa aaaaaaaata    4260
ggaagatctc gccccccgc aaccaaaatg gaaattctca agatactata tacaagtctt    4320
aaaccagttt ccccattgag accatctctg gagctgcacg tctttataaa cgacccaagt    4380
ctttaaagtc attgttttcc cccaacggaa taatatttta aaaaccatga aaagttttgg    4440
aaatgtgaga ataggctct gctggtttga ccctgattca ctaattaaaa tgatccctct    4500
cctgttattc cctgagctct ttgcaatatt ataagttaat tcatatggtt ctgagcgatt    4560
atgcaaaact aatttggact gtccaggggt aattatccct gacacggtta attaaatcct    4620
ttcaaggctt cgtctttccc ttttgtagca gcccatccct tctcaacacg gaacttctgc    4680
ggctcgctgg aaatcacccc agccctaaat cttagttacc ccctgagcc ttccagctcg    4740 gccgcctcct cggcctgaag actccccgcc tcctcccgcc ccctccccctt ttcccaaaga    4800 tcagcgtttt ctgggagaaa cgctccggag ttgttgatga atgagaagag gactggaaag    4860
atgggtaaga ggaggggtga ggatgccgag ggggagcacc gaggtcatat cgccaacaga    4920
ttgtgcggct gtttgaggac ctccacaggc cccacagact cgtttatcac ccattctgac    4980
tccaatggtc ttgctaacaa gttggcgggt tttgcgcctg cagagagcct cctgccaagt    5040
tagactgtgc agaagtaagg ggttggagcg ggggagcgg ctccggggca agagggcgta    5100
gagaaaggcc cggggnnggg nggtgtaagc gtctgaaagt ggcccacaaa tgcagcgctg    5160
tgattgggca gagagctgct gctggctcgc gatctctatc tccatctctt tatctatctc    5220
cgtctctctc cctgtttctc catttttctt tctttccttc tctctccttc cttccttcca    5280
tctttcttct ttcccttcct tttattcttc tattttcgtt tcttttcaag gttttttta    5340 aagccatgat gcaatttctt tggtattcac cgttgtccca aaacttgaag caagcctcgt    5400
atccaagggg ccaggcatgt tgcttcgggc tttgtgcaaa caggtggaat tgcgctgtgt    5460
aagcagtaag aactggtgct ggggagctgt cgcgcgaggg ggtggctttg ggagagcagg    5520
gttgctggcc gcgattgtta cttcccttga caatttcctc ctcccctcc cccaagaaga    5580 taggagaaag caccgcggat ctccctctca ccccaggctc ggggcgcaga agatggagag    5640
aagattccac tctccccgga gcagataggg acggtcgcgc cagccaatca gagcgcggct    5700
cggcgccggc gctcccggcc gcctgggccg ccgtgtcctc caggcaagcg aagttcccgc    5760
aactcgtccg cctcgaggt ccgcgtcttt cttgcgcccg cggcccagcg gaggccgagg    5820
gagccgtcca aactttatta atctctcctc ctttctttct ccctcagccc agtgcatctc    5880
aaaggtcagc cctcttcttt taaaagactg atattattaa tgcactgaca attcctcccc    5940
cccttttctt ttttctctct tgcagggggg aaaaaaggg aaatggtgaa aagagctttt    6000
tttatccttt ttttttttt gtccttcagt gggagcgttt agacagtcga ggaggttttg    6060
tccgagaaca aaacgcaggg ttgggaggtt ttgtgagagt gttgtttgtt gaagtggagc    6120
taagaaaaag cggcggcttt ctcctcattg tgaagaaacc aatcagtggt atttggaaaa    6180
ctgttagcat tgtgcacttc ttctgtgtcc attgtgaggc gtttcttttc acaaggtttt    6240
tttttcagcc gatccagctg gccggaatga atagcggtgc aatgtgtaca cgctttgtcc    6300
ctccggcctt caagtagccc ccattgaata gactaagttg acctgcgtga cagtgaaaca    6360
acataataaa aaatacatga gcccctgaat aggagcaggc gcataaataa ataaaatggg    6420
```

```
tgaccaaaac tggataaact gaatgacaaa acggtgaaag gggaacaaaa agatatttaa   6480
cacgctagat tagcattaga atgcgatcta caaggcagaa caattgatga ataggtttac   6540
cggccaagaa agaaatggac taaatgccct ttgaatagat atgctttttg caagggcttt   6600
gaatagatat gcttttgcaa gggctgaatg ggaaaaggta agatgaagc tatgcaaatg    6660 agccggggaa cttttatat atattcttta aacacacaca cacactgcgg ggggaagagt    6720
gctgcctcgg gatgtttata gaagcaataa ttgccattat tagcattgtc tgcggcagat   6780
agaaattgaa caggttggga taatataggg tagcagtaat tattcttcta attaatggtc   6840
ctttgctact tgaaaaaaga aaaaggaaa gaagtagtaa aagttatgca gaagttatgt     6900
ttccttgtgt ccatttgccc agcgctgaaa tctgtggagc aggaagcctg gcaattccaa   6960
gatacgcgat gatcytcaaa cattcccggg agccagtcct gaggctctgg cttcagggcc   7020
tagtttccat ttatgccgcg ttttttgagag tctaatactg tgtctggcac atggtaggtg  7080
ctcactgaat agtcgtggta tgaatgaatg aacgaatgaa tgaatgaatg aatgaatata   7140
agtttaatgg gggaaacccg ggcctcctaa taaaggtagg ggctggggga tacctagggg   7200
cttccccagg aggatttctt ttttcatcat cccaccctg ggagaaaggt ccacgcagga    7260
tggtcgcttc cccttgctg agagtttttgc cttcagccta tctgggccgc tggaaaagag   7320
gagaagaata aacaagagac aagcaactac tccctaccg gcgttccgtc cttgtcctca    7380
ctgccaaatc cactccaaag ccgaggatgg tgagactgtg aagttgcaaa gaaacagag    7440 gcccaccccc ttaaagaatt acgatatatt taaagtttgc ctctttcagg tttctctcct   7500
tggctcctgc cccttttcccc tcccggctcc ttgtccttga ctgaacctca tgggacagag  7560
aacctcctgt cccccacgag gcaaggcgcg aacccgcaga gatctggggt gccctttggt   7620
tccctgcgct gccctggagg cgtccataga ggcctttgcc gccaaggaca gcaattgttt   7680
tattttcgat ggttgctcgc caggctgcgg gtcgcgggcc cacccagccg tcgaactttc   7740
cagtcgttat cagcgctgct cctaacttaa tggaataatg caaattatag cctgcccagc   7800
tgacacgtcc ctgcgaatgc gccggggctg agctctggcc agccgctctc tcgacgtcct   7860
ggacggccgg agggaatgaa gctctgaatt gtgacaaaag tggggggggc accccaaatt   7920
ctcaaagcaa tgttcttttt ttttcttt tccttaagca attgagcctt accaaatgtc     7980
ggggccggcc gcacggaagc cttgcatatt ttaaagtgta acctgagcct tcgcggtttc   8040
agcttcactt aaaacatgca aattcttgaa attgaaaaat ctgaaaaact tccgaagagt   8100
tctatctgaa taaatccaaa tccattggga gtcgctttga ggagacaaaa cgcacagcga   8160
tttggggtga gggatatttg tgggggaggca ggacgtgctg gattgggttt ccagggtcaa  8220
ggtgtctctg ggccttcgac gatagcctta gcgcagagca gggaagtggc accgctaggc   8280
agcaagctca gttgctctac ttttgtgacc catcccccca ccccccccac cgccacccttt  8340 gcctccgggc cactgcccct ctctgcaagc tt                                  8372
```

<210> SEQ ID NO 13
<211> LENGTH: 4877
<212> TYPE: DNA
<213> ORGANISM: Homo sapiens

<400> SEQUENCE: 13

```
gcccgaaacc cggaagtgag cggcggcagc tgcgaggctc ggagaaacag gcgccgcggg    60
ctccgcgccc ggccggaccc gggcccgaga tcatgatgct gccgccaccg ccgccaccac   120
```

-continued

```
ggagcgagaa gcccagatag acgccccggc ggccccgggt cctggagtcc cgccgcctgc      180
tgcccggccg aggaccccac cccgcctgcc gcccgatgct tgcagtgggg cccgccatgg      240
acagggatta cccgcagcat gaaccccgc cggcgggcag cctcctgtac agcccgccgc       300
ccctgcagag cgccatgctg cactgcccct actggaacac cttctcgctg ccgccatacc     360
ctgccttctc cagcgacagc cgcccgttca tgagctccgc ctccttcctc ggcagccagc     420
cctgcccaga caccagctat gccccgtgg ccaccgcctc cagcttgcca ccaaagacct      480
gcgactttgc tcaggactcc tcctattttg aggacttctc caacatctcc atcttctcct    540
cgtccgtgga ctccctgtcg acatcgtgg acacgcccga cttcctgccg gctgacagcc     600
tcaaccaggt gtccaccatc tgggacgata accctgcccc ctccaccac gataagctgt     660 tccagctcag caggccgttt gcaggcttcg aggactttct gccctcccac agcaccccgc    720
ttctcgtcag ctaccaggag cagagtgtgc agagccagcc agaggaggag gacgaggctg    780
aggaggagga ggcggaggag ctggggcaca cagagaccta cgccgactac gtgccgtcca    840
agtccaagat cgggaagcag cacccagacc gcgtggtgga gaccagcaca ctgtccagcg    900
tcccaccccc agacatcacc tacacccctg ccctgccctc ggacagcggg gccctgtctg    960
ccctgcagct agaggccatc acctacgcct gccagcaaca cgaggtcctg ctccccagcg   1020
ggcagcgcgc gggctttctc atcggcgatg gggccggcgt gggcaaaggc cggacggtgg   1080
ccggagtcat cctggagaac cacctgcgcg ccggaagaa agcattgtgg ttcagcgtct    1140
ccaacgacct caagtacgat gcggagcgcg acctgcggga catcgaagcc acgggcatcg   1200
cggtgcacgc gctcagcaag atcaagtacg gtgacaccac tacctcagag ggcgtcctct   1260
tcgccaccta ctccgccctg attggggaga gccaggccgg tggccagcac cgcactcgcc   1320
tccggcagat cctggactgg tgtggggagg cctttgaggg cgtcatcgtg ttcgacgagt   1380
gtcacaaagc caagaatgcc ggctccacca agatgggcaa ggccgtgcta gacctgcaga   1440
acaagctgcc cctggcccgc gtggtctacg ccagcgccac aggtgcctct gagcctcgga   1500
acatgatcta catgagccgc ttgggtatct ggggcgaggg cacacccttc cggaactttg   1560
aggagttcct gcacgccatc gagaagaggg gcgttggcgc catggagatc gtggccatgg   1620
acatgaaggt cagcggcatg tacatcgcac gccagctcag cttctccggc gtcaccttcc   1680
gcatcgagga gatcccgctg gccccagcct tcgagtgcgt ctacaaccgc gcagccctgc   1740
tgtgggccga ggccctgaac gtgttccagc aggcggccga ctggatcggc ctggagtcgc   1800
gcaagtccct gtggggccag ttctggtcgg cacaccagcg cttcttcaag tatctgtgca   1860
tcgcagccaa ggtgcgccgg ctggtggagc tgcccgaga ggagctggcg cgagacaagt    1920
gcgtggtcat cgggctgcag tccacgggcg aggcgcgcac gcgggaggtg ctgggggaga   1980
acgatgggca cctcaactgc ttcgtctcgg ccgctgaagg cgtgttcctg tcgctaattc    2040
agaagcactt tccgtccacc aagagaaagc gggacagagg agcgggcagc aagcggaaac   2100
ggcgacctcg gggacgcggg gccaaagccc ccggctggc gtgcgagaca gcgggcgtca    2160
tccgcatcag tgacgacagc agcacggagt cggaccctgg cctggacagc gacttcaact   2220
cctcccccga gtccctggtg gatgacgacg ttgtcatcgt tgatgcagtc gggctcccca   2280
gtgacgaccg gggatccctg tgcctcctgc agagagaccc gcatggcccc gggtcctgg    2340 agcgggtgga gcggctgaag caggatctgc tggacaaagt gcgccggctg gccgggaac    2400 tgccagtcaa caccctggac gagctcatcg accagctggg cggcccccag cggtggcgg    2460 agatgaccgg caggaaaggc cgcgtggtgt ccaggcccga cgggacggtg gccttcgagt   2520
```

-continued

| | |
|---|---|
| cgcgggcaga gcagggtctg tccatcgacc acgtgaacct cagggagaag cagcgcttca | 2580 |
| tgagcggcga gaagctcgtg gccatcatct cggaggcctc cagctcgggt gtctccctcc | 2640 |
| aagccgaccg ccgtgtccag aaccagcggc gccgcgtgca catgaccttg gagctgccgt | 2700 |
| ggagcgccga ccgcgccatc agcagttcg gccgcaccca ccggtccaac caggtctccg | 2760 |
| cgccagagta tgtcttcctc atctcggagc tggccgggga gcgccggttc gcctccatcg | 2820 |
| tggccaagcg cctggagagt ctgggggccc tgacccacgg agaccgccgc gccacggagt | 2880 |
| cccgtgacct cagcaagtac aactttgaga caagtatgg cacccgggcc ctgcactgtg | 2940 |
| tcctcaccac catcctgagc cagactgaga acaaagtgcc tgtgcccag ggatacctg | 3000 |
| gaggggtccc caccttcttc cgggacatga agcagggcct gctgtctgtg ggcattggtg | 3060 |
| gccgggagtc ccggaatggc tgcctggacg tggagaagga ctgttccatc accaagttcc | 3120 |
| tgaaccgcat cctggggctg gaggtgcaca agcagaatgc cctgttccag tacttctcag | 3180 |
| acaccttcga ccacctcatc gagatggaca agcgggaggg caaatacgac atgggcatcc | 3240 |
| tggaccttgc tcccggtatc gaggagatct acgaggagag ccagcaggtg ttcctggctc | 3300 |
| ccgggcaccc gcaggacggg caggtggtct tctacaagat cagcgtggac cgcggcctga | 3360 |
| agtgggagga cgcctttgcc aagtcgctgg cgctgacggg ccctatgac ggcttctacc | 3420 |
| tctcctacaa ggtccgcggt aacaagccca gctgcctgct ggcggagcag aaccgcggcc | 3480 |
| agttcttcac ggtgtacaag cccaacatcg gccggcagag ccagctggag gccctggaca | 3540 |
| gcctccgccg caagttccac cgggtcaccg cggaggaggc caaggagccc tgggagagtg | 3600 |
| gctacgcttt gtcgctgacg cactgcagcc acagcgcctg gaaccggcac tgccggctgg | 3660 |
| cgcaggaggg taaggactgc ctgcaggggc tgcggctgcg gcaccactac atgctgtgcg | 3720 |
| gcgcgctgct gcgcgtgtgg ggccgcatcg ccgccgtcat ggccgacgtc agcagcagca | 3780 |
| gctacctgca gatcgtgcgg ctgaagacca aggacaggaa gaagcaagtg ggcatcaaga | 3840 |
| tccccgaggg ctgcgtgcgc cgggtgctgc aggagctgcg gctgatggat gcggacgtga | 3900 |
| agcgcaggca ggcgcccgcc ctgggctgcc ccgccccgcc cgccccgcgc cgctggcgc | 3960 |
| tgccttgcgg ccccggagag gtgctggacc tcacctacag ccccccggcc gaggccttcc | 4020 |
| cgccgccccc gcacttctct ttcccggcgc cgctgtccct ggacgccggc cccggcgtcg | 4080 |
| tgccgctggg caccccgac gcccaggccg accctgcggc cctcgcgcac cagggctgcg | 4140 |
| acatcaactt caaggaggtg ctggaggaca tgctgcgctc gctgcacgcg gggccgccct | 4200 |
| ccgagggcgc gctgggggag ggcgcgggg cgggggcgc ggcgggcggt ggtcccgagc | 4260 |
| ggcagagcgt gatccagttc agcccaccct tccccggcgc ccaggctcct ctctgacacg | 4320 |
| cctttaggcg aaacatgccc caagacacag ggaccgtttc tcccctagga gcagcggtgg | 4380 |
| ggagcagggc caagtccccc tgaccactgc tcagaggagc cctaggccct ggccgcagtg | 4440 |
| ccttcagcgc ccgacccggg cccccacctg gtcagccctg gcggggccca ctcaggacag | 4500 |
| ctggggggccg gggcgtggca gggccctctc tgtgcctctc ctcctaagta ggaagggggct | 4560 |
| ccgggtggct gctctgggac tgggcaccca caagggctca gtgggcccaa acccttgaaa | 4620 |
| tccgtgaaac cgggtggtcc caagagctag aaactcagga acccccaggt gctcagggcc | 4680 |
| ccgcgtctcg ggggctccgt ggggcagacc cctgctaata tatgcaattc tccctcccc | 4740 |
| agcccttccc tgacccctaa gttattgccc gctcacctct cccaggcccc aggccgcgga | 4800 |
| gctggcaggg tggcgcctgc ggtttctatg tatttatagc aagttctgat gtacatatgt | 4860 |

-continued

| | |
|---|---|
| aaaggacttt tttaaat | 4877 |

<210> SEQ ID NO 14
<211> LENGTH: 1872
<212> TYPE: DNA
<213> ORGANISM: Homo sapiens

<400> SEQUENCE: 14

| | |
|---|---|
| tcaggctgcc tgatctgccc agctttccag ctttcctctg gattccggcc tctggtcatc | 60 |
| cctccccacc ctctctccaa ggccctctcc tggtctccct tcttctagaa cccttcctc | 120 |
| cacctccctc tctgcagaac ttctccttta cccccaccc ccaccactg cccccttcc | 180 |
| ttttctgacc tccttttgga gggctcagcg ctgcccagac cataggagag atgtgggagg | 240 |
| ctcagttcct gggcttgctg tttctgcagc cgctttgggt ggctccagtg aagcctctcc | 300 |
| agccaggggc tgaggtcccg gtggtgtggg cccaggaggg ggctcctgcc cagctcccct | 360 |
| gcagccccac aatccccctc caggatctca gccttctgcg aagagcaggg gtcacttggc | 420 |
| agcatcagcc agacagtggc ccgcccgctg ccgcccccgg ccatcccctg gccccggcc | 480 |
| ctcacccggc ggcgccctcc tcctgggggc ccaggccccg ccgctacacg gtgctgagcg | 540 |
| tgggtcccgg aggcctgcgc agcgggaggc tgccctgca gccccgcgtc cagctggatg | 600 |
| agcgcggccg gcagcgcggg gacttctcgc tatggctgcg cccagcccgg cgcgcggacg | 660 |
| ccggcgagta ccgcgccgcg gtgcacctca gggaccgcgc cctctcctgc cgcctccgtc | 720 |
| tgcgcctggg ccaggcctcg atgactgcca gccccccagg atctctcaga gcctccgact | 780 |
| gggtcatttt gaactgctcc ttcagccgcc ctgaccgccc agcctctgtg cattggttcc | 840 |
| ggaaccgggg ccagggccga gtccctgtcc gggagtcccc ccatcaccac ttagcggaaa | 900 |
| gcttcctctt cctgccccaa gtcagcccca tggactctgg gccctgggc tgcatcctca | 960 |
| cctacagaga tggcttcaac gtctccatca tgtataacct cactgttctg ggtctggagc | 1020 |
| ccccaactcc cttgacagtg tacgctggag caggttccag ggtggggctg ccctgccgcc | 1080 |
| tgcctgctgg tgtggggacc cggtctttcc tcactgccaa gtggactcct cctgggggag | 1140 |
| gccctgacct cctggtgact ggagacaatg gcgactttac ccttcgacta gaggatgtga | 1200 |
| gccaggccca ggctgggacc tacacctgcc atatccatct gcaggaacag cagctcaatg | 1260 |
| ccactgtcac attggcaatc atcacagtga ctcccaaatc ctttgggtca cctggatccc | 1320 |
| tggggaagct gctttgtgag gtgactccag tatctggaca agaacgcttt gtgtggagct | 1380 |
| ctctggacac cccatcccag aggagtttct caggaccttg gctggaggca caggaggccc | 1440 |
| agctcctttc ccagccttgg caatgccagc tgtaccaggg ggagaggctt cttggagcag | 1500 |
| cagtgtactt cacagagctg tctagcccag gtgcccaacg ctctgggaga gccccaggtg | 1560 |
| ccctcccagc aggccacctc ctgctgtttc tcacccttgg tgtcctttct ctgctccttt | 1620 |
| tggtgactgg agcctttggc tttcaccttt ggagaagaca gtggcgacca agacgatttt | 1680 |
| ctgccttaga gcaagggatt caccctcgcc aggctcagag caagatagag gagctggagc | 1740 |
| aagaaccgga gccggagccg gagccggaac cggagcccga gcccgagccc gagccggagc | 1800 |
| agctctgacc tggagctgag gcagccagca gatctcagca gcccagtcca aataaacgtc | 1860 |
| ctgtctagca gc | 1872 |

<210> SEQ ID NO 15
<211> LENGTH: 1201
<212> TYPE: DNA
<213> ORGANISM: Homo sapiens -continued

```
<220> FEATURE:
<221> NAME/KEY: Unsure
<222> LOCATION: (697)..(698)
<223> OTHER INFORMATION: n = a, c, g or t
<220> FEATURE:
<221> NAME/KEY: Unsure
<222> LOCATION: (715)..(715)
<223> OTHER INFORMATION: n = a, c, g or t
<220> FEATURE:
<221> NAME/KEY: Unsure
<222> LOCATION: (764)..(764)
<223> OTHER INFORMATION: n = a, c, g or t
<220> FEATURE:
<221> NAME/KEY: Unsure
<222> LOCATION: (772)..(772)
<223> OTHER INFORMATION: n = a, c, g or t
<220> FEATURE:
<221> NAME/KEY: Unsure
<222> LOCATION: (782)..(782)
<223> OTHER INFORMATION: n = a, c, g or t
<220> FEATURE:
<221> NAME/KEY: Unsure
<222> LOCATION: (835)..(835)
<223> OTHER INFORMATION: n = a, c, g or t
<220> FEATURE:
<221> NAME/KEY: Unsure
<222> LOCATION: (849)..(849)
<223> OTHER INFORMATION: n = a, c, g or t
<220> FEATURE:
<221> NAME/KEY: Unsure
<222> LOCATION: (880)..(880)
<223> OTHER INFORMATION: n = a, c, g or t
<220> FEATURE:
<221> NAME/KEY: Unsure
<222> LOCATION: (886)..(886)
<223> OTHER INFORMATION: n = a, c, g or t
<220> FEATURE:
<221> NAME/KEY: Unsure
<222> LOCATION: (931)..(931)
<223> OTHER INFORMATION: n = a, c, g or t
<220> FEATURE:
<221> NAME/KEY: Unsure
<222> LOCATION: (935)..(935)
<223> OTHER INFORMATION: n = a, c, g or t
<220> FEATURE:
<221> NAME/KEY: Unsure
<222> LOCATION: (944)..(944)
<223> OTHER INFORMATION: n = a, c, g or t
<220> FEATURE:
<221> NAME/KEY: Unsure
<222> LOCATION: (950)..(950)
<223> OTHER INFORMATION: n = a, c, g or t
<220> FEATURE:
<221> NAME/KEY: Unsure
<222> LOCATION: (966)..(966)
<223> OTHER INFORMATION: n = a, c, g or t
<220> FEATURE:
<221> NAME/KEY: Unsure
<222> LOCATION: (976)..(976)
<223> OTHER INFORMATION: n = a, c, g or t
<220> FEATURE:
<221> NAME/KEY: Unsure
<222> LOCATION: (983)..(983)
<223> OTHER INFORMATION: n = a, c, g or t
<220> FEATURE:
<221> NAME/KEY: Unsure
<222> LOCATION: (988)..(988)
<223> OTHER INFORMATION: n = a, c, g or t
<220> FEATURE:
<221> NAME/KEY: Unsure
<222> LOCATION: (1014)..(1014)
<223> OTHER INFORMATION: n = a, c, g or t
<220> FEATURE:
<221> NAME/KEY: Unsure
<222> LOCATION: (1053)..(1054)
<223> OTHER INFORMATION: n = a, c, g or t
<220> FEATURE:
<221> NAME/KEY: Unsure
<222> LOCATION: (1061)..(1061)
```

```
<223> OTHER INFORMATION: n = a, c, g or t
<220> FEATURE:
<221> NAME/KEY: Unsure
<222> LOCATION: (1066)..(1066)
<223> OTHER INFORMATION: n = a, c, g or t
<220> FEATURE:
<221> NAME/KEY: Unsure
<222> LOCATION: (1076)..(1076)
<223> OTHER INFORMATION: n = a, c, g or t
<220> FEATURE:
<221> NAME/KEY: Unsure
<222> LOCATION: (1093)..(1093)
<223> OTHER INFORMATION: n = a, c, g or t
<220> FEATURE:
<221> NAME/KEY: Unsure
<222> LOCATION: (1100)..(1100)
<223> OTHER INFORMATION: n = a, c, g or t
<220> FEATURE:
<221> NAME/KEY: Unsure
<222> LOCATION: (1104)..(1104)
<223> OTHER INFORMATION: n = a, c, g or t
<220> FEATURE:
<221> NAME/KEY: Unsure
<222> LOCATION: (1104)..(1104)
<223> OTHER INFORMATION: n = a, c, g or t
<220> FEATURE:
<221> NAME/KEY: Unsure
<222> LOCATION: (1115)..(1115)
<223> OTHER INFORMATION: n = a, c, g or t
<220> FEATURE:
<221> NAME/KEY: Unsure
<222> LOCATION: (1121)..(1121)
<223> OTHER INFORMATION: n = a, c, g or t
<220> FEATURE:
<221> NAME/KEY: Unsure
<222> LOCATION: (1129)..(1129)
<223> OTHER INFORMATION: n = a, c, g or t
<220> FEATURE:
<221> NAME/KEY: Unsure
<222> LOCATION: (1134)..(1135)
<223> OTHER INFORMATION: n = a, c, g or t
<220> FEATURE:
<221> NAME/KEY: Unsure
<222> LOCATION: (1144)..(1144)
<223> OTHER INFORMATION: n = a, c, g or t
<220> FEATURE:
<221> NAME/KEY: Unsure
<222> LOCATION: (1149)..(1149)
<223> OTHER INFORMATION: n = a, c, g or t
<220> FEATURE:
<221> NAME/KEY: Unsure
<222> LOCATION: (1153)..(1153)
<223> OTHER INFORMATION: n = a, c, g or t
<220> FEATURE:
<221> NAME/KEY: Unsure
<222> LOCATION: (1169)..(1169)
<223> OTHER INFORMATION: n = a, c, g or t
<220> FEATURE:
<221> NAME/KEY: Unsure
<222> LOCATION: (1178)..(1178)
<223> OTHER INFORMATION: n = a, c, g or t
<220> FEATURE:
<221> NAME/KEY: Unsure
<222> LOCATION: (1182)..(1182)
<223> OTHER INFORMATION: n = a, c, g or t
<220> FEATURE:
<221> NAME/KEY: Unsure
<222> LOCATION: (1193)..(1193)
<223> OTHER INFORMATION: n = a, c, g or t

<400> SEQUENCE: 15
gagtctacgg cattgctgag gacgctgccc agggcatcgc taatgaggac gccgaccagg      60
gcatcgctaa tgaggacacc acccagtgca tcgccaacga ggaagccgcc cagggcatcg     120
ccgaggacgc catccagggc atcgccaacg aggaggttgc ccagggcatc gccaatgggg     180
tcgccgcaca gggcatcgcc aatgaggacg ccacccaggg catcgccaac tgggacgccg     240
```

-continued

```
tccacggctt cgccaacggg gacgccgtcc tcagcttcgc caacggggac gccgcccagg    300
gcatcgccaa cggggacgcc accaagggca tgggcaacga ggtcaccatc acggcatcg    360 ctaacgagga cgccgtccag ggcatcgcta acgaggtggc cgcccagggc atcgccaacg    420
aggacgccgc ccagggaatc gccgaggatg tcgcacaggg catcgccaac gaggacgccg    480
cccagggcat cgccaacaag gaggccgccc agggcatcgc caacgaggac gccgcccagg    540
gaatcgctga ggacgtcgca cagggcatcg ccaacgagga tgccgcccag ggcatcgcca    600
acgaggaggc cgcccagggc atcgccaaca gggtcgccgc ccagggcatc gccaatgacg    660
ccacccaggg catcgccgag gacaccgcca ggctttnnca acgacgaacg ccgtncaagg    720
cattggttaa cgaggacgcc gtcttgggca ttggccaacg aacnacgccg tncaaggcat    780
tngnttaatg aaaaaatgga gttccaccgg tattcgaata accaaggaca cccgnccaag    840
ggcattggnc naactgggga cttccgtcca agggcctttn cccaaggggg acccccgcc    900 caagggccct cctttaatgg gggtcgnccg nccangggcc tttntttacn ggggacccc    960 tccaangggc atttttntttt ttngggngcc cccccccaag gggttcccctt tganggggaa   1020 gttttttccac gggatttttt taaaagggga ccnncttccc ngggcntttt ttttanaaag   1080
gacccattcc aantttttgn ttgnaaaggg acccnttcct ngggtttant aaanngggac   1140
cccncccang ggntttatta aattggaanc cccccangg gntttttttta ttnggacccc   1200 c                                                                   1201
```

<210> SEQ ID NO 16
<211> LENGTH: 748
<212> TYPE: DNA
<213> ORGANISM: Homo sapiens
<220> FEATURE:
<221> NAME/KEY: Unsure
<222> LOCATION: (697)..(698)
<223> OTHER INFORMATION: n = a, c, g or t
<220> FEATURE:
<221> NAME/KEY: Unsure
<222> LOCATION: (715)..(715)
<223> OTHER INFORMATION: n = a, c, g or t

<400> SEQUENCE: 16

```
gagtctacgg cattgctgag gacgctgccc agggcatcgc taatgaggac gccgaccagg    60
gcatcgctaa tgaggacacc acccagtgca tcgccaacga ggaagccgcc cagggcatcg   120
ccgaggacgc catccagggc atcgccaacg aggaggttgc ccagggcatc gccaatgggg   180
tcgccgcaca gggcatcgcc aatgaggacg ccacccaggg catcgccaac tgggacgccg   240
tccacggctt cgccaacggg gacgccgtcc tcagcttcgc caacggggac gccgcccagg   300
gcatcgccaa cggggacgcc accaagggca tgggcaacga ggtcaccatc acggcatcg    360 ctaacgagga cgccgtccag ggcatcgcta acgaggtggc cgcccagggc atcgccaacg   420
aggacgccgc ccagggaatc gccgaggatg tcgcacaggg catcgccaac gaggacgccg   480
cccagggcat cgccaacaag gaggccgccc agggcatcgc caacgaggac gccgcccagg   540
gaatcgctga ggacgtcgca cagggcatcg ccaacgagga tgccgcccag ggcatcgcca   600
acgaggaggc cgcccagggc atcgccaaca gggtcgccgc ccagggcatc gccaatgacg   660
ccacccaggg catcgccgag gacaccgcca ggctttnnca acgacgaacg ccgtncaagg   720
cattggttaa cgaggacgcc gtcttggg                                       748
```

<210> SEQ ID NO 17

```
<211> LENGTH: 1232
<212> TYPE: DNA
<213> ORGANISM: Homo sapiens
<220> FEATURE:
<221> NAME/KEY: Unsure
<222> LOCATION: (214)..(214)
<223> OTHER INFORMATION: n = a, c, g or t
<220> FEATURE:
<221> NAME/KEY: Unsure
<222> LOCATION: (243)..(243)
<223> OTHER INFORMATION: n = a, c, g or t
<220> FEATURE:
<221> NAME/KEY: Unsure
<222> LOCATION: (269)..(269)
<223> OTHER INFORMATION: n = a, c, g or t
<220> FEATURE:
<221> NAME/KEY: Unsure
<222> LOCATION: (291)..(291)
<223> OTHER INFORMATION: n = a, c, g or t
<220> FEATURE:
<221> NAME/KEY: Unsure
<222> LOCATION: (294)..(294)
<223> OTHER INFORMATION: n = a, c, g or t
<220> FEATURE:
<221> NAME/KEY: Unsure
<222> LOCATION: (317)..(317)
<223> OTHER INFORMATION: n = a, c, g or t
<220> FEATURE:
<221> NAME/KEY: Unsure
<222> LOCATION: (334)..(335)
<223> OTHER INFORMATION: n = a, c, g or t
<220> FEATURE:
<221> NAME/KEY: Unsure
<222> LOCATION: (341)..(341)
<223> OTHER INFORMATION: n = a, c, g or t
<220> FEATURE:
<221> NAME/KEY: Unsure
<222> LOCATION: (358)..(358)
<223> OTHER INFORMATION: n = a, c, g or t
<220> FEATURE:
<221> NAME/KEY: Unsure
<222> LOCATION: (379)..(379)
<223> OTHER INFORMATION: n = a, c, g or t
<220> FEATURE:
<221> NAME/KEY: Unsure
<222> LOCATION: (392)..(392)
<223> OTHER INFORMATION: n = a, c, g or t
<220> FEATURE:
<221> NAME/KEY: Unsure
<222> LOCATION: (394)..(395)
<223> OTHER INFORMATION: n = a, c, g or t
<220> FEATURE:
<221> NAME/KEY: Unsure
<222> LOCATION: (405)..(405)
<223> OTHER INFORMATION: n = a, c, g or t
<220> FEATURE:
<221> NAME/KEY: Unsure
<222> LOCATION: (413)..(413)
<223> OTHER INFORMATION: n = a, c, g or t
<220> FEATURE:
<221> NAME/KEY: Unsure
<222> LOCATION: (416)..(416)
<223> OTHER INFORMATION: n = a, c, g or t
<220> FEATURE:
<221> NAME/KEY: Unsure
<222> LOCATION: (418)..(418)
<223> OTHER INFORMATION: n = a, c, g or t
<220> FEATURE:
<221> NAME/KEY: Unsure
<222> LOCATION: (423)..(423)
<223> OTHER INFORMATION: n = a, c, g or t
<220> FEATURE:
<221> NAME/KEY: Unsure
<222> LOCATION: (425)..(425)
<223> OTHER INFORMATION: n = a, c, g or t
<220> FEATURE:
<221> NAME/KEY: Unsure
<222> LOCATION: (429)..(430)
<223> OTHER INFORMATION: n = a, c, g or t
```

-continued

```
<220> FEATURE:
<221> NAME/KEY: Unsure
<222> LOCATION: (434)..(434)
<223> OTHER INFORMATION: n = a, c, g or t
<220> FEATURE:
<221> NAME/KEY: Unsure
<222> LOCATION: (439)..(440)
<223> OTHER INFORMATION: n = a, c, g or t
<220> FEATURE:
<221> NAME/KEY: Unsure
<222> LOCATION: (442)..(442)
<223> OTHER INFORMATION: n = a, c, g or t
<220> FEATURE:
<221> NAME/KEY: Unsure
<222> LOCATION: (446)..(447)
<223> OTHER INFORMATION: n = a, c, g or t
<220> FEATURE:
<221> NAME/KEY: Unsure
<222> LOCATION: (454)..(454)
<223> OTHER INFORMATION: n = a, c, g or t
<220> FEATURE:
<221> NAME/KEY: Unsure
<222> LOCATION: (456)..(456)
<223> OTHER INFORMATION: n = a, c, g or t
<220> FEATURE:
<221> NAME/KEY: Unsure
<222> LOCATION: (459)..(460)
<223> OTHER INFORMATION: n = a, c, g or t
<220> FEATURE:
<221> NAME/KEY: Unsure
<222> LOCATION: (467)..(467)
<223> OTHER INFORMATION: n = a, c, g or t
<220> FEATURE:
<221> NAME/KEY: Unsure
<222> LOCATION: (473)..(474)
<223> OTHER INFORMATION: n = a, c, g or t
<220> FEATURE:
<221> NAME/KEY: Unsure
<222> LOCATION: (485)..(486)
<223> OTHER INFORMATION: n = a, c, g or t
<220> FEATURE:
<221> NAME/KEY: Unsure
<222> LOCATION: (491)..(491)
<223> OTHER INFORMATION: n = a, c, g or t
<220> FEATURE:
<221> NAME/KEY: Unsure
<222> LOCATION: (499)..(500)
<223> OTHER INFORMATION: n = a, c, g or t
<220> FEATURE:
<221> NAME/KEY: Unsure
<222> LOCATION: (502)..(502)
<223> OTHER INFORMATION: n = a, c, g or t
<220> FEATURE:
<221> NAME/KEY: Unsure
<222> LOCATION: (505)..(505)
<223> OTHER INFORMATION: n = a, c, g or t
<220> FEATURE:
<221> NAME/KEY: Unsure
<222> LOCATION: (509)..(509)
<223> OTHER INFORMATION: n = a, c, g or t
<220> FEATURE:
<221> NAME/KEY: Unsure
<222> LOCATION: (513)..(513)
<223> OTHER INFORMATION: n = a, c, g or t
<220> FEATURE:
<221> NAME/KEY: Unsure
<222> LOCATION: (516)..(517)
<223> OTHER INFORMATION: n = a, c, g or t
<220> FEATURE:
<221> NAME/KEY: Unsure
<222> LOCATION: (520)..(520)
<223> OTHER INFORMATION: n = a, c, g or t
<220> FEATURE:
<221> NAME/KEY: Unsure
<222> LOCATION: (525)..(525)
<223> OTHER INFORMATION: n = a, c, g or t
<220> FEATURE:
<221> NAME/KEY: Unsure
<222> LOCATION: (528)..(528)
```

-continued

```
<223> OTHER INFORMATION: n = a, c, g or t
<220> FEATURE:
<221> NAME/KEY: Unsure
<222> LOCATION: (532)..(532)
<223> OTHER INFORMATION: n = a, c, g or t
<220> FEATURE:
<221> NAME/KEY: Unsure
<222> LOCATION: (534)..(534)
<223> OTHER INFORMATION: n = a, c, g or t
<220> FEATURE:
<221> NAME/KEY: Unsure
<222> LOCATION: (537)..(539)
<223> OTHER INFORMATION: n = a, c, g or t
<220> FEATURE:
<221> NAME/KEY: Unsure
<222> LOCATION: (548)..(549)
<223> OTHER INFORMATION: n = a, c, g or t
<220> FEATURE:
<221> NAME/KEY: Unsure
<222> LOCATION: (552)..(552)
<223> OTHER INFORMATION: n = a, c, g or t
<220> FEATURE:
<221> NAME/KEY: Unsure
<222> LOCATION: (555)..(555)
<223> OTHER INFORMATION: n = a, c, g or t
<220> FEATURE:
<221> NAME/KEY: Unsure
<222> LOCATION: (557)..(557)
<223> OTHER INFORMATION: n = a, c, g or t
<220> FEATURE:
<221> NAME/KEY: Unsure
<222> LOCATION: (562)..(562)
<223> OTHER INFORMATION: n = a, c, g or t
<220> FEATURE:
<221> NAME/KEY: Unsure
<222> LOCATION: (569)..(569)
<223> OTHER INFORMATION: n = a, c, g or t
<220> FEATURE:
<221> NAME/KEY: Unsure
<222> LOCATION: (586)..(587)
<223> OTHER INFORMATION: n = a, c, g or t
<220> FEATURE:
<221> NAME/KEY: Unsure
<222> LOCATION: (590)..(590)
<223> OTHER INFORMATION: n = a, c, g or t
<220> FEATURE:
<221> NAME/KEY: Unsure
<222> LOCATION: (592)..(592)
<223> OTHER INFORMATION: n = a, c, g or t
<220> FEATURE:
<221> NAME/KEY: Unsure
<222> LOCATION: (594)..(594)
<223> OTHER INFORMATION: n = a, c, g or t
<220> FEATURE:
<221> NAME/KEY: Unsure
<222> LOCATION: (597)..(597)
<223> OTHER INFORMATION: n = a, c, g or t
<220> FEATURE:
<221> NAME/KEY: Unsure
<222> LOCATION: (602)..(603)
<223> OTHER INFORMATION: n = a, c, g or t
<220> FEATURE:
<221> NAME/KEY: Unsure
<222> LOCATION: (606)..(606)
<223> OTHER INFORMATION: n = a, c, g or t
<220> FEATURE:
<221> NAME/KEY: Unsure
<222> LOCATION: (611)..(611)
<223> OTHER INFORMATION: n = a, c, g or t
<220> FEATURE:
<221> NAME/KEY: Unsure
<222> LOCATION: (618)..(619)
<223> OTHER INFORMATION: n = a, c, g or t
<220> FEATURE:
<221> NAME/KEY: Unsure
<222> LOCATION: (622)..(622)
<223> OTHER INFORMATION: n = a, c, g or t
<220> FEATURE:
<221> NAME/KEY: Unsure
```

-continued

```
<222> LOCATION: (626)..(626)
<223> OTHER INFORMATION: n = a, c, g or t
<220> FEATURE:
<221> NAME/KEY: Unsure
<222> LOCATION: (631)..(631)
<223> OTHER INFORMATION: n = a, c, g or t
<220> FEATURE:
<221> NAME/KEY: Unsure
<222> LOCATION: (635)..(635)
<223> OTHER INFORMATION: n = a, c, g or t
<220> FEATURE:
<221> NAME/KEY: Unsure
<222> LOCATION: (637)..(637)
<223> OTHER INFORMATION: n = a, c, g or t
<220> FEATURE:
<221> NAME/KEY: Unsure
<222> LOCATION: (643)..(643)
<223> OTHER INFORMATION: n = a, c, g or t
<220> FEATURE:
<221> NAME/KEY: Unsure
<222> LOCATION: (645)..(645)
<223> OTHER INFORMATION: n = a, c, g or t
<220> FEATURE:
<221> NAME/KEY: Unsure
<222> LOCATION: (648)..(648)
<223> OTHER INFORMATION: n = a, c, g or t
<220> FEATURE:
<221> NAME/KEY: Unsure
<222> LOCATION: (650)..(650)
<223> OTHER INFORMATION: n = a, c, g or t
<220> FEATURE:
<221> NAME/KEY: Unsure
<222> LOCATION: (653)..(653)
<223> OTHER INFORMATION: n = a, c, g or t
<220> FEATURE:
<221> NAME/KEY: Unsure
<222> LOCATION: (655)..(655)
<223> OTHER INFORMATION: n = a, c, g or t
<220> FEATURE:
<221> NAME/KEY: Unsure
<222> LOCATION: (658)..(658)
<223> OTHER INFORMATION: n = a, c, g or t
<220> FEATURE:
<221> NAME/KEY: Unsure
<222> LOCATION: (660)..(660)
<223> OTHER INFORMATION: n = a, c, g or t
<220> FEATURE:
<221> NAME/KEY: Unsure
<222> LOCATION: (663)..(663)
<223> OTHER INFORMATION: n = a, c, g or t
<220> FEATURE:
<221> NAME/KEY: Unsure
<222> LOCATION: (668)..(668)
<223> OTHER INFORMATION: n = a, c, g or t
<220> FEATURE:
<221> NAME/KEY: Unsure
<222> LOCATION: (670)..(670)
<223> OTHER INFORMATION: n = a, c, g or t
<220> FEATURE:
<221> NAME/KEY: Unsure
<222> LOCATION: (672)..(673)
<223> OTHER INFORMATION: n = a, c, g or t
<220> FEATURE:
<221> NAME/KEY: Unsure
<222> LOCATION: (677)..(677)
<223> OTHER INFORMATION: n = a, c, g or t
<220> FEATURE:
<221> NAME/KEY: Unsure
<222> LOCATION: (679)..(679)
<223> OTHER INFORMATION: n = a, c, g or t
<220> FEATURE:
<221> NAME/KEY: Unsure
<222> LOCATION: (683)..(683)
<223> OTHER INFORMATION: n = a, c, g or t
<220> FEATURE:
<221> NAME/KEY: Unsure
<222> LOCATION: (687)..(688)
<223> OTHER INFORMATION: n = a, c, g or t
<220> FEATURE:
```

-continued

```
<221> NAME/KEY: Unsure
<222> LOCATION: (691)..(691)
<223> OTHER INFORMATION: n = a, c, g or t
<220> FEATURE:
<221> NAME/KEY: Unsure
<222> LOCATION: (693)..(693)
<223> OTHER INFORMATION: n = a, c, g or t
<220> FEATURE:
<221> NAME/KEY: Unsure
<222> LOCATION: (696)..(696)
<223> OTHER INFORMATION: n = a, c, g or t
<220> FEATURE:
<221> NAME/KEY: Unsure
<222> LOCATION: (703)..(703)
<223> OTHER INFORMATION: n = a, c, g or t
<220> FEATURE:
<221> NAME/KEY: Unsure
<222> LOCATION: (705)..(705)
<223> OTHER INFORMATION: n = a, c, g or t
<220> FEATURE:
<221> NAME/KEY: Unsure
<222> LOCATION: (714)..(714)
<223> OTHER INFORMATION: n = a, c, g or t
<220> FEATURE:
<221> NAME/KEY: Unsure
<222> LOCATION: (720)..(721)
<223> OTHER INFORMATION: n = a, c, g or t
<220> FEATURE:
<221> NAME/KEY: Unsure
<222> LOCATION: (725)..(725)
<223> OTHER INFORMATION: n = a, c, g or t
<220> FEATURE:
<221> NAME/KEY: Unsure
<222> LOCATION: (727)..(727)
<223> OTHER INFORMATION: n = a, c, g or t
<220> FEATURE:
<221> NAME/KEY: Unsure
<222> LOCATION: (730)..(731)
<223> OTHER INFORMATION: n = a, c, g or t
<220> FEATURE:
<221> NAME/KEY: Unsure
<222> LOCATION: (734)..(734)
<223> OTHER INFORMATION: n = a, c, g or t
<220> FEATURE:
<221> NAME/KEY: Unsure
<222> LOCATION: (750)..(750)
<223> OTHER INFORMATION: n = a, c, g or t
<220> FEATURE:
<221> NAME/KEY: Unsure
<222> LOCATION: (755)..(756)
<223> OTHER INFORMATION: n = a, c, g or t
<220> FEATURE:
<221> NAME/KEY: Unsure
<222> LOCATION: (760)..(762)
<223> OTHER INFORMATION: n = a, c, g or t
<220> FEATURE:
<221> NAME/KEY: Unsure
<222> LOCATION: (767)..(767)
<223> OTHER INFORMATION: n = a, c, g or t
<220> FEATURE:
<221> NAME/KEY: Unsure
<222> LOCATION: (775)..(775)
<223> OTHER INFORMATION: n = a, c, g or t
<220> FEATURE:
<221> NAME/KEY: Unsure
<222> LOCATION: (780)..(781)
<223> OTHER INFORMATION: n = a, c, g or t
<220> FEATURE:
<221> NAME/KEY: Unsure
<222> LOCATION: (784)..(784)
<223> OTHER INFORMATION: n = a, c, g or t
<220> FEATURE:
<221> NAME/KEY: Unsure
<222> LOCATION: (787)..(787)
<223> OTHER INFORMATION: n = a, c, g or t
<220> FEATURE:
<221> NAME/KEY: Unsure
<222> LOCATION: (789)..(789)
<223> OTHER INFORMATION: n = a, c, g or t
```

-continued

```
<220> FEATURE:
<221> NAME/KEY: Unsure
<222> LOCATION: (794)..(796)
<223> OTHER INFORMATION: n = a, c, g or t
<220> FEATURE:
<221> NAME/KEY: Unsure
<222> LOCATION: (802)..(802)
<223> OTHER INFORMATION: n = a, c, g or t
<220> FEATURE:
<221> NAME/KEY: Unsure
<222> LOCATION: (804)..(804)
<223> OTHER INFORMATION: n = a, c, g or t
<220> FEATURE:
<221> NAME/KEY: Unsure
<222> LOCATION: (806)..(806)
<223> OTHER INFORMATION: n = a, c, g or t
<220> FEATURE:
<221> NAME/KEY: Unsure
<222> LOCATION: (814)..(814)
<223> OTHER INFORMATION: n = a, c, g or t
<220> FEATURE:
<221> NAME/KEY: Unsure
<222> LOCATION: (826)..(827)
<223> OTHER INFORMATION: n = a, c, g or t
<220> FEATURE:
<221> NAME/KEY: Unsure
<222> LOCATION: (834)..(834)
<223> OTHER INFORMATION: n = a, c, g or t
<220> FEATURE:
<221> NAME/KEY: Unsure
<222> LOCATION: (847)..(847)
<223> OTHER INFORMATION: n = a, c, g or t
<220> FEATURE:
<221> NAME/KEY: Unsure
<222> LOCATION: (850)..(850)
<223> OTHER INFORMATION: n = a, c, g or t
<220> FEATURE:
<221> NAME/KEY: Unsure
<222> LOCATION: (853)..(855)
<223> OTHER INFORMATION: n = a, c, g or t
<220> FEATURE:
<221> NAME/KEY: Unsure
<222> LOCATION: (864)..(865)
<223> OTHER INFORMATION: n = a, c, g or t
<220> FEATURE:
<221> NAME/KEY: Unsure
<222> LOCATION: (869)..(870)
<223> OTHER INFORMATION: n = a, c, g or t
<220> FEATURE:
<221> NAME/KEY: Unsure
<222> LOCATION: (872)..(872)
<223> OTHER INFORMATION: n = a, c, g or t
<220> FEATURE:
<221> NAME/KEY: Unsure
<222> LOCATION: (874)..(876)
<223> OTHER INFORMATION: n = a, c, g or t
<220> FEATURE:
<221> NAME/KEY: Unsure
<222> LOCATION: (878)..(878)
<223> OTHER INFORMATION: n = a, c, g or t
<220> FEATURE:
<221> NAME/KEY: Unsure
<222> LOCATION: (883)..(883)
<223> OTHER INFORMATION: n = a, c, g or t
<220> FEATURE:
<221> NAME/KEY: Unsure
<222> LOCATION: (887)..(887)
<223> OTHER INFORMATION: n = a, c, g or t
<220> FEATURE:
<221> NAME/KEY: Unsure
<222> LOCATION: (889)..(889)
<223> OTHER INFORMATION: n = a, c, g or t
<220> FEATURE:
<221> NAME/KEY: Unsure
<222> LOCATION: (900)..(900)
<223> OTHER INFORMATION: n = a, c, g or t
<220> FEATURE:
<221> NAME/KEY: Unsure
<222> LOCATION: (902)..(902)
```

-continued

```
<223> OTHER INFORMATION: n = a, c, g or t
<220> FEATURE:
<221> NAME/KEY: Unsure
<222> LOCATION: (904)..(905)
<223> OTHER INFORMATION: n = a, c, g or t
<220> FEATURE:
<221> NAME/KEY: Unsure
<222> LOCATION: (910)..(910)
<223> OTHER INFORMATION: n = a, c, g or t
<220> FEATURE:
<221> NAME/KEY: Unsure
<222> LOCATION: (915)..(916)
<223> OTHER INFORMATION: n = a, c, g or t
<220> FEATURE:
<221> NAME/KEY: Unsure
<222> LOCATION: (918)..(918)
<223> OTHER INFORMATION: n = a, c, g or t
<220> FEATURE:
<221> NAME/KEY: Unsure
<222> LOCATION: (923)..(923)
<223> OTHER INFORMATION: n = a, c, g or t
<220> FEATURE:
<221> NAME/KEY: Unsure
<222> LOCATION: (925)..(925)
<223> OTHER INFORMATION: n = a, c, g or t
<220> FEATURE:
<221> NAME/KEY: Unsure
<222> LOCATION: (930)..(930)
<223> OTHER INFORMATION: n = a, c, g or t
<220> FEATURE:
<221> NAME/KEY: Unsure
<222> LOCATION: (933)..(935)
<223> OTHER INFORMATION: n = a, c, g or t
<220> FEATURE:
<221> NAME/KEY: Unsure
<222> LOCATION: (937)..(938)
<223> OTHER INFORMATION: n = a, c, g or t
<220> FEATURE:
<221> NAME/KEY: Unsure
<222> LOCATION: (944)..(946)
<223> OTHER INFORMATION: n = a, c, g or t
<220> FEATURE:
<221> NAME/KEY: Unsure
<222> LOCATION: (949)..(949)
<223> OTHER INFORMATION: n = a, c, g or t
<220> FEATURE:
<221> NAME/KEY: Unsure
<222> LOCATION: (952)..(952)
<223> OTHER INFORMATION: n = a, c, g or t
<220> FEATURE:
<221> NAME/KEY: Unsure
<222> LOCATION: (954)..(954)
<223> OTHER INFORMATION: n = a, c, g or t
<220> FEATURE:
<221> NAME/KEY: Unsure
<222> LOCATION: (956)..(956)
<223> OTHER INFORMATION: n = a, c, g or t
<220> FEATURE:
<221> NAME/KEY: Unsure
<222> LOCATION: (958)..(960)
<223> OTHER INFORMATION: n = a, c, g or t
<220> FEATURE:
<221> NAME/KEY: Unsure
<222> LOCATION: (962)..(967)
<223> OTHER INFORMATION: n = a, c, g or t
<220> FEATURE:
<221> NAME/KEY: Unsure
<222> LOCATION: (970)..(972)
<223> OTHER INFORMATION: n = a, c, g or t
<220> FEATURE:
<221> NAME/KEY: Unsure
<222> LOCATION: (974)..(974)
<223> OTHER INFORMATION: n = a, c, g or t
<220> FEATURE:
<221> NAME/KEY: Unsure
<222> LOCATION: (978)..(978)
<223> OTHER INFORMATION: n = a, c, g or t
<220> FEATURE:
<221> NAME/KEY: Unsure
```

```
<222> LOCATION: (981)..(982)
<223> OTHER INFORMATION: n = a, c, g or t
<220> FEATURE:
<221> NAME/KEY: Unsure
<222> LOCATION: (996)..(997)
<223> OTHER INFORMATION: n = a, c, g or t
<220> FEATURE:
<221> NAME/KEY: Unsure
<222> LOCATION: (1000)..(1000)
<223> OTHER INFORMATION: n = a, c, g or t
<220> FEATURE:
<221> NAME/KEY: Unsure
<222> LOCATION: (1005)..(1006)
<223> OTHER INFORMATION: n = a, c, g or t
<220> FEATURE:
<221> NAME/KEY: Unsure
<222> LOCATION: (1009)..(1012)
<223> OTHER INFORMATION: n = a, c, g or t
<220> FEATURE:
<221> NAME/KEY: Unsure
<222> LOCATION: (1015)..(1015)
<223> OTHER INFORMATION: n = a, c, g or t
<220> FEATURE:
<221> NAME/KEY: Unsure
<222> LOCATION: (1027)..(1027)
<223> OTHER INFORMATION: n = a, c, g or t
<220> FEATURE:
<221> NAME/KEY: Unsure
<222> LOCATION: (1030)..(1030)
<223> OTHER INFORMATION: n = a, c, g or t
<220> FEATURE:
<221> NAME/KEY: Unsure
<222> LOCATION: (1032)..(1032)
<223> OTHER INFORMATION: n = a, c, g or t
<220> FEATURE:
<221> NAME/KEY: Unsure
<222> LOCATION: (1035)..(1035)
<223> OTHER INFORMATION: n = a, c, g or t
<220> FEATURE:
<221> NAME/KEY: Unsure
<222> LOCATION: (1039)..(1039)
<223> OTHER INFORMATION: n = a, c, g or t
<220> FEATURE:
<221> NAME/KEY: Unsure
<222> LOCATION: (1042)..(1042)
<223> OTHER INFORMATION: n = a, c, g or t
<220> FEATURE:
<221> NAME/KEY: Unsure
<222> LOCATION: (1045)..(1047)
<223> OTHER INFORMATION: n = a, c, g or t
<220> FEATURE:
<221> NAME/KEY: Unsure
<222> LOCATION: (1055)..(1055)
<223> OTHER INFORMATION: n = a, c, g or t
<220> FEATURE:
<221> NAME/KEY: Unsure
<222> LOCATION: (1061)..(1061)
<223> OTHER INFORMATION: n = a, c, g or t
<220> FEATURE:
<221> NAME/KEY: Unsure
<222> LOCATION: (1076)..(1076)
<223> OTHER INFORMATION: n = a, c, g or t
<220> FEATURE:
<221> NAME/KEY: Unsure
<222> LOCATION: (1081)..(1082)
<223> OTHER INFORMATION: n = a, c, g or t
<220> FEATURE:
<221> NAME/KEY: Unsure
<222> LOCATION: (1086)..(1086)
<223> OTHER INFORMATION: n = a, c, g or t
<220> FEATURE:
<221> NAME/KEY: Unsure
<222> LOCATION: (1091)..(1091)
<223> OTHER INFORMATION: n = a, c, g or t
<220> FEATURE:
<221> NAME/KEY: Unsure
<222> LOCATION: (1094)..(1096)
<223> OTHER INFORMATION: n = a, c, g or t
<220> FEATURE:
```

```
<221> NAME/KEY: Unsure
<222> LOCATION: (1103)..(1103)
<223> OTHER INFORMATION: n = a, c, g or t
<220> FEATURE:
<221> NAME/KEY: Unsure
<222> LOCATION: (1105)..(1107)
<223> OTHER INFORMATION: n = a, c, g or t
<220> FEATURE:
<221> NAME/KEY: Unsure
<222> LOCATION: (1110)..(1111)
<223> OTHER INFORMATION: n = a, c, g or t
<220> FEATURE:
<221> NAME/KEY: Unsure
<222> LOCATION: (1116)..(1118)
<223> OTHER INFORMATION: n = a, c, g or t
<220> FEATURE:
<221> NAME/KEY: Unsure
<222> LOCATION: (1126)..(1127)
<223> OTHER INFORMATION: n = a, c, g or t
<220> FEATURE:
<221> NAME/KEY: Unsure
<222> LOCATION: (1130)..(1130)
<223> OTHER INFORMATION: n = a, c, g or t
<220> FEATURE:
<221> NAME/KEY: Unsure
<222> LOCATION: (1132)..(1134)
<223> OTHER INFORMATION: n = a, c, g or t
<220> FEATURE:
<221> NAME/KEY: Unsure
<222> LOCATION: (1136)..(1136)
<223> OTHER INFORMATION: n = a, c, g or t
<220> FEATURE:
<221> NAME/KEY: Unsure
<222> LOCATION: (1141)..(1141)
<223> OTHER INFORMATION: n = a, c, g or t
<220> FEATURE:
<221> NAME/KEY: Unsure
<222> LOCATION: (1143)..(1144)
<223> OTHER INFORMATION: n = a, c, g or t
<220> FEATURE:
<221> NAME/KEY: Unsure
<222> LOCATION: (1149)..(1149)
<223> OTHER INFORMATION: n = a, c, g or t
<220> FEATURE:
<221> NAME/KEY: Unsure
<222> LOCATION: (1152)..(1155)
<223> OTHER INFORMATION: n = a, c, g or t
<220> FEATURE:
<221> NAME/KEY: Unsure
<222> LOCATION: (1159)..(1160)
<223> OTHER INFORMATION: n = a, c, g or t
<220> FEATURE:
<221> NAME/KEY: Unsure
<222> LOCATION: (1165)..(1166)
<223> OTHER INFORMATION: n = a, c, g or t
<220> FEATURE:
<221> NAME/KEY: Unsure
<222> LOCATION: (1169)..(1170)
<223> OTHER INFORMATION: n = a, c, g or t
<220> FEATURE:
<221> NAME/KEY: Unsure
<222> LOCATION: (1172)..(1172)
<223> OTHER INFORMATION: n = a, c, g or t
<220> FEATURE:
<221> NAME/KEY: Unsure
<222> LOCATION: (1176)..(1178)
<223> OTHER INFORMATION: n = a, c, g or t
<220> FEATURE:
<221> NAME/KEY: Unsure
<222> LOCATION: (1180)..(1180)
<223> OTHER INFORMATION: n = a, c, g or t
<220> FEATURE:
<221> NAME/KEY: Unsure
<222> LOCATION: (1182)..(1182)
<223> OTHER INFORMATION: n = a, c, g or t
<220> FEATURE:
<221> NAME/KEY: Unsure
<222> LOCATION: (1184)..(1184)
<223> OTHER INFORMATION: n = a, c, g or t
```

```
<220> FEATURE:
<221> NAME/KEY: Unsure
<222> LOCATION: (1186)..(1187)
<223> OTHER INFORMATION: n = a, c, g or t
<220> FEATURE:
<221> NAME/KEY: Unsure
<222> LOCATION: (1189)..(1189)
<223> OTHER INFORMATION: n = a, c, g or t
<220> FEATURE:
<221> NAME/KEY: Unsure
<222> LOCATION: (1208)..(1208)
<223> OTHER INFORMATION: n = a, c, g or t
<220> FEATURE:
<221> NAME/KEY: Unsure
<222> LOCATION: (1212)..(1212)
<223> OTHER INFORMATION: n = a, c, g or t
<220> FEATURE:
<221> NAME/KEY: Unsure
<222> LOCATION: (1215)..(1216)
<223> OTHER INFORMATION: n = a, c, g or t
<220> FEATURE:
<221> NAME/KEY: Unsure
<222> LOCATION: (1227)..(1227)
<223> OTHER INFORMATION: n = a, c, g or t
<220> FEATURE:
<221> NAME/KEY: Unsure
<222> LOCATION: (1232)..(1232)
<223> OTHER INFORMATION: n = a, c, g or t

<400> SEQUENCE: 17
ctgaggctgg ggctggggct ggggctgagg ctggagctgg gactgaggct ggggctgggg      60
ctggggctgg ggctgaggct ggggctgggg ctggggctgg ggctgggact gaggctgggg     120
ctggggctga ggctggggct gggactgagg ctggggctgg gactgaggct ggggctgggg     180
ctgaggttgg ggctgggact gaggctgggg ctanggctgg ggctgaggct ggggctaggg     240
ctnaggctga ggttggggct ggggctgggng ctgacgctgg ggctgaggct nggnctgagg     300
ctggagctgg ggctgangct ggggctgggg ctgnngctga nctggggctg aggctccngc     360
tgaagctgag gctggggcnt aacgctgagc tngnngctga tgctnatgct tgnctnanaa     420
tgngnatgnn ctgnggctnn cntccnngac aaananttnn aacttgnggt ttnntcctgg     480
gaatnnaaat ntccaccann tntgnaaant tangcnnttn ggacnaanaa anantcnnna     540
antctaannc cnccnanana tnctaggana tgtttacaca agcaannatn tnancanatc     600 anncncatc ntttaaannt gnattnaaaa naaanantga aangnccncn ttnaccncn      660 ttnttaantn gnnaacntna ctnactnnca nanatnttaa aantnggaaa caancacacn     720
ntttnanacn nctnacttcg gagaataaan actcnnnctn nnaatgnctc agacnacccn     780
ntcnttngng cacnnnaaaa tnananccttt ctnttttga tacccnnaaa aaanaaaaac    840 cacttttnaan aannntttta ttcnnaatnn cnannntnta canaggntnt tcacattctn     900
ancnnatttn tccanntnta ttntncccctn ttnnncnnat attnnncana ananantnnn     960
cnnnnnnacn nncncccnta nnaatattgc acaacnnaan aatannacnn nnttntataa    1020
aaatcanaan antancacna cnccnnnatc cctanaagtg nttaaaactc tatgtncnnc    1080
nntctntaat ntannncaaa tanannnctn nttggnnnat caccannacn tnnnanaccc    1140
nanncctant annnntacnn cagcnncann tncttnnntn tntntnnana acccaactcc    1200
cttatttnat ancanntcac tctcccntat cn                                 1232

<210> SEQ ID NO 18
<211> LENGTH: 387
<212> TYPE: PRT
<213> ORGANISM: Homo sapiens
```

<400> SEQUENCE: 18

```
Met Tyr Ser Met Met Met Glu Thr Asp Leu His Ser Pro Gly Gly Ala
1               5                   10                  15

Gln Ala Pro Thr Asn Leu Ser Gly Pro Ala Gly Ala Gly Gly Gly Gly
            20                  25                  30

Gly Gly Gly Gly Gly Gly Gly Gly Gly Gly Ala Lys Ala Asn Gln
        35                  40                  45

Asp Arg Val Lys Arg Pro Met Asn Ala Phe Met Val Trp Ser Arg Gly
    50                  55                  60

Gln Arg Arg Lys Met Ala Gln Glu Asn Pro Lys Met His Asn Ser Glu
65                  70                  75                  80

Ile Ser Lys Arg Leu Gly Ala Glu Trp Lys Val Met Ser Glu Ala Glu
                85                  90                  95

Lys Arg Pro Phe Ile Asp Glu Ala Lys Arg Leu Arg Ala Leu His Met
            100                 105                 110

Lys Glu His Pro Asp Tyr Lys Tyr Arg Pro Arg Arg Lys Thr Lys Thr
            115                 120                 125

Leu Leu Lys Lys Asp Lys Tyr Ser Leu Ala Gly Gly Leu Leu Ala Ala
    130                 135                 140

Gly Ala Gly Gly Gly Gly Ala Val Ala Met Gly Val Gly Val Gly
145                 150                 155                 160

Val Gly Ala Ala Pro Val Gly Gln Arg Leu Glu Ser Pro Gly Gly Ala
                165                 170                 175

Ala Gly Gly Ala Tyr Ala His Val Asn Gly Trp Ala Asn Gly Ala Tyr
            180                 185                 190

Pro Gly Ser Val Ala Ala Ala Ala Ala Ala Met Met Gln Glu
            195                 200                 205

Ala Gln Leu Ala Tyr Gly Gln His Pro Gly Ala Gly Gly Ala His Pro
    210                 215                 220

His Arg Thr Pro Ala His Pro His Pro His His Pro His Ala His Pro
225                 230                 235                 240

His Asn Pro Gln Pro Met His Arg Tyr Asp Met Gly Ala Leu Gln Tyr
                245                 250                 255

Ser Pro Ile Ser Asn Ser Gln Gly Tyr Met Ser Ala Ser Pro Ser Gly
            260                 265                 270

Tyr Gly Gly Leu Pro Tyr Gly Ala Ala Ala Ala Ala Ala Ala Ala His
            275                 280                 285

Gln Asn Ser Ala Val Ala Ala Ala Ala Ala Ala Ala Ser Ser
    290                 295                 300

Gly Ala Leu Gly Ala Leu Gly Ser Leu Val Lys Ser Glu Pro Ser Gly
305                 310                 315                 320

Ser Pro Pro Ala Pro Ala His Ser Arg Ala Pro Cys Pro Gly Asp Leu
                325                 330                 335

Arg Glu Met Ile Ser Met Tyr Leu Pro Ala Gly Glu Gly Gly Asp Pro
            340                 345                 350

Ala Ala Ala Ala Ala Ala Ala Gln Ser Arg Leu His Ser Leu Pro
            355                 360                 365

Gln His Tyr Gln Gly Ala Gly Ala Gly Val Asn Gly Thr Val Pro Leu
    370                 375                 380

Thr His Ile
385
```

<210> SEQ ID NO 19

```
<211> LENGTH: 317
<212> TYPE: PRT
<213> ORGANISM: Homo sapiens

<400> SEQUENCE: 19

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Gly Gly
            20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
                100                 105                 110

Arg Arg Lys Thr Lys Thr Leu Met Lys Lys Asp Lys Tyr Thr Leu Pro
                115                 120                 125

Gly Gly Leu Leu Ala Pro Gly Gly Asn Ser Met Ala Ser Gly Val Gly
            130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
            195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315

<210> SEQ ID NO 20
<211> LENGTH: 443
<212> TYPE: PRT
<213> ORGANISM: Homo sapiens

<400> SEQUENCE: 20

Met Arg Pro Val Arg Glu Asn Ser Ser Gly Ala Arg Ser Pro Arg Val
1               5                   10                  15

Pro Ala Asp Leu Ala Arg Ser Ile Leu Ile Ser Leu Pro Phe Pro Pro
            20                  25                  30
```

-continued

```
Asp Ser Leu Ala His Arg Pro Pro Ser Ser Ala Pro Thr Glu Ser Gln
        35                  40                  45

Gly Leu Phe Thr Val Ala Ala Pro Ala Pro Gly Ala Pro Ser Pro Pro
    50                  55                  60

Ala Thr Leu Ala His Leu Leu Pro Ala Pro Ala Met Tyr Ser Leu Leu
65                  70                  75                  80

Glu Thr Glu Leu Lys Asn Pro Val Gly Thr Pro Thr Gln Ala Ala Gly
                85                  90                  95

Thr Gly Gly Pro Ala Ala Pro Gly Gly Ala Gly Lys Ser Ser Ala Asn
            100                 105                 110

Ala Ala Gly Gly Ala Asn Ser Gly Gly Gly Ser Ser Gly Gly Ala Ser
            115                 120                 125

Gly Gly Gly Gly Thr Asp Gln Asp Arg Val Lys Arg Pro Met Asn
        130                 135                 140

Ala Phe Met Val Trp Ser Arg Gly Gln Arg Arg Lys Met Ala Leu Glu
145                 150                 155                 160

Asn Pro Lys Met His Asn Ser Glu Ile Ser Lys Arg Leu Gly Ala Asp
                165                 170                 175

Trp Lys Leu Leu Thr Asp Ala Glu Lys Arg Pro Phe Ile Asp Glu Ala
            180                 185                 190

Lys Arg Leu Arg Ala Val His Met Lys Glu Tyr Pro Asp Tyr Lys Tyr
        195                 200                 205

Arg Pro Arg Arg Lys Thr Lys Thr Leu Leu Lys Asp Lys Tyr Ser
210                 215                 220

Leu Pro Ser Gly Leu Leu Pro Pro Gly Ala Ala Ala Ala Ala Ala
225                 230                 235                 240

Ala Ala Ala Ala Ala Ala Ala Ser Ser Pro Val Gly Val Gly Gln
                245                 250                 255

Arg Leu Asp Thr Tyr Thr His Val Asn Gly Trp Ala Asn Gly Ala Tyr
            260                 265                 270

Ser Leu Val Gln Glu Gln Leu Gly Tyr Ala Gln Pro Pro Ser Met Ser
        275                 280                 285

Ser Pro Pro Pro Pro Ala Leu His Arg Tyr Asp Met Ala Gly Leu
290                 295                 300

Gln Tyr Ser Pro Met Met Pro Gly Ala Gln Ser Tyr Met Asn Val
305                 310                 315                 320

Ala Ala Ala Ala Ala Ala Ser Gly Tyr Gly Gly Met Ala Pro Ser
                325                 330                 335

Ala Thr Ala Ala Ala Ala Ala Tyr Gly Gln Gln Pro Ala Thr Ala
        340                 345                 350

Ala Ala Ala Ala Ala Ala Ala Met Ser Leu Gly Pro Met Gly
            355                 360                 365

Ser Val Val Lys Ser Glu Pro Ser Ser Pro Pro Ala Ile Ala Ser
        370                 375                 380

His Ser Gln Arg Ala Cys Leu Gly Asp Leu Arg Asp Met Ile Ser Met
385                 390                 395                 400

Tyr Leu Pro Pro Gly Gly Asp Ala Ala Asp Ala Ala Ser Pro Leu Pro
                405                 410                 415

Gly Gly Arg Leu His Gly Val His Gln His Tyr Gln Gly Ala Gly Thr
        420                 425                 430

Ala Val Asn Gly Thr Val Pro Leu Thr His Ile
        435                 440
```

```
<210> SEQ ID NO 21
<211> LENGTH: 276
<212> TYPE: PRT
<213> ORGANISM: Homo sapiens

<400> SEQUENCE: 21

Met Ser Lys Pro Val Asp His Val Lys Arg Pro Met Asn Ala Phe Met
1               5                   10                  15

Val Trp Ser Arg Ala Gln Arg Lys Met Ala Gln Glu Asn Pro Lys
            20                  25                  30

Met His Asn Ser Glu Ile Ser Lys Arg Leu Gly Ala Glu Trp Lys Leu
            35                  40                  45

Leu Thr Glu Ser Glu Lys Arg Pro Phe Ile Asp Glu Ala Lys Arg Leu
        50                  55                  60

Arg Ala Met His Met Lys Glu His Pro Asp Tyr Lys Tyr Arg Pro Arg
65                  70                  75                  80

Arg Lys Pro Lys Thr Leu Leu Lys Lys Asp Lys Phe Ala Phe Pro Val
                85                  90                  95

Pro Tyr Gly Leu Gly Gly Val Ala Asp Ala Glu His Pro Ala Leu Lys
            100                 105                 110

Ala Gly Ala Gly Leu His Ala Gly Ala Gly Gly Leu Val Pro Glu
            115                 120                 125

Ser Leu Leu Ala Asn Pro Glu Lys Ala Ala Ala Ala Ala Ala Ala
        130                 135                 140

Ala Ala Arg Val Phe Phe Pro Gln Ser Ala Ala Ala Ala Ala Ala
145                 150                 155                 160

Ala Ala Ala Ala Ala Ala Gly Ser Pro Tyr Ser Leu Leu Asp Leu Gly
                165                 170                 175

Ser Lys Met Ala Glu Ile Ser Ser Ser Ser Gly Leu Pro Tyr Ala
            180                 185                 190

Ser Ser Leu Gly Tyr Pro Thr Ala Gly Ala Gly Ala Phe His Gly Ala
        195                 200                 205

Ala Ala Ala Ala Ala Ala Ala Ala Ala Ala Gly Gly His Thr His
210                 215                 220

Ser His Pro Ser Pro Gly Asn Pro Gly Tyr Met Ile Pro Cys Asn Cys
225                 230                 235                 240

Ser Ala Trp Pro Ser Pro Gly Leu Gln Pro Pro Leu Ala Tyr Ile Leu
                245                 250                 255

Leu Pro Gly Met Gly Lys Pro Gln Leu Asp Pro Tyr Pro Ala Ala Tyr
            260                 265                 270

Ala Ala Ala Leu
            275

<210> SEQ ID NO 22
<211> LENGTH: 533
<212> TYPE: PRT
<213> ORGANISM: Homo sapiens

<400> SEQUENCE: 22

Met Leu Leu Asp Ala Gly Pro Gln Phe Pro Ala Ile Gly Val Gly Ser
1               5                   10                  15

Phe Ala Arg His His His His Ser Ala Ala Ala Ala Ala Ala Ala
            20                  25                  30

Ala Glu Met Gln Asp Arg Glu Leu Ser Leu Ala Ala Ala Gln Asn Gly
            35                  40                  45
```

-continued

```
Phe Val Asp Ser Ala Ala His Met Gly Ala Phe Lys Leu Asn Pro
    50                  55                  60

Gly Ala His Glu Leu Ser Pro Gly Gln Ser Ser Ala Phe Thr Ser Gln
65                      70                  75                  80

Gly Pro Gly Ala Tyr Pro Gly Ser Ala Ala Ala Ala Ala Ala
                85                  90                  95

Ala Leu Gly Pro His Ala Ala His Val Gly Ser Tyr Ser Gly Pro Pro
                100                 105                 110

Phe Asn Ser Thr Arg Asp Phe Leu Phe Arg Ser Ala Arg Leu Pro Gly
            115                 120                 125

Thr Ser Ala Pro Gly Gly Gln His Gly Leu Phe Gly Pro Gly Ala
130                 135                 140

Gly Gly Leu His His Ala His Ser Asp Ala Gln Gly His Leu Leu Phe
145                 150                 155                 160

Pro Gly Leu Pro Glu Gln His Gly Pro His Gly Ser Gln Asn Val Leu
                165                 170                 175

Asn Gly Gln Met Arg Leu Gly Leu Pro Gly Glu Val Phe Gly Arg Ser
            180                 185                 190

Glu Gln Tyr Arg Gln Val Ala Ser Pro Arg Thr Asp Pro Tyr Ser Ala
            195                 200                 205

Ala Gln Leu His Asn Gln Tyr Gly Pro Met Asn Met Asn Met Gly Met
210                 215                 220

Asn Met Ala Ala Ala Ala His His His His His His His His
225                 230                 235                 240

Pro Gly Ala Phe Phe Arg Tyr Met Arg Gln Gln Cys Ile Lys Gln Glu
                245                 250                 255

Leu Ile Cys Lys Trp Ile Asp Pro Glu Gln Leu Ser Asn Pro Lys Lys
            260                 265                 270

Ser Cys Asn Lys Thr Phe Ser Thr Met His Glu Leu Val Thr His Val
    275                 280                 285

Ser Val Glu His Val Gly Gly Pro Glu Gln Ser Asn His Val Cys Phe
290                 295                 300

Trp Glu Glu Cys Pro Arg Glu Gly Lys Pro Phe Lys Ala Lys Tyr Lys
305                 310                 315                 320

Leu Val Asn His Ile Arg Val His Thr Gly Glu Lys Pro Phe Pro Cys
                325                 330                 335

Pro Phe Pro Gly Cys Gly Lys Val Phe Ala Arg Ser Glu Asn Leu Lys
            340                 345                 350

Ile His Lys Arg Thr His Thr Gly Glu Lys Pro Phe Gln Cys Glu Phe
    355                 360                 365

Glu Gly Cys Asp Arg Arg Phe Ala Asn Ser Ser Asp Arg Lys Lys His
370                 375                 380

Met His Val His Thr Ser Asp Lys Pro Tyr Leu Cys Lys Met Cys Asp
385                 390                 395                 400

Lys Ser Tyr Thr His Pro Ser Ser Leu Arg Lys His Met Lys Val His
                405                 410                 415

Glu Ser Ser Pro Gln Gly Ser Glu Ser Pro Ala Ala Ser Ser Gly
            420                 425                 430

Tyr Glu Ser Ser Thr Pro Pro Gly Leu Val Ser Pro Ser Ala Glu Pro
            435                 440                 445

Gln Ser Ser Ser Asn Leu Ser Pro Ala Ala Ala Ala Ala Ala Ala
    450                 455                 460

Ala Ala Ala Ala Ala Ala Ala Val Ser Ala Val His Arg Gly Gly Gly
```

```
                        -continued
465                 470                 475                 480
Ser Gly Ser Gly Gly Ala Gly Gly Gly Ser Gly Gly Gly Ser Gly Ser
                485                 490                 495

Gly Gly Gly Gly Gly Ala Gly Gly Gly Gly Gly Gly Ser Ser Gly
            500                 505                 510

Gly Gly Ser Gly Thr Ala Gly Gly His Ser Gly Leu Ser Ser Asn Phe
        515                 520                 525

Asn Glu Trp Tyr Val
        530
```

SMALL CELL LUNG CANCER ASSOCIATED ANTIGENS AND USES THEREFOR

RELATED APPLICATIONS

This application is a divisional of U.S. application Ser. No. 09/489,101, filed Jan. 21, 2000, now abandoned, the disclosure of which is incorporated by reference herein in its entirety.

FIELD OF THE INVENTION

The invention relates to nucleic acids and encoded polypeptides which are cancer associated antigens expressed in patients afflicted with a variety of cancers. The invention also relates to agents which bind the nucleic acids or polypeptides. The nucleic acid molecules, polypeptides coded for by such molecules and peptides derived therefrom, as well as related antibodies and cytolytic T lymphocytes, are useful, inter alia, in diagnostic and therapeutic contexts.

BACKGROUND OF THE INVENTION

The mechanism by which T cells recognize foreign materials has been implicated in cancer. A number of cytolytic T lymphocyte (CTL) clones directed against autologous melanoma antigens, testicular antigens, and melanocyte differentiation antigens have been described. In many instances, the antigens recognized by these clones have been characterized.

The use of autologous CTLs for identifying tumor antigens requires that the target cells which express the antigens can be cultured in vitro and that stable lines of autologous CTL clones which recognize the antigen-expressing cells can be isolated and propagated. While this approach has worked well for melanoma antigens, other tumor types, such as epithelial cancers including breast and colon cancer, have proved refractory to the approach.

More recently another approach to the problem has been described by Sahin et al. (Proc. Natl. Acad. Sci. USA 92:11810-11813, 1995). According to this approach, autologous antisera are used to identify immunogenic protein antigens expressed in cancer cells by screening expression libraries constructed from tumor cell cDNA. Antigen-encoding clones so identified have been found to have elicited an high-titer humoral immune response in the patients from which the antisera were obtained. Such a high-titer IgG response implies helper T cell recognition of the detected antigen. These tumor antigens can then be screened for the presence of MHC/HLA class I and class II motifs and reactivity with CTLs.

Presently there is a need for additional cancer antigens for development of therapeutics and diagnosis applicable to a greater number of cancer patients having various cancers.

SUMMARY OF THE INVENTION

Autologous antibody screening has now been applied to small cell lung cancer using antisera from cancer patients. Numerous cancer associated antigens have been identified. The invention provides, inter alia, isolated nucleic acid molecules, expression vectors containing those molecules and host cells transfected with those molecules. The invention also provides isolated proteins and peptides, antibodies to those proteins and peptides and CTLs which recognize the proteins and peptides. Fragments including functional fragments and variants of the foregoing also are provided. Kits containing the foregoing molecules additionally are provided. The foregoing can be used in the diagnosis, monitoring, research, or treatment of conditions characterized by the expression of one or more cancer associated antigens.

Prior to the present invention, only a handful of small cell lung cancer associated genes had been identified in the past 20 years. The invention involves the surprising discovery of several genes, some previously known and some previously unknown, which are expressed in individuals who have cancer. These individuals all have serum antibodies against the proteins (or fragments thereof) encoded by these genes. Thus, abnormally expressed genes are recognized by the host's immune system and therefore can form a basis for diagnosis, monitoring and therapy.

The invention involves the use of a single material, a plurality of different materials and even large panels and combinations of materials. For example, a single gene, a single protein encoded by a gene, a single functional fragment thereof, a single antibody thereto, etc. can be used in methods and products of the invention. Likewise, pairs, groups and even panels of these materials and optionally other cancer associated antigen genes and/or gene products can be used for diagnosis, monitoring and therapy. The pairs, groups or panels can involve 2, 3, 4, 5 or more genes, gene products, fragments thereof or agents that recognize such materials. A plurality of such materials are not only useful in monitoring, typing, characterizing and diagnosing cells abnormally expressing such genes, but a plurality of such materials can be used therapeutically. An example of the use of a plurality of such materials for the prevention, delay of onset, amelioration, etc. of cancer cells, which express or will express such genes prophylactically or acutely. Any and all combinations of the genes, gene products, and materials which recognize the genes and gene products can be tested and identified for use according to the invention. It would be far too lengthy to recite all such combinations; those skilled in the art, particularly in view of the teaching contained herein, will readily be able to determine which combinations are most appropriate for which circumstances.

As will be clear from the following discussion, the invention has in vivo and in vitro uses, including for therapeutic, diagnostic, monitoring and research purposes. One aspect of the invention is the ability to fingerprint a cell expressing a number of the genes identified according to the invention by, for example, quantifying the expression of such gene products. Such fingerprints will be characteristic, for example, of the stage of the cancer, the type of the cancer, or even the effect in animal models of a therapy on a cancer. Cells also can be screened to determine whether such cells abnormally express the genes identified according to the invention.

The invention, in one aspect, is a method of diagnosing a disorder characterized by expression of a cancer associated antigen precursor coded for by a nucleic acid molecule. The method involves the steps of contacting a biological sample isolated from a subject with an agent that specifically binds to the nucleic acid molecule, an expression product thereof, or a fragment of an expression product thereof complexed with an MHC, preferably an HLA, molecule, wherein the nucleic acid molecule is a NA Group 1 nucleic acid molecule, and determining the interaction between the agent and the nucleic acid molecule, the expression product or fragment of the expression product as a determination of the disorder.

In one embodiment the agent is selected from the group consisting of (a) a nucleic acid molecule comprising NA Group 1 nucleic acid molecules or a fragment thereof, (b) a nucleic acid molecule comprising NA Group 3 nucleic acid molecules or a fragment thereof, (c) a nucleic acid molecule comprising NA Group 5 nucleic acid molecules or a fragment thereof, (d) an antibody that binds to an expression product, or a fragment thereof, of NA group 1 nucleic acids, (e) an antibody that binds to an expression product, or a fragment thereof, of NA group 3 nucleic acids, (f) an antibody that binds to an expression product, or a fragment thereof, of NA group 5 nucleic acids, (g) and agent that binds to a complex of an MHC, preferably HLA, molecule and a fragment of an expression product of a NA Group 1 nucleic acid, (h) an agent that binds to a complex of an MHC, preferably HLA, molecule and a fragment of an expression product of a NA group 3 nucleic acid, and (i) an agent that binds to a complex of an MHC, preferably HLA, molecule and a fragment of an expression product of a NA Group 5 nucleic acid.

The disorder may be characterized by expression of a plurality of cancer associated antigen precursors. Thus the methods of diagnosis may include use of a plurality of agents, each of which is specific for a different human cancer associated antigen precursor (including at least one of the cancer associated antigen precursors disclosed herein), and wherein said plurality of agents is at least 2, at least 3, at least 4, at least 5, at least 6, at least 7, at least 8, at least 9 or at least 10 such agents.

In each of the above embodiments the disorder preferably is selected from the group consisting of lung cancers including small cell lung cancer and non-small cell lung cancer, melanoma, colon cancer, breast cancer, head and neck cancer, transitional cancer, leiomyosarcoma and synovial sarcoma.

In some embodiments, the nucleic acid molecule is selected from the group consisting of SOX2 nucleic acids, SOXI nucleic acids, ZIC2 nucleic acids, SOX3 nucleic acids and SOX21 nucleic acids. Preferably the nucleic acid molecule is selected from the group consisting of SEQ ID NO:3, SEQ ID NO:4, SEQ ID NO:5, SEQ ID NO:11 and SEQ ID NO:12.

In certain embodiments, the biological sample is isolated from a tissue selected from the group consisting of non-brain, non-testis, non-prostate, non-small intestine and non-colon tissues.

In another aspect the invention is a method for determining regression, progression or onset of a condition characterized by expression of abnormal levels of a protein encoded by a nucleic acid molecule that is a NA Group 1 molecule. The method involves the steps of monitoring a sample, from a subject who has or is suspected of having the condition, for a parameter selected from the group consisting of (i) the protein, (ii) a peptide derived from the protein, (iii) an antibody which selectively binds the protein or peptide, and (iv) cytolytic T cells specific for a complex of the peptide derived from the protein and an MHC molecule, as a determination of regression, progression or onset of said condition. In one embodiment the sample is a body fluid, a body effusion or a tissue.

In another embodiment the step of monitoring comprises contacting the sample with a detectable agent selected from the group consisting of (a) an antibody which selectively binds the protein of (i), or the peptide of (ii), (b) a protein or peptide which binds the antibody of (iii), and (c) a cell which presents the complex of the peptide and MHC molecule of (iv). In a preferred embodiment the antibody, the protein, the peptide or the cell is labeled with a radioactive label or an enzyme. The sample in a preferred embodiment is assayed for the peptide.

According to another embodiment the nucleic acid molecule is one of the following: a NA Group 3 molecule or a NA Group 5 molecule. In still another embodiment, the nucleic acid molecule is selected from the group consisting of SOX2 nucleic acids, SOX1 nucleic acids, ZIC2 nucleic acids, SOX3 nucleic acids and SOX21 nucleic acids. Preferably the nucleic acid molecule is selected from the group consisting of SEQ ID NO:3, SEQ ID NO:4, SEQ ID NO:5, SEQ ID NO:11 and SEQ ID NO:12.

In yet another embodiment the protein is a plurality of proteins, the parameter is a plurality of parameters, each of the plurality of parameters being specific for a different of the plurality of proteins, at least one of which is a cancer associated protein encoded by a NA group 1 molecule. In certain embodiments the protein is a plurality of proteins, at least one of which is encoded by SOX2 (SEQ ID NO:3) or ZIC2 (SEQ ID NO:5), and wherein the parameter is a plurality of parameters, each of the plurality of parameters being specific for a different of the plurality of proteins.

The invention in another aspect is a pharmaceutical preparation for a human subject. The pharmaceutical preparation includes an agent which when administered to the subject enriches selectively the presence of complexes of an HLA molecule and a human cancer associated antigen, and a pharmaceutically acceptable carrier, wherein the human cancer associated antigen is a fragment of a human cancer associated antigen precursor encoded by a nucleic acid molecule which comprises a NA Group 1 molecule. In one embodiment the nucleic acid molecule is a NA Group 3 nucleic acid molecule or a NA group 5 nucleic acid molecule.

The agent in one embodiment comprises a plurality of agents, each of which enriches selectively in the subject complexes of an HLA molecule and a different human cancer associated antigen. Preferably the plurality is at least two, at least three, at least four or at least 5 different such agents.

In certain embodiments, the agent comprises a plurality of agents, at least one of which is a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12, or an expression product thereof, and each of which enriches selectively in the subject complexes of an HLA molecule and a different human cancer associated antigen.

In another embodiment the agent is selected from the group consisting of (1) an isolated polypeptide comprising the human cancer associated antigen, or a functional variant thereof, (2) an isolated nucleic acid operably linked to a promoter for expressing the isolated polypeptide, or functional variant thereof, (3) a host cell expressing the isolated polypeptide, or functional variant thereof, and (4) isolated complexes of the polypeptide, or functional variants thereof, and an HLA molecule.

The agent may be a cell expressing an isolated polypeptide. In one embodiment the agent is a cell expressing an isolated polypeptide comprising the human cancer associated antigen or a functional variant thereof. In another embodiment the agent is a cell expressing an isolated polypeptide comprising the human cancer associated antigen or a functional variant thereof, and wherein the cell expresses an HLA molecule that binds the polypeptide. The cell can express one or both of the polypeptide and HLA molecule recombinantly. In preferred embodiments the cell is nonproliferative. In other preferred embodiments, the isolated polypeptide is or includes a polypeptide encoded by a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12. In yet another embodiment the agent is at least two, at least three, at least four or at least five different polypeptides, each representing a different human cancer associated antigen or functional variant thereof.

The agent in one embodiment is a PP Group 2 polypeptide. In other embodiments the agent is a PP Group 3 polypeptide or a PP Group 4 polypeptide.

In an embodiment each of the pharmaceutical preparations described herein also includes an adjuvant.

According to another aspect the invention, a composition is provided which includes an isolated agent that binds selectively a PP Group 1 polypeptide. In separate embodiments the agent binds selectively to a polypeptide selected from the following: a PP Group 2 polypeptide, a PP Group 3 polypeptide, a PP Group 4 polypeptide, and a PP Group 5 polypeptide. In other embodiments, the agent is a plurality of different agents that bind selectively at least two, at least three, at least four, or at least five different such polypeptides. In each of the above described embodiments the agent may be an antibody. In a preferred embodiment, at least one of polypeptides is encoded by a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12, or a fragment thereof.

In another aspect the invention is a composition of matter composed of a conjugate of the agent of the above-described compositions of the invention and a therapeutic or diagnostic agent. Preferably the conjugate is of the agent and a therapeutic or diagnostic that is a toxin, particularly an antineoplastic.

The invention in another aspect is a pharmaceutical composition which includes an isolated nucleic acid molecule selected from the group consisting of: (1) NA Group 1 molecules, and (2) NA Group 2 molecules, and a pharmaceutically acceptable carrier. In one embodiment the isolated nucleic acid molecule comprises a NA Group 3 or NA Group 4 molecule. In another embodiment the isolated nucleic acid molecule comprises at least two isolated nucleic acid molecules coding for two different polypeptides, each polypeptide comprising a different cancer associated antigen. In preferred embodiments, at least one of the polypeptides is encoded by a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12.

Preferably the pharmaceutical composition also includes an expression vector with a promoter operably linked to the isolated nucleic acid molecule. In another embodiment the pharmaceutical composition also includes a host cell recombinantly expressing the isolated nucleic acid molecule.

According to another aspect of the invention a pharmaceutical composition is provided. The pharmaceutical composition includes an isolated polypeptide comprising a PP Group 1 or a PP Group 2 polypeptide, and a pharmaceutically acceptable carrier. In one embodiment the isolated polypeptide comprises a PP Group 3 or a PP Group 4 polypeptide.

In another embodiment the isolated polypeptide comprises at least two different polypeptides, each comprising a different cancer associated antigen at least one of which is encoded by a NA group 1 molecule as disclosed herein. In certain embodiments at least one of the polypeptides is encoded by a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12. In separate embodiments the isolated polypeptides are selected from the following: PP Group 3 polypeptides or HLA binding fragments thereof and PP Group 5 polypeptides or HLA binding fragments thereof.

In an embodiment each of the pharmaceutical compositions described herein also includes an adjuvant.

Another aspect the invention is an isolated nucleic acid molecule comprising a NA Group 3 molecule. Another aspect the invention is an isolated nucleic acid molecule comprising a NA Group 4 molecule.

The invention in another aspect is an isolated nucleic acid molecule selected from the group consisting of (a) a fragment of a nucleic acid selected from the group of nucleic acid molecules consisting of SEQ ID Nos numbered below and comprising all nucleic acid sequences among SEQ ID Nos:3-17, of sufficient length to represent a sequence unique within the human genome, and identifying a nucleic acid encoding a human cancer associated antigen precursor, (b) complements of (a), provided that the fragment includes a sequence of contiguous nucleotides which is not identical to any sequence selected from the sequence group consisting of (1) sequences having the GenBank accession numbers of Table 4, (2) complements of (1), and (3) fragments of (1) and (2).

In one embodiment the sequence of contiguous nucleotides is selected from the group consisting of: (1) at least two contiguous nucleotides nonidentical to the sequences in Table 4, (2) at least three contiguous nucleotides nonidentical to the sequences in Table 4, (3) at least four contiguous nucleotides nonidentical to the sequences in Table 4, (4) at least five contiguous nucleotides nonidentical to the sequences in Table 4, (5) at least six contiguous nucleotides nonidentical to the sequences in Table 4, or (6) at least seven contiguous nucleotides nonidentical to the sequences in Table 4.

In another embodiment the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 50 nucleotides, 75 nucleotides, 100 nucleotides, 200 nucleotides, 1000 nucleotides and every integer length therebetween.

In yet another embodiment the molecule encodes a polypeptide which, or a fragment of which, binds a human HLA receptor or a human antibody.

Another aspect of the invention is an expression vector comprising an isolated nucleic acid molecule of the invention described above operably linked to a promoter.

According to one aspect the invention is an expression vector comprising a nucleic acid operably linked to a promoter, wherein the nucleic acid is a NA Group 1 or Group 2 molecule. In another aspect the invention is an expression vector comprising a NA Group 1 or Group 2 molecule and a nucleic acid encoding an MHC, preferably HLA, molecule.

In yet another aspect the invention is a host cell transformed or transfected with an expression vector of the invention described above.

In another aspect the invention is a host cell transformed or transfected with an expression vector comprising an isolated nucleic acid molecule of the invention described above operably linked to a promoter, or an expression vector comprising a nucleic acid operably linked to a promoter, wherein the nucleic acid is a NA Group 1 or 2 molecule and further comprising a nucleic acid encoding HLA.

According to another aspect of the invention an isolated polypeptide encoded by the isolated nucleic acid molecules the invention, described above, is provided. These include PP Group 1-5 polypeptides. The invention also includes a fragment of the polypeptide which is immunogenic. In one embodiment the fragment, or a portion of the fragment, binds HLA or a human antibody. In still another aspect the invention provides as isolated polypeptide comprising a fragment of a polypeptide selected from the group consisting of ZIC2, SOX1, SOX2, SOX3 and SOX21 polypeptides, which is immunogenic, wherein the polypeptide is not a full-length ZIC1, SOX1, SOX2, SOX3 or SOX21 polypeptide.

The invention includes in another aspect an isolated fragment of a human cancer associated antigen precursor which, or portion of which, binds HLA or a human antibody, wherein the precursor is encoded by a nucleic acid molecule that is a NA Group 1 molecule. In one embodiment the fragment is part of a complex with HLA. In another embodiment the fragment is between 8 and 12 amino acids in length. In another embodiment the invention includes an isolated polypeptide comprising a fragment of the polypeptide of sufficient length to represent a sequence unique within the human genome and identifying a polypeptide that is a human cancer associated antigen precursor.

According to another aspect of the invention a kit for detecting the presence of the expression of a cancer associated antigen precursor is provided. The kit includes a pair of isolated nucleic acid molecules each of which consists essentially of a molecule selected from the group consisting of (a) a 12-32 nucleotide contiguous segment of the nucleotide sequence of any of the NA Group 1 molecules and (b) complements of ("a"), wherein the contiguous segments are nonoverlapping. In one embodiment the pair of isolated nucleic acid molecules is constructed and arranged to selectively amplify an isolated nucleic acid molecule that is a NA Group 3 molecule. Preferably, the pair amplifies a human NA Group 3 molecule.

According to another aspect of the invention a method for treating a subject with a disorder characterized by expression of a human cancer associated antigen precursor is provided. The method includes the step of administering to the subject an amount of an agent, which enriches selectively in the subject the presence of complexes of an HLA molecule and a human cancer associated antigen, effective to ameliorate the disorder, wherein the human cancer associated antigen is a fragment of a human cancer associated antigen precursor encoded by a nucleic acid molecule selected from the group consisting of (a) a nucleic acid molecule comprising NA group 1 nucleic acid molecules, (b) a nucleic acid molecule comprising NA group 3 nucleic acid molecules, (c) a nucleic acid molecule comprising NA group 5 nucleic acid molecules.

In one embodiment the disorder is characterized by expression of a plurality of human cancer associated antigen precursors and wherein the agent is a plurality of agents, each of which enriches selectively in the subject the presence of complexes of an HLA molecule and a different human cancer associated antigen. Preferably the plurality is at least 2, at least 3, at least 4, or at least 5 such agents. In a preferred embodiment, at least one of the human cancer ssociated antigens is a polypeptide encoded by a nucleic acid molecule selected from the roup consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12, or a fragment thereof.

In another embodiment the agent is an isolated polypeptide selected from the group consisting of PP Group 1, PP Group 2, PP Group 3, PP Group 4, and PP group 5 polypeptides.

In yet another embodiment the disorder is cancer.

According to another aspect the invention is a method for treating a subject having a condition characterized by expression of a cancer associated antigen precursor in cells of the subject. The method includes the steps of (i) removing an immunoreactive cell containing sample from the subject, (ii) contacting the immunoreactive cell containing sample to the host cell under conditions favoring production of cytolytic T cells against a human cancer associated antigen which is a fragment of the precursor, (iii) introducing the cytolytic T cells to the subject in an amount effective to lyse cells which express the human cancer associated antigen, wherein the host cell is transformed or transfected with an expression vector comprising an isolated nucleic acid molecule operably linked to a promoter, the isolated nucleic acid molecule being selected from the group of nucleic acid molecules consisting of NA Group 1, NA Group 2, NA Group 3, NA Group 4, NA Group 5.

In one embodiment the host cell recombinantly expresses an HLA molecule which binds the human cancer associated antigen. In another embodiment the host cell endogenously expresses an HLA molecule which binds the human cancer associated antigen.

The invention includes in another aspect a method for treating a subject having a condition characterized by expression of a cancer associated antigen precursor in cells of the subject. The method includes the steps of (i) identifying a nucleic acid molecule expressed by the cells associated with said condition, wherein said nucleic acid molecule is a NA Group 1 molecule (ii) transfecting a host cell with a nucleic acid selected from the group consisting of (a) the nucleic acid molecule identified, (b) a fragment of the nucleic acid identified which includes a segment coding for a cancer associated antigen, (c) deletions, substitutions or additions to (a) or (b), and (d) degenerates of (a), (b), or (c); (iii) culturing said transfected host cells to express the transfected nucleic acid molecule, and; (iv) introducing an amount of said host cells or an extract thereof to the subject effective to increase an immune response against the cells of the subject associated with the condition. Preferably, the antigen is a human antigen and the subject is a human. In certain preferred embodiments the nucleic acid molecule is selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule is selected from the group consisting of SEQ ID NO:3, SEQ ID NO:4, SEQ ID NO:5, SEQ ID NO:11 and SEQ ID NO:12.

In one embodiment the method also includes the step of (a) identifying an MHC molecule which presents a portion of an expression product of the nucleic acid molecule, wherein the host cell expresses the same MHC molecule as identified in (a) and wherein the host cell presents an MHC binding portion of the expression product of the nucleic acid molecule.

In another embodiment the method also includes the step of treating the host cells to render them non-proliferative.

In yet another embodiment the immune response comprises a B-cell response or a T cell response. Preferably the response is a T-cell response which comprises generation of cytolytic T-cells specific for the host cells presenting the portion of the expression product of the nucleic acid molecule or cells of the subject expressing the human cancer associated antigen.

In another embodiment the nucleic acid molecule is a NA Group 3 molecule.

Another aspect of the invention is a method for treating or diagnosing or monitoring a subject having a condition characterized by expression of an abnormal amount of a protein encoded by a nucleic acid molecule that is a NA Group 1 molecule. The method includes the step of administering to the subject an antibody which specifically binds to the protein or a peptide derived therefrom, the antibody being coupled to a therapeutically useful agent, in an amount effective to treat the condition.

In one embodiment the antibody is a monoclonal antibody. Preferably the monoclonal antibody is a chimeric antibody or a humanized antibody.

In another aspect the invention is a method for treating a condition characterized by expression in a subject of abnormal amounts of a protein encoded by a nucleic acid molecule that is a NA Group 1 nucleic acid molecule. The method involves the step of administering to a subject at least one of the pharmaceutical compositions of the invention described above in an amount effective to prevent, delay the onset of, or inhibit the condition in the subject. In one embodiment the condition is cancer. In another embodiment the method includes the step of first identifying that the subject expresses in a tissue abnormal amounts of the protein.

The invention in another aspect is a method for treating a subject having a condition characterized by expression of abnormal amounts of a protein encoded by a nucleic acid molecule that is a NA Group 1 nucleic acid molecule. The method includes the steps of (i) identifying cells from the subject which express abnormal amounts of the protein; (ii) isolating a sample of the cells; (iii) cultivating the cells, and (iv) introducing the cells to the subject in an amount effective to provoke an immune response against the cells.

In one embodiment the method includes the step of rendering the cells non-proliferative, prior to introducing them to the subject.

In another aspect the invention is a method for treating a pathological cell condition characterized by abnormal expression of a protein encoded by a nucleic acid molecule that is a NA Group 1 nucleic acid molecule. The method includes the step of administering to a subject in need thereof an effective amount of an agent which inhibits the expression or activity of the protein.

In one embodiment the agent is an inhibiting antibody which selectively binds to the protein and wherein the antibody is a monoclonal antibody, a chimeric antibody, a humanized antibody or a fragment thereof. In another embodiment the agent is an antisense nucleic acid molecule which selectively binds to the nucleic acid molecule which encodes the protein. In yet another important embodiment the nucleic acid molecule is a NA Group 3 nucleic acid molecule. In other preferred embodiments, the nucleic acid molecule is a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12.

The invention includes in another aspect a composition of matter useful in stimulating an immune response to a plurality of proteins encoded by nucleic acid molecules that are NA Group 1 molecules. The composition is a plurality of peptides derived from the amino acid sequences of the proteins, wherein the peptides bind to one or more MHC molecules presented on the surface of the cells which express an abnormal amount of the protein. In preferred embodiments, at least one of the proteins is encoded by a nucleic acid molecule selected from the group consisting of SOX2 nucleic acids, SOX1 nucleic acids, ZIC2 nucleic acids, SOX3 nucleic acids and SOX21 nucleic acids, and preferably at least one of which is a nucleic acid molecule selected from the group consisting of SEQ ID NO:3, SEQ ID NO:4, SEQ ID NO:5, SEQ ID NO:11 and SEQ ID NO:12.

In one embodiment at least a portion of the plurality of peptides bind to MHC molecules and elicit a cytolytic response thereto. In another embodiment the composition of matter includes an adjuvant. In another embodiment the adjuvant is a saponin, GM-CSF, or an interleukin. In still another embodiment, the compositions also includes at least one peptide useful in stimulating an immune response to at least one protein which is not encoded by nucleic acid molecules that are NA Group 1 molecules, wherein the at least one peptide binds to one or more MHC molecules.

According to another aspect the invention is an isolated antibody which selectively binds to a complex of: (i) a peptide derived from a protein encoded by a nucleic acid molecule that is a NA Group 1 molecule and (ii) and an MHC molecule to which binds the peptide to form the complex, wherein the isolated antibody does not bind to (i) or (ii) alone.

In one embodiment the antibody is a monoclonal antibody, a chimeric antibody, a humanized antibody or a fragment thereof.

The invention also involves the use of the genes, gene products, fragments thereof, agents which bind thereto, and so on in the preparation of medicaments. A particular medicament is for treating cancer and a more particular medicament is for treating small cell lung cancer.

For all of the foregoing, preferred disorders include cancers, particularly lung cancers including small cell lung cancer and non-small cell lung cancer, melanoma, colon cancer, breast cancer, head and neck cancer, transitional cancer, leiomyosarcoma and synovial sarcoma. Preferred tissues include non-brain, non-testis, non-prostate, non-small intestine and non-colon tissues.

These and other aspects of the invention will be described in further detail in connection with the detailed description of the invention.

BRIEF DESCRIPTION OF THE FIGURE

FIG. 1 shows the alignment of predicted protein sequences of SOX1, 2, 3 and 21 (GenBank accession numbers O00570, P48431, P41225, AAC95381.1, respectively; SEQ ID Nos:18-21). Sequences encoded within the SEREX-isolated clones are in bold face type, and sequences absent in these clones are in gray italics. The DNA-binding HMG domain is boxed. Amino acids identical between three and four SOX proteins are highlighted in two shades of gray.

DETAILED DESCRIPTION OF THE INVENTION

In the above summary and in the ensuing description, lists of sequences are provided. The lists are meant to embrace each single sequence separately, two or more sequences together where they form a part of the same gene, any combination of two or more sequences which relate to different genes, including and up to the total number on the list, as if each and every combination were separately and specifically enumerated. Likewise, when mentioning fragment size, it is intended that a range embrace the smallest fragment mentioned to the full-length of the sequence (less one nucleotide or amino acid so that it is a fragment), each and every fragment length intended as if specifically enumerated. Thus, if a fragment could be between 10 and 15 in length, it is explicitly meant to mean 10, 11, 12, 13, 14, or 15 in length.

The summary and the claims mention antigen precursors and antigens. As used in the summary and in the claims, a precursor is substantially the full-length protein encoded by the coding region of the isolated DNA and the antigen is a peptide which complexes with MHC, preferably HLA, and which participates in the immune response as part of that complex. Such antigens are typically 9 amino acids long, although this may vary slightly.

As used herein, a subject is a human, non-human primate, cow, horse, pig, sheep, goat, dog, cat or rodent. In all embodiments human cancer antigens and human subjects are preferred.

The present invention in one aspect involves the cloning of cDNAs encoding human small cell lung cancer associated antigen precursors using autologous antisera of subjects having cancer. The sequences of the clones representing genes identified according to the methods described herein are presented in the attached Sequence Listing. Of the foregoing, it can be seen that some of the clones are novel but may have some homology to sequences deposited in databases (mainly EST sequences). Nevertheless, the entire gene sequence was not previously known. In some cases no function was suspected and in other cases, even if a function was suspected, it was not know that the gene was associated with cancer. In all cases, it was not known or suspected that the gene encoded a cancer antigen which reacted with antibody from autologous sera. Analysis of the clone sequences by comparison to nucleic acid and protein databases determined that still other of the clones surprisingly are closely related to other previously-cloned genes. The sequences of these related genes is also presented in the Sequence Listing. The nature of the foregoing genes as encoding antigens recognized by the immune systems of cancer patients is, of course, unexpected.

The invention thus involves in one aspect cancer associated antigen polypeptides, genes encoding those polypeptides, functional modifications and variants of the foregoing, useful fragments of the foregoing, as well as diagnostics and therapeutics relating thereto.

Homologs and alleles of the cancer associated antigen nucleic acids of the invention can be identified by conventional techniques. Thus, an aspect of the invention is those nucleic acid sequences which code for cancer associated antigen precursors. Because this application contains so many sequences, the following chart is provided to identify the various groups of sequences discussed in the claims and in the summary:

Nucleic Acid Sequences

NA Group 1.
  (a) nucleic acid molecules which hybridize under stringent conditions to a molecule consisting of a nucleic acid sequence selected from the group consisting of SEQ ID NOs: 3-17 and which code for a cancer associated antigen precursor,
  (b) deletions, additions and substitutions which code for a respective cancer associated antigen precursor,
  (c) nucleic acid molecules that differ from the nucleic acid molecules of (a) or (b) in codon sequence due to the degeneracy of the genetic code, and
  (d) complements of (a), (b) or (c).
NA Group 2. Fragments of NA Group 1, which code for a polypeptide which, or a portion of which, binds a MHC molecule to form a complex recognized by an autologous antibody or lymphocyte.
NA Group 3. The subset of NA Group 1 where the nucleotide sequence is selected from the group consisting of:
  (a) previously unknown human nucleic acids coding for a human cancer associated antigen precursor set forth as SEQ ID NO:17,
  (b) deletions, additions and substitutions which code for a respective human cancer associated antigen precursor,
  (c) nucleic acid molecules that differ from the nucleic acid molecules of (a) or (b) in codon sequence due to the degeneracy of the genetic code, and
  (d) complements of (a), (b) or (c).
NA Group 4. Fragments of NA Group 3, which code for a polypeptide which, or a portion of which, binds to a MHC molecule to form a complex recognized by an autologous antibody or lymphocyte.
NA Group 5. A subset of NA Group 1, comprising human cancer associated antigens that react with allogeneic cancer antisera.

Polypeptide Sequences

PP Group 1. Polypeptides encoded by NA Group 1.
PP Group 2. Polypeptides encoded by NA Group 2
PP Group 3. Polypeptides encoded by NA Group 3.
PP Group 4. Polypeptides encoded by NA Group 4.
PP Group 5. Polypeptides encoded by NA Group 5.

The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of cancer associated antigen nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to the sequences of cancer associated antigen nucleic acid and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://www.ncbi.nlm.nih.gov, using default settings. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for cancer associated antigen genes, a Southern blot may be performed using the foregoing conditions, together with a radioactive probe. After washing the membrane to which the DNA is finally transferred, the membrane can be placed against X-ray film to detect the radioactive signal. In screening for the expression of cancer associated antigen nucleic acids, Northern blot hybridizations using the foregoing conditions (see also the Examples) can be performed on samples taken from breast cancer patients or subjects suspected of having a condition characterized by expression of breast cancer associated antigen genes. Amplification protocols such as polymerase chain reaction using primers which hybridize to the sequences presented also can be used for detection of the cancer associated antigen genes or expression thereof.

The small cell lung cancer associated genes correspond to SEQ ID NOs. 3-17. The preferred cancer associated antigens for the methods of diagnosis disclosed herein are those which were found to react with allogeneic cancer antisera (i.e. NA Group 5). Especially preferred are the ZIC2 and SOX Group B sequences (SEQ ID Nos: 3, 4, 5, 11 and 12). Encoded polypeptides (e.g., SEQ ID NOS:18-22), peptides and antisera thereto are also preferred for diagnosis.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating breast cancer associated antigen polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, enzymatic activity, receptor binding, formation of complexes by binding of peptides by MHC class I and class II molecules, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated unique fragments of cancer associated antigen nucleic acid sequences or complements thereof. A unique fragment is one that is a 'signature' for the larger nucleic acid. It, for example, is long enough to assure that its precise sequence is not found in molecules within the human genome outside of the cancer associated antigen nucleic acids defined above (and human alleles).

Those of ordinary skill in the art may apply no more than routine procedures to determine if a fragment is unique within the human genome. Unique fragments, however, exclude fragments completely composed of the nucleotide sequences of any of GenBank accession numbers listed in Table 4 or other previously published sequences as of the filing date of the priority documents for sequences listed in a respective priority document or the filing date of this application for sequences listed for the first time in this application which overlap the sequences of the invention.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of the cancer associated antigen polypeptides, useful, for example, in the preparation of antibodies, and in immunoassays. Unique fragments further can be used as antisense molecules to inhibit the expression of cancer associated antigen nucleic acids and polypeptides, particularly for therapeutic purposes as described in greater detail below.

As will be recognized by those skilled in the art, the size of the unique fragment will depend upon its conservancy in the genetic code. Thus, some regions of cancer associated antigen sequences and complements thereof will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 or more bases long, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide (provided the sequence is unique as described above).

Virtually any segment of the polypeptide coding region of novel cancer associated antigen nucleic acids, or complements thereof, that is 18 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

Especially preferred include nucleic acids encoding a series of epitopes, known as "polytopes". The epitopes can be arranged in sequential or overlapping fashion (see, e.g., Thomson et al., *Proc. Natl. Acad. Sci. USA* 92:5845-5849, 1995; Gilbert et al., *Nature Biotechnol.* 15:1280-1284, 1997), with or without the natural flanking sequences, and can be separated by unrelated linker sequences if desired. The polytope is processed to generate individual epitopes which are recognized by the immune system for generation of immune responses.

Thus, for example, peptides derived from a polypeptide having an amino acid sequence encoded by one of the nucleic acid disclosed herein, and which are presented by MHC molecules and recognized by CTL or T helper lymphocytes, can be combined with peptides from one or more other cancer associated antigens (e.g. by preparation of hybrid nucleic acids or polypeptides) to form "polytopes". The two or more peptides (or nucleic acids encoding the peptides) can be selected from those described herein, or they can include one or more peptides of previously known cancer associated antigens. Exemplary cancer associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-1, GAGE-2, GAGE-3, GAGE-4, GAGE-5, GAGE-6, GAGE-7, GAGE-8, GAGE-9, BAGE-1, RAGE-1, LB33/MUM-1, PRAME, NAG, MAGE-B2, MAGE-B3, MAGE-B4, tyrosinase, brain glycogen phosphorylase, Melan-A, MAGE-C1, MAGE-C2, MAGE-C3, MAGE-C4, MAGE-C5, NY-ESO-1, LAGE-1, SSX-1, SSX-2 (HOM-MEL-40), SSX-4, SSX-5, SCP-1 and CT-7. See, for example, PCT application publication no. WO96/10577. Other examples will be known to one of ordinary skill in the art and can be used in the invention in a like manner as those disclosed herein.

Other examples of HLA class I and HLA class II binding peptides will be known to one of ordinary skill in the art. For example, see the following references: Coulie, *Stem Cells* 13:393-403, 1995; Traversari et al., *J. Exp. Med.* 176:1453-1457, 1992; Chaux et al., *J. Immunol.* 163:2928-2936, 1999; Fujie et al., *Int. J. Cancer* 80:169-172, 1999; Tanzarella et al., *Cancer Res.* 59:2668-2674, 1999; van der Bruggen et al., *Eur. J. Immunol.* 24:2134-2140, 1994; Chaux et al., *J. Exp. Med.* 189:767-778, 1999; Kawashima et al, *Hum. Immunol.* 59:1-14, 1998; Tahara et al., *Clin. Cancer Res.* 5:2236-2241, 1999; Gaugler et al., *J. Exp. Med.* 179:921-930, 1994; van der Bruggen et al., *Eur. J. Immunol.* 24:3038-3043, 1994; Tanaka et al., *Cancer Res.* 57:4465-4468, 1997; Oiso et al., *Int. J. Cancer* 81:387-394, 1999; Herman et al., *Immunogenetics* 43:377-383, 1996; Manici et al., *J. Exp. Med.* 189:871-876, 1999; Duffour et al., *Eur. J. Immunol.* 29:3329-3337, 1999; Zom et al., *Eur. J. Immunol.* 29:602-607, 1999; Huang et al., *J. Immunol.* 162:6849-6854, 1999; Boël et al., *Immunity* 2:167-175, 1995; Van den Eynde et al., *J. Exp. Med.* 182:689-698, 1995; De Backer et al., *Cancer Res.* 59:3157-3165, 1999; Jager et al., *J. Exp. Med.* 187: 265-270, 1998; Wang et al., *J. Immunol.* 161:3596-3606, 1998; Aarnoudse et al., *Int. J. Cancer* 82:442-448, 1999; Guilloux et al., *J. Exp. Med.* 183:1173-1183, 1996; Lupetti et al., *J. Exp. Med.* 188:1005-1016, 1998; Wölfel et al., *Eur. J. Immunol.* 24:759-764, 1994; Skipper et al., *J. Exp. Med.* 183:527-534, 1996; Kang et al., *J. Immunol.* 155:1343-1348, 1995; Morel et al., *Int. J. Cancer* 83:755-759, 1999; Brichard et al., *Eur. J. Immunol.* 26:224-230, 1996; Kittlesen et al., *J. Immunol.* 160:2099-2106, 1998; Kawakami et al., *J. Immunol.* 161:6985-6992, 1998; Topalian et al., *J. Exp. Med.* 183:1965-1971, 1996; Kobayashi et al., *Cancer Research* 58:296-301, 1998; Kawakami et al., *J. Immunol.* 154:3961-3968, 1995; Tsai et al., *J. Immunol.* 158:1796-

1802, 1997; Cox et al., *Science* 264:716-719, 1994; Kawakami et al., *Proc. Natl. Acad. Sci. USA* 91:6458-6462, 1994; Skipper et al., *J. Immunol.* 157:5027-5033, 1996; Robbins et al., *J. Immunol.* 159:303-308, 1997; Castelli et al, *J. Immunol.* 162:1739-1748, 1999; Kawakami et al., *J. Exp. Med.* 180:347-352, 1994; Castelli et al., *J. Exp. Med.* 181: 363-368, 1995; Schneider et al., *Int. J. Cancer* 75:451-458, 1998; Wang et al., *J. Exp. Med.* 183:1131-1140, 1996; Wang et al., *J. Exp. Med.* 184:2207-2216, 1996; Parkhurst et al., *Cancer Research* 58:4895-4901, 1998; Tsang et al., *J. Natl Cancer Inst* 87:982-990, 1995; Correale et al., *J Natl Cancer Inst* 89:293-300, 1997; Coulie et al., *Proc. Natl. Acad. Sci. USA* 92:7976-7980, 1995; Wölfel et al., *Science* 269:1281-1284, 1995; Robbins et al., *J. Exp. Med.* 183:1185-1192, 1996; Brandle et al., *J. Exp. Med.* 183:2501-2508, 1996; ten Bosch et al., *Blood* 88:3522-3527, 1996; Mandruzzato et al., *J. Exp. Med.* 186:785-793, 1997; Gueguen et al., *J. Immunol.* 160:6188-6194, 1998; Gjertsen et al., *Int. J. Cancer* 72:784-790, 1997; Gaudin et al., *J. Immunol.* 162:1730-1738, 1999; Chiari et al., *Cancer Res.* 59:5785-5792, 1999; Hogan et al., *Cancer Res.* 58:5144-5150, 1998; Pieper et al., *J. Exp. Med.* 189:757-765, 1999; Wang et al., *Science* 284:1351-1354, 1999; Fisk et al., *J. Exp. Med.* 181:2109-2117, 1995; Brossart et al., *Cancer Res.* 58:732-736, 1998; Ropke et al., *Proc. Natl. Acad. Sci. USA* 93:14704-14707, 1996; Ikeda et al., *Immunity* 6:199-208, 1997; Ronsin et al., *J. Immunol.* 163:483-490, 1999; Vonderheide et al., *Immunity* 10:673-679,1999.

One of ordinary skill in the art can prepare polypeptides comprising one or more peptides and one or more of the foregoing cancer associated peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13): 5845-5849, 1995; Gilbert et al., *Nature Biotechnol.* 15(12): 1280-1284, 1997; Thomson et al., *J. Immunol.* 157(2):822-826, 1996; Tam et al., *J. Exp. Med.* 171(1):299-306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951-1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

In instances in which a human HLA class I molecule presents tumor rejection antigens derived from cancer associated nucleic acids, the expression vector may also include a nucleic acid sequence coding for the HLA molecule that presents any particular tumor rejection antigen derived from these nucleic acids and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for a cancer associated antigen precursor and the HLA molecule which presents it are contained on separate expression vectors, the expression vectors can be cotransfected. The cancer associated antigen precursor coding sequence may be used alone, when, e.g. the host cell already expresses a HLA molecule which presents a cancer associated antigen derived from precursor molecules. Of course, there is no limit on the particular host cell which can be used. As the vectors which contain the two coding sequences may be used in any antigen-presenting cells if desired, and the gene for cancer associated antigen precursor can be used in host cells which do not express a HLA molecule which presents a cancer associated antigen. Further, cell-free transcription systems may be used in lieu of cells.

As mentioned above, the invention embraces antisense oligonucleotides that selectively bind to a nucleic acid molecule encoding a cancer associated antigen polypeptide, to reduce the expression of cancer associated antigens. This is desirable in virtually any medical condition wherein a reduction of expression of cancer associated antigens is desirable, e.g., in the treatment of cancer. This is also useful for in vitro or in vivo testing of the effects of a reduction of expression of one or more cancer associated antigens.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that MRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the sequences of nucleic acids encoding breast cancer associated antigen, or upon allelic or homologous genomic and/or cDNA sequences, one of skill in the art can easily choose and synthesize any of a number of appropriate antisense molecules for use in accordance with the present invention.

In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840-844, 1996). Most preferably, the antisense oligonucleotides comprise a complementary sequence of 20-30 bases. Although oligonucleotides may be chosen which are antisense to any region of the gene or MRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to MRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439-457, 1994) and at which proteins are not expected to bind. Finally, although the listed sequences are cDNA sequences, one of ordinary skill in the art may easily derive the genomic DNA corresponding to the cDNA of a cancer associated antigen. Thus, the present invention also provides for antisense oligonucleotides which are complementary to the genomic DNA corresponding to nucleic acids encoding cancer associated antigens. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic intemucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Base analogs such as C-5 propyne modified bases also can be included (*Nature Biotechnol.* 14:840-844, 1996). The present invention, thus, contemplates pharmaceutical preparations containing modified antisense molecules that are complementary to and hybridizable with, under physiological conditions, nucleic acids encoding the cancer associated antigen polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers., and other materials which are well known in the art, as further described below.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a breast cancer associated antigen polypeptide or fragment or variant thereof. That heterologous DNA (RNA) is placed under operable control of transcriptional elements to permit the expression of the heterologous DNA in the host cell.

Preferred systems for MRNA expression in mammalian cells are those such as pRc/CMV (available from Invitrogen, Carlsbad, CA) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr Virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant for the expression of an antigen is disclosed by Wamier et al., in intradermal injection in mice for immunization against PIA (*Int. J. Cancer,* 67:303-310, 1996). Additional vectors for delivery of nucleic acid are provided below.

The invention also embraces so-called expression kits, which allow the artisan to prepare a desired expression vector or vectors. Such expression kits include at least separate portions of a vector and one or more of the previously discussed cancer associated antigen nucleic acid molecules. Other components may be added, as desired, as long as the previously mentioned nucleic acid molecules, which are required, are included. The invention also includes kits for amplification of a cancer associated antigen nucleic acid, including at least one pair of amplification primers which hybridize to a cancer associated antigen nucleic acid. The primers preferably are 12-32 nucleotides in length and are non-overlapping to prevent formation of "primer-dimers". One of the primers will hybridize to one strand of the cancer associated antigen nucleic acid and the second primer will hybridize to the complementary strand of the cancer associated antigen nucleic acid, in an arrangement which permits amplification of the cancer associated antigen nucleic acid. Selection of appropriate primer pairs is standard in the art. For example, the selection can be made with assistance of a computer program designed for such a purpose, optionally followed by testing the primers for amplification specificity and efficiency.

The invention also permits the construction of cancer associated antigen gene "knock-outs" in cells and in animals, providing materials for studying certain aspects of cancer and immune system responses to cancer.

The invention also provides isolated polypeptides (including whole proteins and partial proteins) encoded by the foregoing cancer associated antigen nucleic acids. Such polypeptides are useful, for example, alone or as fusion proteins to generate antibodies, as components of an immunoassay or diagnostic assay or as therapeutics. Cancer associated antigen polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of a cancer associated antigen polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of cancer associated antigens will require longer segments to be unique while others will require only short segments, typically between 5 and 12 amino acids (e.g. 5, 6, 7, 8, 9, 10, 11 or 12 or more amino acids including each integer up to the full length).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding of nucleic acids or proteins, and enzymatic activity. One important activity is the ability to act as a signature for identifying the polypeptide. Another is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the cancer associated antigen polypeptides described above. As used herein, a "variant" of a cancer associated antigen polypeptide is a polypeptide which contains one or more modifications to the primary amino acid sequence of a cancer associated antigen polypeptide. Modifications which create a cancer associated antigen variant can be made to a cancer associated antigen polypeptide 1) to reduce or eliminate an activity of a cancer associated antigen polypeptide; 2) to enhance a property of a cancer associated antigen polypeptide, such as protein stability in an expression system or the stability of protein-protein binding; 3) to provide a novel activity or property to a cancer associated antigen polypeptide, such as addition of an antigenic epitope or addition of a detectable moiety; or 4) to provide equivalent or better binding to an HLA molecule. Modifications to a cancer associated antigen polypeptide are typically made to the nucleic acid which encodes the cancer associated antigen polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the cancer associated antigen amino acid sequence. One of skill in the art will be familiar with methods for predicting the effect on protein conformation of a change in protein sequence, and can thus "design" a variant cancer associated antigen polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

In general, variants include cancer associated antigen polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a breast cancer associated antigen polypeptide by eliminating proteolysis by proteases in an expression system (e.g., dibasic amino acid residues in yeast expression systems in which KEX2 protease activity is present).

Mutations of a nucleic acid which encode a cancer associated antigen polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant cancer associated antigen polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a cancer associated antigen gene or cDNA clone to enhance expression of the polypeptide. The activity of variants of cancer associated antigen polypeptides can be tested by cloning the gene encoding the variant cancer associated antigen polypeptide into a bacterial or mammalian expression vector, introducing the vector into an appropriate host cell, expressing the variant cancer associated antigen polypeptide, and testing for a functional capability of the cancer associated antigen polypeptides as disclosed herein. For example, the variant cancer associated antigen polypeptide can be tested for reaction with autologous or allogeneic sera as disclosed in the Examples. Preparation of other variant polypeptides may favor testing of other activities, as will be known to one of ordinary skill in the art.

The skilled artisan will also realize that conservative amino acid substitutions may be made in cancer associated antigen polypeptides to provide functionally equivalent variants of the foregoing polypeptides, i.e, the variants retain the functional capabilities of the cancer associated antigen polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the cancer associated antigen polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide derived from a cancer associated antigen polypeptide is presented by an MHC molecule and recognized by CTLs (e.g., as described in the Examples), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13-18, 1995; Drijfhout et al., *Human Immunol.* 43:1-12, 1995). The substituted peptides can then be tested for binding to the MHC molecule and recognition by CTLs when bound to MHC. These variants can be tested for improved stability and are useful, inter alia, in vaccine compositions.

Conservative amino-acid substitutions in the amino acid sequence of cancer associated antigen polypeptides to produce functionally equivalent variants of cancer associated antigen polypeptides typically are made by alteration of a nucleic acid encoding a cancer associated antigen polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a cancer associated antigen polypeptide. Where amino acid substitutions are made to a small unique fragment of a cancer associated antigen polypeptide, such as an antigenic epitope recognized by autologous or allogeneic sera or cytolytic T lymphocytes, the substitutions can be made by directly synthesizing the peptide. The activity of functionally equivalent fragments of cancer associated antigen polypeptides can be tested by cloning the gene encoding the altered cancer associated antigen polypeptide into a bacterial or mammalian expression vector, introducing the vector into an appropriate host cell, expressing the altered cancer associated antigen polypeptide, and testing for a functional capability of the cancer associated antigen polypeptides as disclosed herein. Peptides which are chemically synthesized can be tested directly for function, e.g., for binding to antisera recognizing associated antigens.

The invention as described herein has a number of uses, some of which are described elsewhere herein. First, the invention permits isolation of the cancer associated antigen protein molecules. A variety of methodologies well-known to the skilled practitioner can be utilized to obtain isolated cancer associated antigen molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating cancer associated antigen polypeptides. These include, but are not limited to, immunochromatography, HPLC, size-exclusion chromatography, ion-exchange chromatography and immune-affinity chromatography.

The isolation and identification of cancer associated antigen genes also makes it possible for the artisan to diagnose a disorder characterized by expression of cancer associated antigens. These methods involve determining expression of one or more cancer associated antigen nucleic acids, and/or encoded cancer associated antigen polypeptides and/or peptides derived therefrom. In the former situation, such determinations can be carried out via any standard nucleic acid determination assay, including the polymerase chain reaction, or assaying with labeled hybridization probes. In the latter situation, such determinations can be carried out by screening patient antisera for recognition of the polypeptide.

The invention also makes it possible isolate proteins which bind to cancer associated antigens as disclosed herein, including antibodies and cellular binding partners of the cancer associated antigens. Additional uses are described further herein.

The invention also provides, in certain embodiments, "dominant negative" polypeptides derived from cancer associated antigen polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of small cell lung cancer associated antigens, especially those which are similar to known proteins which have known activities, one of ordinary skill in the art can modify the sequence of the cancer associated antigens by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The invention also involves agents such as polypeptides which bind to cancer associated antigen polypeptides. Such binding agents can be used, for example, in screening assays to detect the presence or absence of cancer associated antigen polypeptides and complexes of cancer associated antigen polypeptides and their binding partners and in purification protocols to isolated cancer associated antigen polypeptides and complexes of cancer associated antigen polypeptides and their binding partners. Such agents also can be used to inhibit the native activity of the cancer associated antigen polypeptides, for example, by binding to such polypeptides.

The invention, therefore, embraces peptide binding agents which, for example, can be antibodies or fragments of antibodies having the ability to selectively bind to cancer associated antigen polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to cancer associated antigen polypeptides, and complexes of both cancer associated antigen polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the cancer associated antigen polypeptide. This process can be repeated through several cycles of reselection of phage that bind to the cancer associated antigen polypeptide. Repeated rounds lead to enrichment of phage bearing particular sequences. DNA sequence analysis can be conducted to identify the sequences of the expressed polypeptides. The minimal linear portion of the sequence that binds to the cancer associated antigen polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the cancer associated antigen polypeptides. Thus, the cancer associated antigen polypeptides of the invention, or a fragment thereof, can be used to screen peptide libraries, including phage display libraries, to identify and select peptide binding partners of the cancer associated antigen polypeptides of the invention. Such molecules can be used, as described, for screening assays, for purification protocols, for interfering directly with the functioning of cancer associated antigen and for other purposes that will be apparent to those of ordinary skill in the art.

As detailed herein, the foregoing antibodies and other binding molecules may be used for example to identify tissues expressing protein or to purify protein. Antibodies also may be coupled to specific diagnostic labeling agents for imaging of cells and tissues that express cancer associated antigens or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art. As used herein, "therapeutically useful agents" include any therapeutic molecule which desirably is targeted selectively to a cell expressing one of the cancer antigens disclosed herein, including antineoplastic agents, radioiodinated compounds, toxins, other cytostatic or cytolytic drugs, and so forth. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60.

In the foregoing methods, antibodies prepared according to the invention also preferably are specific for the small cell lung cancer associated antigen/MHC complexes described herein.

When "disorder" is used herein, it refers to any pathological condition where the cancer associated antigens are expressed. An example of such a disorder is cancer, with lung cancers including small cell lung cancer and non-small cell lung cancer, melanoma, colon cancer, breast cancer, head and neck cancer, transitional cancer, leiomyosarcoma and synovial sarcoma as particular examples.

Samples of tissue and/or cells for use in the various methods described herein can be obtained through standard methods such as tissue biopsy, including punch biopsy and cell scraping, and collection of blood or other bodily fluids by aspiration or other methods.

In certain embodiments of the invention, an immunoreactive cell sample is removed from a subject. By "immunoreactive cell" is meant a cell which can mature into an immune cell (such as a B cell, a helper T cell, or a cytolytic T cell) upon appropriate stimulation. Thus immunoreactive cells include $CD34^+$ hematopoietic stem cells, immature T cells and immature B cells. When it is desired to produce cytolytic T cells which recognize a cancer associated antigen, the immunoreactive cell is contacted with a cell which expresses a cancer associated antigen under conditions favoring production, differentiation and/or selection of cytolytic T cells; the differentiation of the T cell precursor into a cytolytic T cell upon exposure to antigen is similar to clonal selection of the immune system.

Some therapeutic approaches based upon the disclosure are premised on a response by a subject's immune system, leading to lysis of antigen presenting cells, such as breast cancer cells which present one or more cancer associated antigens. One such approach is the administration of autologous CTLs specific to a cancer associated antigen/MHC complex to a subject with abnormal cells of the phenotype at issue. It is within the ability of one of ordinary skill in the art to develop such CTLs in vitro. An example of a method for T cell differentiation is presented in International Application number PCT/US96/05607. Generally, a sample of cells taken from a subject, such as blood cells, are contacted with a cell presenting the complex and capable of provoking CTLs to proliferate. The target cell can be a transfectant, such as a COS cell. These transfectants present the desired complex of their surface and, when combined with a CTL of interest, stimulate its proliferation. COS cells are widely available, as are other suitable host cells. Specific production of CTL clones is well known in the art. The clonally expanded autologous CTLs then are administered to the subject.

Another method for selecting antigen-specific CTL clones has recently been described (Altman et al., Science 274:94-96, 1996; Dunbar et al., Curr. Biol. 8:413-416, 1998), in which fluorogenic tetramers of MHC class I molecule/peptide complexes are used to detect specific CTL. clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, J. Immunol. 136(5): 1917, 1986; Riddel et al., Science 257: 238, 1992; Lynch et al, Eur. J. Immunol. 21: 1403-1410,1991; Kast et al., Cell 59: 603-614, 1989), cells presenting the desired complex (e.g., dendritic cells) are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/cancer associated antigen complex. This can be determined very easily, as the art is very familiar with methods for identifying cells which present a particular HLA molecule, as well as how to identify cells expressing DNA of the pertinent sequences, in this case a cancer associated antigen sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a cancer associated antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex (i.e. the antigenic peptide and the presenting HLA molecule). Chen et al. (Proc. Natl. Acad. Sci. USA 88: 110-114,1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. For example, nucleic acids which encode a cancer associated antigen polypeptide or peptide may be operably linked to promoter and enhancer sequences which direct expression of the cancer associated antigen polypeptide or peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding cancer associated antigen, as described elsewhere herein. Nucleic acids encoding a cancer associated antigen also may be inserted into a retroviral genome, thereby facilitating integration of the nucleic acid into the genome of the target tissue or cell type. In these systems, the gene of interest is carried by a microorganism, e.g., a Vaccinia virus, pox virus, herpes simplex virus, retrovirus or adenovirus, and the materials de facto "infect" host cells. The cells which result present the complex of interest, and are recognized by autologous CTLs, which then proliferate.

A similar effect can be achieved by combining the cancer associated antigen or a stimulatory fragment thereof with an adjuvant to facilitate incorporation into antigen presenting cells in vivo. The cancer associated antigen polypeptide is processed to yield the peptide partner of the HLA molecule while a cancer associated antigen peptide may be presented without the need for further processing. Generally, subjects can receive an intradermal injection of an effective amount of the cancer associated antigen. Initial doses can be followed by booster doses, following immunization protocols standard in the art. Preferred cancer associated antigens include those found to react with allogeneic cancer antisera, shown in the examples below.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models can be used for testing of immunization against cancer using a cancer associated antigen nucleic acid. For example, human cancer cells can be introduced into a mouse to create a tumor, and one or more cancer associated antigen nucleic acids can be delivered by the methods described herein. The effect on the cancer cells (e.g., reduction of tumor size) can be assessed as a measure of the effectiveness of the cancer associated antigen nucleic acid immunization. Of course, testing of the foregoing animal model using more conventional methods for immunization include the administration of one or more cancer associated antigen polypeptides or peptides derived therefrom, optionally combined with one or more adjuvants and/or cytokines to boost the immune response. Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more cancer associated antigens or stimulatory fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol. Cells* 7:178-186, 1997); incomplete Freund's adjuvant; complete Freund's adjuvant; montanide; and various water-in-oil emulsions prepared from biodegradable oils such as squalene and/or tocopherol. Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432-1434, 1995), GM-CSF and IL-18. Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P., et al. *Proc. Natl. Acad. Sci. USA* 95 (11): 6284-6289 (1998)).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol*, 154:5637-5648 (1995)). Tumor cell transfection with B7 has ben discussed in relation to in vitro CTL expansion for adoptive transfer immunotherapy by Wang et al., (*J. Immunol.*, 19:1-8 (1986)). Other delivery mechanisms for the B7 molecule would include nucleic acid (naked DNA) immunization (Kim J., et al. *Nat Biotechnol.*, 15:7:641-646 (1997)) and recombinant viruses such as adeno and pox (Wendtner et al., *Gene Ther.*, 4:7:726-735 (1997)). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637-642 (1997), Fenton et al., *J. Immunother.*, 21:2:95-108 (1998)).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., *J. Immunother.*, 21:2:95-108 (1998)). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature*, 393:474 (1998), Bennett et al., *Nature*, 393:478 (1998), Schoenberger et al., *Nature*, 393:480 (1998)). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor antigens which are normally encountered outside of a inflammatory context or are presented by non-professional APCs (tumor cells). In these situations Th help and B7 costimulation signals are not provided. This mechanism might be used in the context of antigen pulsed DC based therapies or in situations where Th epitopes have not been defined within known TRA precursors.

A cancer associated antigen polypeptide, or a fragment thereof, also can be used to isolate their native binding partners. Isolation of such binding partners may be performed according to well-known methods. For example, isolated cancer associated antigen polypeptides can be attached to a substrate (e.g., chromatographic media, such as polystyrene beads, or a filter), and then a solution suspected of containing the binding partner may be applied to the substrate. If a binding partner which can interact with cancer associated antigen polypeptides is present in the solution, then it will bind to the substrate-bound cancer associated antigen polypeptide. The binding partner then may be isolated.

It will also be recognized that the invention embraces the use of the cancer associated antigen cDNA sequences in expression vectors, as well as to transfect host cells and cell lines, be these prokaryotic (e.g., *E. coli*), or eukaryotic (e.g., dendritic cells, B cells, CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, peripheral blood leukocytes, bone marrow stem cells and embryonic stem cells. The expression vectors require that the pertinent sequence, i.e., those nucleic acids described supra, be operably linked to a promoter.

The invention also contemplates delivery of nucleic acids, polypeptides or peptides for vaccination. Delivery of polypeptides and peptides can be accomplished according to standard vaccination protocols which are well known in the art. In another embodiment, the delivery of nucleic acid is accomplished by ex vivo methods, i.e. by removing a cell from a subject, genetically engineering the cell to include a breast cancer associated antigen, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

In preferred embodiments, a virus vector for delivering a nucleic acid encoding a cancer associated antigen is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220-227, 1996; Eloit et al., *J. Virol.* 7:5375-5381, 1997; Chengalvala et al., *Vaccine* 15:335-339; 1997), a modified retrovirus (Townsend et al., *J. Virol.* 71:3365-3374, 1997), a nonreplicating retrovirus (Irwin et al., *J. Virol.* 68:5036-5044, 1994), a replication defective Semliki Forest virus (Zhao et al., *Proc. Natl. Acad. Sci. USA* 92:3009-3013, 1995), canarypox virus and highly attenuated vaccinia virus derivative (Paoletti, *Proc. Natl. Acad. Sci. USA* 93:11349-11353, 1996), non-replicative vaccinia virus (Moss, *Proc. Natl. Acad. Sci. USA* 93:11341-11348, 1996), replicative vaccinia virus (Moss, *Dev. Biol. Stand.* 82:55-63, 1994), Venzuelan equine encephalitis virus (Davis et al., *J. Virol.* 70:3781-3787, 1996), Sindbis virus (Pugachev et al., *Virology* 212:587-594, 1995), and Ty virus-like particle (Allsopp et al., *Eur. J. Immunol* 26:1951-1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, New Jersey (1991).

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-CaPO$_4$ precipitates, transfection of nucleic acids associated with DEAE, transfection or infection of the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a cancer associated antigen, alone or as a complex with a MIIC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfuilly to deliver nucleic acids into cells, as is known by those skilled in the art. Such systems even permit oral delivery of nucleic acids.

When administered, the therapeutic compositions of the present invention can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a cancer associated antigen composition that alone, or together with further doses, produces the desired response, e.g. increases an immune response to the cancer associated antigen. In the case of treating a particular disease or condition characterized by expression of one or more cancer associated antigens, such as small cell lung cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of cancer associated antigen or nucleic acid encoding cancer associated antigen for producing the desired response in a unit of weight or volume suitable for administration to a patient. The response can, for example, be measured by determining the immune response following administration of the cancer associated antigen composition via a reporter system by measuring downstream effects such as gene expression, or by measuring the physiological effects of the cancer associated antigen composition, such as regression of a tumor or decrease of disease symptoms. Other assays will be known to one of ordinary skill in the art and can be employed for measuring the level of the response.

The doses of cancer associated antigen compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of cancer associated antigen are formulated and administered in doses between 1 ng and 1 mg, and preferably between 10 ng and 100 µg, according to any standard procedure in the art. Where nucleic acids encoding cancer associated antigen of variants thereof are employed, doses of between 1 ng and 0.1 mg generally will be formulated and administered according to standard procedures. Other protocols for the administration of cancer associated antigen compositions will be known to one of ordinary skill in the art, in which the dose amount, schedule of injections, sites of injections, mode of administration (e.g., intra-tumoral) and the like vary from the foregoing. Administration of cancer associated antigen compositions to mammals other than humans, e.g. for testing purposes or veterinary therapeutic purposes, is carried out under substantially the same conditions as described above.

Where cancer associated antigen peptides are used for vaccination, modes of administration which effectively deliver the cancer associated antigen and adjuvant, such that an immune response to the antigen is increased, can be used. For administration of a cancer associated antigen peptide in adjuvant, preferred methods include intradermal, intravenous, intramuscular and subcutaneous administration. Although these are preferred embodiments, the invention is not limited by the particular modes of administration disclosed herein. Standard references in the art (e.g., *Remington's Pharmaceutical Sciences*, 18th edition, 1990) provide modes of administration and formulations for delivery of immunogens with adjuvant or in a non-adjuvant carrier.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A small cell lung cancer associated antigen composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of breast cancer associated antigen polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

EXAMPLES

Methods and Materials

Cell Lines, Tissues, and Patient Sera

Cell lines were obtained from the repository maintained at the Ludwig Institute for Cancer Research (LICR), New York Branch at the Memorial Sloan-Kettering Cancer Center (MSKCC), or obtained from American Tissue Culture Collection. Eleven SCLC cell lines were used including 9 classical (SK-LC-13, NCI-H69, -H128, -H146, -H187, -H209, -H378, -H889, -H740) and 2 variant (NCI-H82, -H526) forms. The variant SCLC lines differ from the classical lines in lacking or having diminished neuroendocrine features and with regard to other biochemical, morphological and growth properties (Carney et al., $Cancer Res.$ 45:2913-2923, 1985; Park et al., $Cancer Res.$ 47:6710-6718, 1987). Normal and tumor tissues were obtained from the departments of Pathology in the New York Presbyterian Hospital (NYPH) and the MSKCC. Patient sera were obtained from the Department of Medicine, NYPH, and from the LICR Melbourne Branch, Australia.

Immunoscreening of the SCLC Cell Line Libraries and Characterization of Immunoreactive Clones Construction of cDNA expression libraries from the NCI-H740 and SK-LC-13 SCLC cell lines in the λ-ZAP vector (Stratagene) and immunoscreening were done as previously described (Old and Chen, $J. Exp. Med.,$ 187:1163-7, 1998; Chen et al., $Proc. Nat'l. Acad. Sci. USA,$ 95: 6919-23, 1998), with the following modifications. Sera from five SCLC patients (Lu94, Lu100, Lu101, Lu104, Lu113) were pooled and absorbed as previously described Scanlan et al., $Int. J. Cancer$ 76:652-658, 1998). The pooled serum was diluted 1:200 (final dilution 1:1000 for each serum) in TBS containing 1% BSA and 0.02% $NaN_3$ and was used to screen $5.6 \times 10^5$ pfu of the NCI-H740 library. The same serum was used for the SK-LC-13 library of which $2.2 \times 10^5$ pfu was screened. Immunoreactive clones were isolated and sequence analyzed as previously described (Chen et al., 1998). Selected immunoreactive clones were subsequently tested for reactivity against sera at various dilutions from individual lung cancer patients and normals using the same plaque assay. A λ-ZAP clone without an insert was co-plated and included in the screen as a negative control.

RT-PCR Analysis

Reverse transcription was performed with total RNA isolated from tissue or cell lines by the Guanidium thiocyanate/CsCl method. Primers used to amplify ZIC2 were designed based on the published sequence (AF104902) and our results. ZIC2A1:5'-CATGAATATGAACATGGGTAT-GAACATGG (SEQ ID NO:1); ZIC2B1:5'-TCGCAGCCCT-CAAACTCACACTG (SEQ ID NO:2). Conditions for amplification were as follows: Initial denaturation and AmpliTaq Gold (Perkin Elmer) activation; 94° C., 10', Amplification: 94° C., 1'; 60° C., 1'; 72° C., 1'; for 35 cycles, followed by a 6', 72° C. incubation. Amplification products were analyzed by agarose gel electrophoresis and visualized by EtBr staining.

Northern Blot Analysis

Adult normal tissue MRNA blots were obtained from Clontech, Inc. and contained 2 g polyA$^+$ RNA per lane. Lung cancer cell line total RNA was isolated as described above and polyA$^+$ mRNA was prepared using the Microfast Track kit (Invitrogen). Two grams of mRNA or 10 g of total RNA was transferred to nylon membranes (Schleicher and Schuell) following denaturing gel electrophoresis. Hybridizations and washes were carried out under high stringency conditions in ExpressHyb buffer (Clontech) using hybridization and washing conditions described by the manufacturer. The probes used for northern blot analysis were the following. SOX2: 450 bp fragment (nucleotides 630-1080); SOX1: 751 bp fragment (nucleotides 1520-2271); SOX3: 330 bp fragment (nucleotides 442-772); SOX21: 680 bp fragment (nucleotides 2720-3400); and ID4: full-length cDNA (1322 bp).

Example 1

Isolation of Immunoreactive Clones from SCLC Cell Lines by SEREX

SEREX analysis of the SCLC cell line NCI-H740 with a pool of five sera from SCLC patients at 1:10$^3$ dilution resulted in the isolation of 37 clones coding for 8 known gene products (Table 1a). These eight genes were given SEREX gene designations of NIVY-SCLC-1 to NY-SCLC-8.

TABLE 1a

Genes isolated by SEREX analysis of the small cell lung cancer cell line NCI-H740

| SEQ ID NO: | Gene Designation | Gene/Sequence Identity [GenBank Accession No.] | Number of clones (% of total) |
|---|---|---|---|
| 3 | NY-SCLC-1 | SOX2 [Z31560] | 19 (51%) |
| 4 | NY-SCLC-2 | SOX1 [Y13436] | 1 (3%) |
| 5 | NY-SCLC-3 | ZIC2 [AF104902] | 9 (24%) |
| 6 | NY-SCLC-4 | ID4 [U28368] | 2 (5%) |
| 7 | NY-SCLC-5 | MAZ [M94046] | 1 (3%) |
| 8 | NY-SCLC-6 | MPP11 [X98260] | 3 (8%) |
| 9 | NY-SCLC-7 | eIF2B [U23028] | 1 (3%) |
| 10 | NY-SCLC-8 | RBP-1 [L07872] | 1 (3%) |
| | | Total: | 37 |

The most frequently isolated genes were SOX2 and ZIC2, comprising 51% and 24% of all clones. A single clone corresponding to SOX1 was also isolated from this library. SOX- and ZIC2-encoding clones showed very strong immunoreactivity with the SCLC patient sera. Other genes isolated included ID4, MPP11, MAZ, eIF2B and RBP-1. ID4 protein is a member of the dominant negative helix-loop-helix (HLH) proteins. This protein can interact with other HLH proteins such as the one encoded by Archaete-Scute and by virtue of not containing a DNA binding domain it acts as a repressor (Riechmann, et al., $Nucleic Acids Res.,$ 22: 749-55, 1994). The mRNA expression pattern of ID4 in normal tissues was found to be universal by Northern blot analysis. Seroreactivity against ID4 was moderate at 1:10³ sera dilution. MPP11 is another HLH protein-binding factor, and it has also been isolated from HeLa cells by M-phase protein-recognizing antibodies (Shoji, et al., *J. Biol. Chem.*, 270:24818-25, 1995; Matsumoto-Taniura, et al. *Mol. Biol. Cell*, 7: 1455-69, 1996). Seroreactivity against MPP11 was strong at a 1:1000 dilution of the SCLC sera. This antigen was also identified by SEREX analysis of gastric and breast cancer and is universally expressed. Other genes isolated from NCI-H740—the myc-associated Zinc-finger protein MAZ, the eukaryotic translation initiation factor eIF2B and the J-κ recombination signal binding protein (RBP-1)— were also previously identified by SEREX. MAZ, eIF2B and RBP-1 are expressed in multiple normal adult tissues.

The SEREX analysis of the second SCLC line SK-LC-13 with the same pooled sera from SCLC patients resulted in the identification of 14 clones corresponding to 10 genes (Table Ib), 4 of which were identical to those isolated from NCI-H740 and 6 were distinct (NY-SCLC-9 to NY-SCLC-14).

TABLE 1b

Genes isolated by SEREX analysis of the small cell lung cancer cell line SK-LC-13

| SEQ ID NO: | Gene Designation | Gene/Sequence Identity [GenBank Accession No.] | Number of clones (% of total) |
|---|---|---|---|
| 3 | NY-SCLC-1 | SOX2 [Z31560] | 2 (14%) |
| 11 | NY-SCLC-9 | SOX3 [X71135] | 1 (7%) |
| 12 | NY-SCLC-10 | SOX21 [AF107044] | 1 (7%) |
| 5 | NY-SCLC-3 | ZIC2 [AF104902] | 2 (14%) |
| 6 | NY-SCLC-4 | ID4 [U28368] | 1 (7%) |
| 8 | NY-SCLC-6 | MPP11 [X98260] | 3 (21%) |
| 13 | NY-SCLC-11 | KIAA0963 [AB023180.1] | 1 (7%) |
| 14 | NY-SCLC-12 | LAG-3 [X51985] | 1 (7%) |
| 15, 16 | NY-SCLC-13 | DKFZp434C196 [AL133561.1] | 1 (7%) |
| 17 | NY-SCLC-14 | Novel-2 | 1 (7%) |
| | | Total: | 14 |

SOX2 was isolated twice and in addition SOX3 and SOX21 were isolated, each represented by a single clone. ZIC2 was isolated twice. Other genes isolated that were identical to those from the NCI-H740 library included ID4, isolated once, and MPP11, which was represented by three immunoreactive clones. Among other genes identified, NY-SCLC-11 (KIAA0963) is an unknown gene with identical EST sequences derived from many tissues. Two novel genes (NY-SCLC-13) and (NY-SCLC-14) were isolated, one of which (NY-SCLC-14) showed no sequence identity to current GenBank entries. These two genes were intriguing in that their DNA sequences contain homopolymers of 24 bp and 6 bp repeats and would encode tandem octapeptides and dipeptides, respectively. NY-SCLC-12, lymphocyte activation gene-3 (LA G-3), is related to CD4 and has a restricted tissue expression pattern, possibly representing a differentiation antigen of lymphoid origin (Triebel, et al., *J. Exp. Med.*, 171: 1393-1405, 1990).

Example 2

Immunodominant Epitopes of ZIC2 and the SOX Proteins

Of 11 ZIC2 clones isolated, 7 clones were sequenced and 4 were evaluated by restriction mapping. The longest ZIC2 clone (NCI-H740 #32) was ~2.6 kb, the sequence of which extends beyond both 5' and 3' sequences of the ZIC2 cDNA entry in the GenBank (AF104902). The shortest clone (NCI-H740 #41) migrated as a ~1 kb band on agarose gels and its 5' end corresponded to nucleotide position 692 (amino acid residue 231) of AF104902. Reactivity of this clone with SCLC sera was comparable to other larger clones. As the intensity of the reactivity of this shorter clone was comparable to that of other larger ZIC2 clones, the seroreactive epitope(s) of ZIC2 polypeptide (SEQ ID NO:22) reside between amino acid residue 231 and the C-terminal end (amino acid residue 533).

Of the 24 SOX genes, 8 SOX2 clones and the SOX1, SOX3 and SOX21 clones were sequence analyzed while the remaining 13 SOX2 clones were analyzed and confirmed by restriction mapping. All SOX2 clones contained the full size cDNA (1085 bp) and the longest clone (NCI-H740 #2) had 54 additional nucleotides at its 5' untranslated region as compared to the SOX2 GenBank entry (Accession Number Z31560). The two SOX1 and SOX3 clones contained truncated cDNA inserts which lacked sequences 5' to those encoding the HMG-box while the SOX21 clone encoded the full length SOX21 protein, which has only 5 residues N-terminal to its HMG-box (FIG. 1). The most conserved region among these SOX cDNA clones is thus the HMG-box-encoding region which is 88 to 96% identical among the SOX Group B proteins. All sera that reacted with SOX1 also reacted with SOX2, SOX3 and SOX21 (see below), suggesting that at least part of the immunoreactivity of SCLC patient sera is directed against the conserved HMG-box of the SOX proteins.

Example 3

ZIC2 is Expressed Exclusively in Brain, Testis and Tumors

ZIC2 gene expression was analyzed by RT-PCR. The RNA quality was confirmed by successful amplification of p53 exons 5 and 6. Among normal tissues ZIC2 mRNA was only detectable in brain and to a lesser extent in testis but not in skin, kidney, small intestine, pancreas, uterus and lung. Of 11 SCLC cell lines analyzed, all 9 classical SCLC lines (SK-LC-13, NCI-H69, -H128, -H146, -H187, -H209, -H378, -H889, -H740) had detectable ZIC2 mRNA while two variant SCLC cell lines (NCI-H82 and NCI-H526) showed no or minimal expression. Among other cell lines, ZIC2 mRNA could be amplified in 100% (7/7) of non-small cell lung tumor cell lines and 83% (10/12) of melanoma cell lines (Table 2). Among tumor tissues, 50% (5/10) of melanoma, 50% (2/4) of colon cancer, 75% (3/4) of breast cancer, 86% (12/14) of head and neck cancer, 66% (6/9) of lung cancer, 50% (7/14) of transitional cancer, 50% (1/2) of leiomyosarcoma and 100% (2/2) of synovial sarcoma samples had detectable ZIC2 mRNA (Table 2).

TABLE 2

ZIC2 gene expression in cancer cell lines and tumor samples

| TUMOR CELL LINE | ZIC2 mRNA EXPRESSION |
|---|---|
| Melanoma | 10/12 (83%) |
| NSCLC | 7/7 (100%) |

TABLE 2-continued

ZIC2 gene expression in cancer cell lines and tumor samples

| TUMOR TYPE | ZIC2 mRNA EXPRESSION |
|---|---|
| Melanoma | 5/10 (50%) |
| Colon cancer | 2/4 (50%) |
| Breast cancer | 3/4 (75%) |
| Head & neck cancer | 12/14 (86%) |
| Lung cancer | 6/9 (66%) |
| Transitional cancer | 7/14 (50%) |
| Leiomyosarcoma | 1/2 (50%) |
| Synovial sarcoma | 2/2 (100%) |

Example 4

SOX Gene Expression Characteristics

Since SOX Group B genes are intronless, RT-PCR results using tissue RNA were often difficult to interpret due to the genomic DNA contamination of RNA samples. Therefore, their gene expression was evaluated by Northern blot analysis. An α-actin probe was used to confirm the RNA quality and quantity. Northern blots were exposed for 24 h (SOX2-SCLC blot), 72 h (SOX1), or 1 week (SOX3, SOX21 and SOX2-normal tissue blot).

Among normal tissues SOX2 mRNA could be detected in brain, testis and prostate, and at lower levels in small intestine and colon but not in heart, placenta, lung, liver, skeletal muscle, kidney, pancreas, spleen, thymus, ovary and peripheral blood leukocytes. SOX1, SOX3 and SOX21 mRNA were not detected in normal adult tissues, which is consistent with the current literature. SOX Group B expression in tumor cell lines was also examined. SOX2 was expressed in 5 of 10 SCLC cell lines (NCI-H69, NCI-H146, NCI-H378, NCI-H740 and SK-LC-13). SOX2 message was not detected in the three non-SCLC cell lines SK-LC-7, 8 and 17 or in the 8 melanoma cell lines SK-MEL-10, 12, 14, 24, 26, 28, 37 and Mz19. SOX1 mRNA was detected in 4 of 10 SCLC cell lines (NCI-H187, NCI-H209, NCI-H378 and SK-LC-13) while SOX3 mRNA could be detected in 2 of 10 SCLC cell lines (NCI-H740, and as a weaker signal in SK-LC-13). SOX1 and SOX3 required longer exposure times than SOX2, indicating their expression levels are lower than that of SOX2. SOX21 mRNA was not detected after prolonged exposure (1 week), indicating no or low levels of expression. Two variant SCLC cell lines, NCI-H82 and NCI-H526, had no detectable SOX Group B expression.

Example 5

SCLC Patient Sera Contain High-titer Antibodies to SOX and ZIC2 Proteins

Reactivity to phage clones containing SOX1, 2, 3, 21 and ZIC2 was titered against 17 SCLC patient sera and 16 normal adult sera. ZAP phages with no insert were mixed with the test clone and served as internal negative controls, visible as a background at $1:10^4$ serodilution on Lu113. Assays were scored positive only when test clones could be clearly distinguished from the control phages.

Only one of the 16 normal sera showed weak reactivity against SOX2 at a titer of 1:1000. In contrast, 7 of 17 patients (41%) had antibodies reactive with SOX1 and SOX2 containing phagemids while 29% (5/17) and 35% (6/17) had antibodies to SOX3 and SOX21 respectively. 29% (5/17) of patients had detectable anti-ZIC2 antibodies. The antibody titers measured up to 1:106 (Table 3). All five patient sera that had antibodies against ZIC2 also reacted with SOX proteins at varying titers; one (Lu113) was reactive at 1:106 while another (Lu139) was reactive only at a $1:10^3$ dilution. Two patients (Lu100 and A6) had antibodies against SOX1 and SOX2 proteins at 1:105 but no antibodies against ZIC2 even at $1:10^3$ dilution (Table 3).

TABLE 3

SOX and ZIC2 Reactivity of Small Cell Lung Cancer Patient Sera

| | Serum: | SOX1 | SOX2 | SOX3 | SOX21 | ZIC2 |
|---|---|---|---|---|---|---|
| 1 | Lu 94* | $1:10^5$ | $1:10^5$ | $1:10^4$ | $1:10^4$ | $1:10^5$ |
| 2 | Lu 100* | $1:10^5$ | $1:10^5$ | $1:10^4$ | $1:10^4$ | — |
| 3 | Lu 101* | — | — | — | — | — |
| 4 | Lu 104* | — | — | — | — | — |
| 5 | Lu 113* | $1:10^6$ | $1:10^6$ | $1:10^5$ | $1:10^5$ | $1:10^6$ |
| 6 | Lu 139 | $1:10^3$ | $1:10^3$ | — | — | $1:10^6$ |
| 7 | Lu 159 | — | — | — | — | — |
| 8 | A1 | $1:10^5$ | $1:10^6$ | $1:10^5$ | $1:10^5$ | $1:10^4$ |
| 9 | A2 | — | — | — | — | — |
| 10 | A3 | — | — | — | — | — |
| 11 | A4 | — | — | — | — | — |
| 12 | A5 | — | — | — | — | — |
| 13 | A6 | $1:10^5$ | $1:10^5$ | $1:10^3$ | $1:10^4$ | — |
| 14 | A7 | — | — | — | — | — |
| 15 | A8 | — | — | — | — | — |
| 16 | A9 | — | — | — | — | — |
| 17 | A10 | $1:10^4$ | $1:10^4$ | — | $1:10^3$ | $1:10^4$ |
| | | 7/17(41%) | 7/17(41%) | 5/17(29%) | 6/17(35%) | 5/17(29%) |

*Pooled sera used for SEREX analysis of the SCLC cell lines

All patients who had antibodies against SOX3 or SOX21 had antibodies at higher titers against SOX1 and SOX2. The presence of consistently higher titer antibodies against SOX1 and SOX2 suggests SOX1 and/or 2 as the main immunogenic tumor antigen in these patients, whereas the seroreactivity to SOX3 and SOX21 might be secondary to the share antigenic epitopes located within the highly conserved HMG-box among SOX proteins.

From the immunological standpoint, the high frequency and high titers of anti-SOX and anti-ZIC2 antibodies in these SCLC patients is striking. Anti-ZIC2 antibody was observed in 29% and anti-SOX antibody was observed in 41% of the SCLC sera tested. These sera were collected from a heterogeneous group of SCLC patients who were at different stages of their diseases, receiving various treatments, and with variable responses; one of the antibody-positive patients (Lu113) had no clinical evidence of residual disease when serum was collected and had subsequent recurrence of tumor. This means that if serum is collected from untreated cases of SCLC, the frequency of detecting anti-SOX and anti-ZIC2 antibodies can be substantially higher than the 30-40% rate found in this study. This frequency is significantly higher than the antibody responses seen against most other SEREX-defined antigens. Scanlan et al. (*Int. J. Cancer* 76:652-658, 1998) have evaluated large panels of SEREX antigens for seroreactivity in cancer and normal patients. It was found that antigens that elicit cancer-specific antibody responses tend to have detectable seral antibody in up to 20-25% of tumor patients, rarely exceeding 25%. In this regard, the immunogenicity of SOX and ZIC2 antigens in these patients are exceptional and this indicates that an antibody-based assay can be useful in the diagnosis of SCLC, e.g. as a screening test for the high-risk group. Also, for SCLC cases that have been shown to have high-titer antibodies, the titer of the antibody can be correlated to the clinical progression/remission of the disease. If the presence of antibody is dependent on the tumor load, as has been shown for another SEREX-defined antigen, NY-ESO-1 (Stockert et al., *J. Exp. Med.* 187:1349-1354, 1998), antibody monitoring in these patients may also be of clinical value.

In addition to its immunodiagnostic potential, SOX group B and ZIC2 products can be used as targets for cancer vaccines. The expression of these genes in brain may be a concern, particularly given the clinically-recognized paraneoplastic syndromes and their correlation to the aberrant expression of neural antigens in SCLC (Dalmau & Posner, *Arch. Neurol.* 56:405-408, 1999; Posner & Dalmau, *Curr. Opin. Immunol.* 9:723-729, 1997). However, despite the presence of high-titer anti-SOX and anti-ZIC2 antibodies, none of the seven antibody-positive patients in this study had neurological manifestations of the disease. In fact, the only patient in this study with paraneoplastic disease involving the cerebellum (patient A9) had no detectable anti-SOX Group B or anti-ZIC2 antibodies. The immune responses toward these antigens thus may not lead to autoimmune neurological disorders in most patients. Since SOX and ZIC2 genes are conserved in mice, preclinical studies can be carried out by SOX and/or ZIC2 vaccination in these experimental models. Indeed, HuD antigen, one of the antigens associated with paraneoplastic syndromes, has recently been used as a vaccine target in the murine model of small cell lung cancer, and antitumor activity was observed without neurological disease (Carpentier et al., *Clin. Cancer Res.* 4:2819-2824, 1998; Ohwada et al., *Am. J. Respir. Cell. Mol. Biol.* 21:37-43,1999).

Example 6

Preparation of Recombinant Cancer Associated Antigens

To facilitate screening of patients' sera for antibodies reactive with cancer associated antigens, for example by ELISA, recombinant proteins are prepared according to standard procedures. In one method, the clones encoding cancer associated antigens are subcloned into a baculovirus expression vector, and the recombinant expression vectors are introduced into appropriate insect cells. Baculovirus/insect cloning systems are preferred because post-translational modifications are carried out in the insect cells. Another preferred eukaryotic system is the Drosophila Expression System from Invitrogen. Clones which express high amounts of the recombinant protein are selected and used to produce the recombinant proteins. The recombinant proteins are tested for antibody recognition using serum from the patient which was used to isolated the particular clone, or in the case of cancer associated antigens recognized by allogeneic sera, by the sera from any of the patients used to isolate the clones or sera which recognize the clones' gene products.

Alternatively, the cancer associated antigen clones are inserted into a prokaryotic expression vector for production of recombinant proteins in bacteria. Other systems, including yeast expression systems and mammalian cell culture systems also can be used.

Example 7

Preparation of Antibodies to Cancer Associated Antigens

The recombinant cancer associated antigens produced as in Example 6 above are used to generate polyclonal antisera and monoclonal antibodies according to standard procedures. The antisera and antibodies so produced are tested for correct recognition of the cancer associated antigens by using the antisera/antibodies in assays of cell extracts of patients known to express the particular cancer associated antigen (e.g. an ELISA assay). These antibodies can be used for experimental purposes (e.g. localization of the cancer associated antigens, immunoprecipitations, Western blots, etc.) as well as diagnostic purposes (e.g., testing extracts of tissue biopsies, testing for the presence of cancer associated antigens).

The antibodies are useful for accurate and simple typing of small cell lung cancer tissue samples for expression of SOX Group B and ZIC2 genes. SCLC is usually diagnosed by endoscopic biopsies rather than surgical resection, and an adequate specimen for RNA extraction and RT-PCR typing may not be obtained in every case. These difficulties are further complicated by the fact that SOX Group B genes are intronless, and RT-PCR is often unreliable. The best technique to type the expression of these genes and circumvent these problems is by immunohistochemical analysis with specific antibody reagents.

Example 8

Expression of Cancer Associated Antigens in Cancers of Similar and Different Origin The expression of one or more of the cancer associated antigens is tested in a range of tumor samples to determine which, if any, other malignancies should be diagnosed and/or treated by the methods described herein. Tumor cell lines and tumor samples are tested for cancer associated antigen expression, preferably by RT-PCR according to standard procedures, e.g., as described for ZIC2 expression in Example 3 above. Northern blots also are used to test the expression of the cancer associated antigens. Antibody based assays, such as ELISA and western blot, also can be used to determine protein expression. A preferred method of testing expression of cancer associated antigens (in other cancers and in additional same type cancer patients) is allogeneic serotyping using a modified SEREX protocol (as described above).

In all of the foregoing, extracts from the tumors of patients who provided sera for the initial isolation of the cancer associated antigens are used as positive controls. The cells containing recombinant expression vectors described in the Examples above also can be used as positive controls.

The results generated from the foregoing experiments provide panels of multiple cancer associated nucleic acids and/or polypeptides for use in diagnostic (e.g. determining the existence of cancer, determining the prognosis of a patient undergoing therapy, etc.) and therapeutic methods (e.g., vaccine composition, etc.).

Example 9

HLA Typing of Patients Positive for Cancer Associated Antigens

To determine which HLA molecules present peptides derived from the cancer associated antigens of the invention, cells of the patients which express the cancer associated antigens are HLA typed. Peripheral blood lymphocytes are taken from the patient and typed for HLA class I or class II, as well as for the particular subtype of class I or class II. Tumor biopsy samples also can be used for typing. HLA typing can be carried out by any of the standard methods in the art of clinical immunology, such as by recognition by specific monoclonal antibodies, or by HLA allele-specific PCR (e.g. as described in WO97/31126).

Example 10

Characterization of Cancer Associated Antigen Peptides Presented by MHC Class I and Class II Molecules Antigens which provoke an antibody response in a subject may also provoke a cell-mediated immune response. Cells process proteins into peptides for presentation on MHC class I or class II molecules on the cell surface for immune surveillance. Peptides presented by certain MHC/HLA molecules generally conform to motifs. These motifs are known in some cases, and can be used to screen the small cell lung cancer associated antigens for the presence of potential class I and/or class II peptides. Summaries of class I and class II motifs have been published (e.g., Rammensee et al., *Immunogenetics* 41:178-228, 1995). Based on the results of experiments such as those described above, the HLA types which present the individual breast cancer associated antigens are known. Motifs of peptides presented by these HLA molecules thus are preferentially searched.

One also can search for class I and class II motifs using computer algorithms. For example, computer programs for predicting potential CTL epitopes based on known class I motifs has been described (see, e.g., Parker at al, *J. Immunol.* 152:163, 1994; D'Amaro et al., *Human Immunol.* 43:13-18, 1995; Drijfhout et al., *Human Immunol.* 43:1-12, 1995). Computer programs for predicting potential T cell epitopes based on known class II motifs has also been described (see, e.g. Sturniolo et al., *Nat Biotechnol* 17(6):555-61, 1999). HLA binding predictions can conveniently be made using an algorithm available via the Internet on the National Institutes of Health World Wide Web site. See also the website of: SYFPEITHI: An Jnternet Database for MHC Ligands and Peptide Motifs. Methods for determining HLA class II peptides and making substitutions thereto are also known (e.g. Strominger and Wucherpfennig (PCT/US96/03182)).

Example 11

Identification of the Portion of a Cancer Associated Polypeptide Encoding an Antigen To determine if the cancer associated antigens isolated as described above can provoke a cytolytic T lymphocyte response, the following method is performed. CTL clones are generated by stimulating the peripheral blood lymphocytes (PBLs) of a patient with autologous normal cells transfected with one of the clones encoding a cancer associated antigen polypeptide or with irradiated PBLs loaded with synthetic peptides corresponding to the putative protein and matching the consensus for the appropriate HLA class I molecule (as described above) to localize an antigenic peptide within the cancer associated antigen clone (see, e.g., Knuth et al., *Proc. Natl. Acad. Sci. USA* 81:3511-3515, 1984; van derBruggen et al., *Eur. J. Immunol.* 24:3038-3043, 1994). These CTL clones are screened for specificity against COS cells transfected with the cancer associated antigen clone and autologous HLA alleles as described by Brichard et al. (*Eur. J. Immunol.* 26:224-230, 1996). CTL recognition of a cancer associated antigen is determined by measuring release of TNF from the cytolytic T lymphocyte or by $^{51}$Cr release assay (Herin et al., *Int. J. Cancer* 39:390-396, 1987). If a CTL clone specifically recognizes a transfected COS cell, then shorter fragments of the cancer associated antigen clone transfected in that COS cell are tested to identify the region of the gene that encodes the peptide. Fragments of the cancer associated antigen clone are prepared by exonuclease III digestion or other standard molecular biology methods. Synthetic peptides are prepared to confirm the exact sequence of the antigen.

Optionally, shorter fragments of cancer associated antigen cDNAs are generated by PCR. Shorter fragments are used to provoke TNF release or $^{51}$Cr release as above.

Synthetic peptides corresponding to portions of the shortest fragment of the cancer associated antigen clone which provokes TNF release are prepared. Progressively shorter peptides are synthesized to determine the optimal cancer associated antigen tumor rejection antigen peptides for a given HLA molecule.

A similar method is performed to determine if the cancer associated antigen contains one or more HLA class II peptides recognized by T cells. One can search the sequence of the cancer associated antigen polypeptides for HLA class H motifs as described above. In contrast to class I peptides, class II peptides are presented by a limited number of cell types. Thus for these experiments, dendritic cells or B cell clones which express HLA class II molecules preferably are used.

TABLE 4

Sequence homologies

SEQ ID NO:15 (NY-SCLC-13 5' SEQUENCE)

AL133561.1, AC007324.53, AP000552.1, AP000550.1, AC007708.13, AC009288.12, AC007325.49, AC008103.23, AC008079.22, AC008018.18, AC007731.11, AC005500, AC012398.3, AC008132.33, AC011718.2, AL117481.1, AE001958.1, AJ243721.1, X70255, X54676, AL110383.1, AL041090.1, AW261390.1, AI904151.1, AA314127, H29680, H08571, R60682, R54134, R50027, R19696, R18168, R12223, F13183, F12174, F07553, F07164, F05322, F05321, F05267, F05235, T33549, Z43231, AI828436.1, AW226624.1, AW012831.1, AW012161.1, AI874452.1, AI391139, AI225578, AI099322, AA510280, AA475860, AA276058, AA277960, AA239475, AA139948, AA106968, AA073333, AA066928, AA002337,

TABLE 4-continued

Sequence homologies

W18896, W07975, AW148528.1, AI934011.1, AI885936.1, AI885982.1, AI824746.1, AI801523.1,
AI741661.1, AI679504.1, AI589998.1, AI567632.1, AI564170.1, AI520793.1, AA677535, AA292543,
F06393, AW142285.1, AW140928.1, AA520277.
SEQ ID NO:16 (NY-SCLC-13 3' SEQUENCE)

AL133561.1, AC007324.53, AP000552.1, AP000550.1, AC007708.13, AC009288.12, AC007325.49,
AC008103.23, AC008079.22, AC008018.18, AC005500, AC007731.11, AC012398.3, AC008132.33,
AC011718.2, AL117481.1, AE001958.1, X70255, X54676, AF022185, U00016, AL110383.1, AL041090.1,
AW261390.1, AI904151.1, AW012161.1, AI391139, AI741661.1, AW142285.1, AW140928.1, AA520277.
SEQ ID NO:17 (NY-SCLC-14)

X14112, D10879, Z68873.1, AJ009970.1, AF077000, M11043, AC004093, L04961, AC008124.8, AC005742,
AC000395, AL023802.1, U44088, AL031258.8, U92983, Z50194, Z63758, M55701, M80829, AF192802.1,
Z84494.1, AC005387, AC004490, Z93784.1, AC003976, M69157, AL031864.1, M11041, AF131866.1,
AL023284.1, AF039833, U62317, NM_003980.1, AF132809.1, NM_003632.1, U38195, U38193, S44199,
AB000634, NM_003459.1, NM_006245.1, D78360, AC004471, U04357, L77570, U52112, M97881, L22206,
NM_004565.1, AB018269.1, AE001198, AF022844, Z82173.2, AF167560.1, AC007032.2, AB020714.1,
AF037372, AC002984, U81524, U63850, Z64726, X80330, AL110210.1, AL096857.1, AL031597.7,
AL021579.1, AC005932, M63138, M28265, X80327, L14589, AC011718.2, Z92546.2, AC008018.18,
AP000353.1, AC004148, Y08701, AF023268, U77716, U46921, U46920, AC006549.27, Z99757.12,
AC005817.6, AL035090.10, AC003063.7, AC004828.2, AC006547.9, AC000097, AF051345, Z94162.1,
U34879, M84472.1, AF190826.1, M73779, AC002094, AW001248.1, AI863828.1, AI858055.1, AI813670.1,
AI684429.1, AI277482, AI580934.1, AA472637, W64993, AW043820.1, AW028151.1, AI949719.1,
AI887909.1, AI805058.1, AI804955.1, AI798900.1, AI741492.1, AI582191.1, AI348656, AI336325,
AI299745, AI276119, AI269740, AI262960, AI200633, AI097473, AA884197, AA527274, AA480684,
W68353, AI931453.1, AA726490, W98413, AW263065.1, AW211900.1, AI006238, AA255056, AA238335,
H27099, AA673074, AW139762.1, AL047473.1, AW223562.1, AW066814.1, AW031777.1, AI782249.1,
AI774556.1, AI586471.1, AA139570, AI923922.1, AV390350.1, AA505122, AA380178, AI853595.1,
AI851994.1, AI846520.1, AI154485, AI007056, AA467529, AA274838, AA261057, AA032648, W70846,
W71079, AA323008, C95416.1, AW210204.1, AA718506, AL042695.1, T25132, AI997515.1, AW205598.1,
AI686223.1, AI590082.1, AI378378, AI318623, AI318236, AI201238, AI200900, AI190426, AI022738,
AA916388, AA865035, AA845480, AA778028, AA744509, AA679215, AA558436, AA456062, AA418017,
AA328237, AA159291, AA129371, N33970, H43255, T77577, AI890886.1, AA292501, AI379199.1,
AI831459.1.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is:

1. A method for diagnosing cancer, comprising
contacting a biological sample isolated from a patient, who is suspected of having the cancer, with SOX1 (SEQ ID NO: 18) or ZIC2 (SEQ ID NO: 22) and determining the presence or level of an antibody that binds SOX1 (SEQ ID NO: 18) or ZIC2 (SEQ ID NO: 22) or antibodies that bind SOX1 (SEQ ID NO: 18) and ZIC2 (SEQ ID NO: 22), wherein the presence or level of said antibody or antibodies is an indication that the subject has cancer, wherein the cancer is small cell lung cancer.

2. The method of claim 1, wherein the sample is a body fluid, a body effusion or a tissue.

3. The method of claim 2, wherein the sample is blood or serum.

4. The method of claim 1, wherein SOX1 (SEQ ID NO:18) or ZIC2 (SEQ ID NO:22) are detectably labeled.

5. The method of claim 4, wherein the detectably labeled SOX1 (SEQ ID NO:18) or ZIC2 (SEQ ID NO:22) is labeled with a radioactive label or an enzyme.

6. The method of claim 1, wherein the nucleic acid molecule is SOX1 (SEQ ID NO:4).

7. The method of claim 1, wherein the nucleic acid molecule is ZIC2 (SEQ ID NO:5).

8. The method of claim 1, wherein the sample is contacted with SOX1 (SEQ ID NO:18) and ZIC2 (SEQ ID NO:22).

9. The method of claim 1, wherein the sample is contacted with SOX1 (SEQ ID NO:18).

10. The method of claim 1, wherein the sample is contacted with ZIC2 (SEQ ID NO:22).

* * * * *